(12) United States Patent
Juntunen et al.

(10) Patent No.: US 8,877,912 B2
(45) Date of Patent: Nov. 4, 2014

(54) NUCLEIC ACIDS ENCODING FUNGAL SERINE PROTEASE

(71) Applicant: AB Enzymes Oy, Rajamaki (FI)

(72) Inventors: Kari Juntunen, Espoo (FI); Leena Valtakari, Rajamaki (FI); Susanna Makinen, Layliainen (FI); Jarno Kallio, Jarvenpaa (FI); Jari Vehmaanpera, Klaukkala (FI); Pentti Ojapalo, Tuusula (FI); Marja Paloheimo, Vantaa (FI); George Szakacs, Budapest (HU)

(73) Assignee: AB Enzymes Oy, Rajamäki (FI)

( * ) Notice: Subject to any disclaimer, the term of this patent is extended or adjusted under 35 U.S.C. 154(b) by 0 days.

(21) Appl. No.: 14/067,040

(22) Filed: Oct. 30, 2013

(65) Prior Publication Data

US 2014/0134707 A1   May 15, 2014

Related U.S. Application Data

(62) Division of application No. 12/799,638, filed on Apr. 28, 2010, now Pat. No. 8,609,390.

(60) Provisional application No. 61/214,974, filed on Apr. 30, 2009.

(30) Foreign Application Priority Data

Apr. 30, 2009 (FI) ..................................... 20095499

(51) Int. Cl.
   *C07H 21/04* (2006.01)
   *C12N 9/58* (2006.01)
   *C11D 3/386* (2006.01)

(52) U.S. Cl.
   CPC  *C12N 9/58* (2013.01); *C11D 3/386* (2013.01); *C11D 3/38681* (2013.01)
   USPC .......................................................... 536/23.2

(58) Field of Classification Search
   CPC .................................. C12N 9/58; C12N 15/63
   See application file for complete search history.

(56) References Cited

U.S. PATENT DOCUMENTS

| | | | |
|---|---|---|---|
| 3,652,399 | A | 3/1972 | Isono et al. |
| 5,288,627 | A | 2/1994 | Nielsen et al. |
| 5,770,418 | A | 6/1998 | Yaver et al. |
| 5,843,745 | A | 12/1998 | Berka et al. |
| 5,962,765 | A | 10/1999 | St.Leger et al. |
| 6,300,116 | B1 | 10/2001 | Von der Osten et al. |
| 6,573,086 | B1 | 6/2003 | Emalfrak et al. |
| 6,682,924 | B1 | 1/2004 | Sierkstra et al. |
| 2004/0023355 | A1 | 2/2004 | Sierkstra et al. |
| 2010/0120649 | A1 | 5/2010 | Andersen |
| 2011/0003729 | A1 | 1/2011 | Juntunen et al. |
| 2011/0008870 | A1 | 1/2011 | Makinen et al. |
| 2011/0028375 | A1 | 2/2011 | Juntunen et al. |
| 2012/0107905 | A1 | 5/2012 | Juntunen et al. |

FOREIGN PATENT DOCUMENTS

| | | |
|---|---|---|
| EP | 0244234 | 11/1987 |
| EP | 0352244 A2 | 1/1990 |
| EP | 0519229 A2 | 5/1992 |
| EP | 0290567 | 6/1992 |
| EP | 0290569 | 6/1992 |
| EP | 0519229 | 12/1992 |
| EP | 0 479 870 | 10/2000 |
| EP | 1347045 | 9/2003 |
| EP | 1870453 A1 | 12/2007 |
| EP | 1 009 815 | 1/2008 |
| EP | 1464626 B1 | 11/2009 |
| EP | 1464626 A2 | 10/2010 |
| WO | WO88/03946 | 6/1988 |
| WO | 88/07581 | 10/1988 |
| WO | WO89/04361 | 5/1989 |
| WO | WO89/06270 | 7/1989 |
| WO | WO92/03529 | 3/1992 |
| WO | WO92/05239 | 4/1992 |
| WO | WO92/18599 | 10/1992 |
| WO | WO94/25583 | 11/1994 |
| WO | 96/18722 | 6/1996 |
| WO | WO97/02753 | 1/1997 |
| WO | WO97/08325 | 3/1997 |

(Continued)

OTHER PUBLICATIONS

McDonagh et al., Production of caseinophosphopeptides (CPPs) from sodium caseinate using a range of commercial protease preparations. International Dairy Journal (1998), 8(1), 39-45.*

(Continued)

*Primary Examiner* — Sheridan Swope

(74) *Attorney, Agent, or Firm* — Fish & Richardson P.C.

(57) ABSTRACT

The present invention is related to a fungal serine protease enzyme, which comprises an amino acid sequence the mature Fa_RF7182 enzyme having an amino acid sequence of SEQ ID NO: 18. The serine protease is obtainable from *Fusarium acuminatum*, more preferably from the deposited strain CBS 124084. Also disclosed are nucleic acid sequences encoding said protease, such as plasmid pALK2530 comprising the nucleotide sequence SEQ ID NO:12 deposited in *Escherichia coli* RF7803 under accession number DSM 22208 and plasmid pALK2531 comprising the full-length gene SEQ ID NO: 13 deposited in *E. coli* RF7879 under accession number DSM 22209, as well as fungal hosts, such as *Trichoderm*. Said protease is useful as an enzyme preparation applicable in detergent compositions and for treating fibers, for treating wool, for treating hair, for treating leather, for treating food or feed, or for any applications involving modification, degradation or removal of proteinaceous material.

46 Claims, 21 Drawing Sheets

(56) References Cited

FOREIGN PATENT DOCUMENTS

| WO | WO97/28243   | 8/1997  |
|----|--------------|---------|
| WO | 98/20116     | 11/1997 |
| WO | 02/08398     | 1/2002  |
| WO | 2006/073839  | 7/2006  |
| WO | 2007/145963  | 12/2007 |
| WO | 2008/045148  | 4/2008  |
| WO | 2009/096916  | 8/2009  |
| WO | 2010/039840  | 4/2010  |
| WO | 2010/125174  | 11/2010 |
| WO | 2010/125175  | 11/2010 |
| WO | 2011/003968  | 1/2011  |

OTHER PUBLICATIONS

Saeki et al., "Detergent Alkaline Proteases: Enzymatic Properties, Genes, and Crystal Structures," Journal of Bioscience and Bioengineering, 103(6):501-508 (2007).

Venalainen et al., "Evolutionary relationships of the prolyl oligopeptidase family enzymes," Eur. J. Biochem., 271:2705-2715 (2004).

Beg et al., "Purification and characterization of an oxidation-stable, thiol-dependent serine alkaline protease from *Bacillus mojavensis*," Enzyme and Microbial Technology, 32:394-304 (2003).

D'Acunzo, F. et al., "Oxidation of phenols by laccase and laccase-mediator systems", Eur. J. Biochem., vol. 269, (2002), pp. 5330-5335.

Fabbrini, M. et al., "Comparing the catalytic efficiency of some mediators of lacasse", Journal of Molecular Catalysis B: Enzymatic, vol. 16, (2002), pp. 231-240.

Galye et al., "Identification of regions in interleukin-1 alpha important for activity," J. Biol. Chem., 268(29):22105-22111 (1993).

Genbank Acc#AAA34209 from Geremia et al., Mol Microbiol May 1993;8(3):603-613. Alignment with Seq ID No. 10 of U.S. Appl. No. 12/803,456, 3 pages.

Guo et al., "Protein tolerance to random amino acid change," Proc. Natl. Acad. Sci. USA, 101(25):9205-9210 (2004).

Liao, J. et al., "Engineering proteinase K using machine learning and synthetic genes", BMC Biotechnology, vol. 7, No. 16, (2007), pp. 1-19.

McDonagh et al., "Production of caseinophosphopeptides (CPPs) from sodium caseinate using a range of commercial protease preparations," International Dairy Journal, 8(1):39-45 (1998).

Search Report issued in Finnish Patent Application No. 20106135 dated May 13, 2011, 1 page.

Uniprot database Acc# Q86ZV3_TRIHM from Steyaert et al., Mycologia 96: 1245-1252 (2004). Alignment with Seq ID No. 10 of U.S. Appl. No. 12/803,456, 2 pages.

UniProt_201110 database Acc#A4V8W7_TRIHA from Suarez et al., Curr. Genet., May 2007; 51(5):331-342. Epub Apr. 6, 2007. Alignment with Seq ID No. 18.

USPTO in house alignment AAA34209 from Geremia et al., Mol. Microbiol. May 1993;8(3):603-613. Alignment with Seq ID No. 10 of U.S. Appl. No. 12/803,456, 2 pages.

USPTO in house alignment Q86ZV3_TRIHM from Steyaert et al. Mycologia 96:1245-1252 (2004). Alignment with Seq ID No. 10 of U.S. Appl. No. 12/803,456, 1 page.

Whisstock et al., "Prediction of protein function from protein sequence and structure," Q. Rev. Biophys., 36(3):307-340 (2003) Review.

Abu-Shady, M. R. et al., "Production, Partial Purification and Some Properties of Thermostable Alkaline Protease from Malbranchea sulfurea and its Compatibility with Commercial Detergents", Afr. J. Mycol. and Biotech., vol. 9, No. 3, (2001), pp. 17-26.

Banerjee, U. C. et al., "Thermostable alkaline protease from *Bacillus brevis* and its characterization as a laundry detergent additive", Process Biochemistry, vol. 35, (1999), pp. 213-219.

Antal, Zs. et al.. "Colony growth, in vitro antagonism and secretion of extracellular enzymes in cold-tolerant strains of *Trichoderma* species", Mycol. Res., vol. 104, No. 5, (2000), pp. 545-549.

Dienes, D. et al., "Identification of a trypsin-like serine protease from *Trichoderma reesei* GM9414", Enzyme and Microbial Technology, vol. 40, (2007), pp. 1087-1094.

EMBL database (online), Database Accession No. BI750343, Jun. 15, 2004, from Harris, L. J. et al. "Expressed Sequence Tags from *Fusarium graminearum* mycelium", (Unpublished) (1 page).

EMBL database (online), Database Accession No. DR657362, Jul. 14, 2005, from Brown, D. W., et al., "Analysis of 87,000 expressed sequence tags reveals alternatively spliced introns in multiple genes of the fumonisin gene cluster", (Unpublished) (1 page).

EMBL database (online), Database Accession No. AM294980, Apr. 20, 2007, from Suarez, M. B., et al., "Characterization of genes encoding novel peptidases in the biocontrol fungus *Trichoderma harzianum* CECT 2413 using the TrichoEST functional genomics approach", Curr. Genet. vol. 51, No. 5, (2007), pp. 331-342 (2 pages).

European Patent Office database (online), Database Accession No. GM007507, Nov. 20, 2008, from Madison, E.L., "Protease screening methods and proteases identified thereby"; Sequence 313 from Patent No. WO2008045148-A1, Apr. 17, 2008 (1 page).

EPO database (online), Database Accession No. HC687299, May 10, 2010, from Shasky, J. et al., "Methods for producing polypeptides in enzyme-deficient mutants of fusarium venenatum; Sequence 84 from Patent WO2010039840", Patent No. WO2010039840-A1, Apr. 8, 2010 (1 page).

Gaucher, G. M. et al., "567. Thermomycolin", Handbook of Proteolytic Enzymes, (2004), pp. 1834-1835.

Gayle, R. B. et al., "Identification of Regions in Interleukin-1α Important for Activity", The Journal of Biological Chemistry, vol. 268, No. 29, (1993), pp. 22105-22111.

Genbank database, Database Accession No. AAA34209.1, May 28, 1993, from Geremia, R.A. et al., "Molecular Characterization of the proteinase-encoding gene, prb1, related to mycoparasitism by *Trichoderma harzianum*", Molecular Microbiology, vol. 8, No. 3, (1993), pp. 603-613 (3 pages).

Geremia, R. A. et al., "Molecular characterization of the proteinase-encoding gene, prb1, related to mycoparasitism by *Trichoderma harzianum*", Molecular Microbiology, vol. 8, No. 3, (1993), pp. 603-613.

Kelly, J. M. et al., "Transformation of *Aspergillus niger* by the amdS gene of *Aspergillus nidulans*", The EMBO Journal, vol. 4, No. 2, (1985), pp. 475-479.

Kredics, L. et al., "Extracellular Proteases of *Trichoderma* Species", Acta Microbiologica et Immunologica Hungarica, vol. 52, No. 2, (2005), pp. 169-184.

Manonmani, H.K. et al. "Purification and properties of an extracellular proteinase of *Trichoderma koningii*", Enzyme Microb. Technol., vol. 15, (1993), pp. 624-628.

Martinez, D. et al., "Gene sequencing and analysis of the biomass-degrading fungus *Trichoderma reesei* (syn. *Hypocrea jecorina*)", Nature Biotechnology, vol. 26., No. 5, (2008), pp. 553-560.

Maurer, K. H. et al. "Enzymes, Detergent", Encyclopedia of Industrial Biotechnology: Bioprocess, Bioseparation, and Cell Technology (Michael C. Flickinger, ed.), John Wiley & Sons, Inc., (2010), pp. 1-17.

NCBI Refseq Database (online), Database Accession No. XP_383491, Apr. 9, 2008, No Author Found, Hypothetical protein FG03315.1 (*Gibberella zeae* PH-1) (1 page).

Ong, P. S. et al., "Production, purification and characterization of thermomycolase, the extracellular serine protease of the thermophilic fungus *Malbranchea pulchella* var. sulfurea", Can. J. Microbiol., vol. 22, (1975), pp. 165-175.

Pozo, M. J., "Functional analysis of tvsp1, a serine protease-encoding gene in the biocontrol agent *Trichoderma virens*", Fungal Genetics and Biology, vol. 41, (2004), pp. 336-348.

Sambrook, J. And Russell, D. W., Molecular Cloning, a Laboratory Manual, Cold Spring Harbor Laboratory, New York, US, (2001), pp. 6.51, 6.52, and 11.27.

Siezen, R. J. et al., "Subtilases: The superfamily of subtilisin-like serine proteases", Protein Science, vol. 6, (1997), pp. 501-523 (total pp. 30).

(56) References Cited

OTHER PUBLICATIONS

Steyaert, J. M. et al., "Co-expression of two genes, a chitinase (chit42) and proteinase (prb1) implicated in mycoparasitism by *Trichoderma hamatum*", Mycologia, vol. 96, No. 6, (2004), pp. 1245-1252.
Uniprot database (online), Database Accession No. C7ZKJ9, Oct. 13, 2009, from Coleman, J.J. et al, "The genome of *Nectria haematococca*: contribution of supernumerary chromosomes to gene expansion", PLoS Genet, 5: E1000618-E1000618, (2009), (1 page).
Uniprot database (online), Database Accession No. C9SL49, Nov. 24, 2009, from Ma, L.-J.J., et al, "Annotation of *Verticillium alboatrum* VaMs. 102.", Submitted (May 2008) to the EMBL/GenBank/DDBJ databases, (1 page).
Uniprot database (online), Database Accession No. E3Q3S5, Jan. 11, 2011, from Vaillancourt, L. et al,, "The genome sequence of *Glomerella graminicola* strain M1.001.", Submitted (Jun. 2009) to the EMBL/GenBank/DDBJ databases, (1 page).
Uniprot database (online), Database Accession No. C7YXB3, Oct. 13, 2009, from Coleman, J. J. et al., "The genome of *Nectria haematococca*: contribution of supernumerary chromosomes to gene expansion", PLoS Genet. 5: E1000618-E1000618, (2009), (1 page).
Uniprot database (online), Database Accession No. A5JS74, Jun. 26, 2007, from Gao, L. et al., "Gene cloning of serine protease from *Hirsutella minnesotania*", Submitted (Apr. 2007) to the EMBL/GenBank/DDBJ databases, (1 page).
Uniprot database (online), Database Accession No. Q69IF7, Sep. 13, 2004, from Hane, J.K. et al., "Dothideomycete-plant interactions illuminated by genome sequencing and EST analysis of the wheat pathogen *Stagonospora nodorum*.", Plant Cell, vol. 19, (2007), pp. 3347-3368, (1 page).
Uniprotkb database (online), Database Accession No. Q86ZV3-TRIHM, Feb. 10, 2009, from Steyaert, J. M. et al, Co-expression of two genes, a chitinase (chit42) and proteinase, Mycologia, vol. 96, No. 6, (2004), pp. 1245-1252 (1 page).
Uniprotkb database (online), Database Accession No. A4V8W7_TRIHA, Feb. 10, 2009, from Suarez, M. B. et al., "Characterization of genes encoding novel peptidases in the biocontrol fungus *Trichoderma harzianum* CECT 2413 using the TrichoEST functional genomics approach", Curr. Genet., vol. 51, (2007), pp. 331-342 (1 page).
Uniprotkb database (online), Database Accession No. Q874K4, Feb. 10, 2009, from Pozo, J. J. et al., "Functional analysis of tvsp1, a serine protease-encoding gene in the biocontrol agent *Trichoderma virens*", Fungal Genet. Biol., vol. 41, (2004), pp. 336-348 (1 page).
Uniprotkb database (online), Database Accession No. Q03420, Jun. 16, 2009, from Geremia, R. A. et al., "Molecular characterization of the preoteinase-encoding gene, prb1, related to mycoparasitism by *Trichoderma harzianum*", Mol. Microbiol., vol. 8, (1993), pp. 603-613 (2 pages).
Whisstock, J. C. et al., "Prediction of protein function from protein sequence and structure", Quarterly Reviews of Biophysics, vol. 36, No. 3 (2003), pp. 307-304.
International Search Report from corresponding PCT Application No. PCT/EP2011/068837 dated Dec. 15, 2011, (6 pages).
Suarez, M. B. et al. 2007. Characterization of genes encoding novel peptidases in the biocontrol fungus . . . Curr. Genet. 51:331-342.
Shimogaki, H. 1991. Purification and properties of a novel Surface-active agent . . . Agric. Biol. Chem 55(9): 2251-2258.
Shevchenko, A. et al. 1996. Mass spectrometric sequencing of proteins from silver-stained . . . Anal.Chem 68:850-858.
Rao, M.B et al. 1998. Molecular and Biotechnological aspects of microbial proteases. Microbiol. and Mol. Biol. Rev. 62(3): 597-635.
Raeder, U. et al. 1985. Rapid Preparation of DNA from filamentous fungi. Lett. Appl. Microbiol. 1: 17-20.

Poutanen, P. et al. 2001. Use of matrix-assisted laser desorption/ionization . . . Rapid Comm. Mass Spectrom. 15:1685-1962.
Penttila, M. et al. 1987 A versatile transformation system for the cellulolytic filamentous fungus . . . Gene 61: 155-164.
Nielsen, H. et al. 1997. Identification of procaryotic and eucaryotic signal peptides and . . . Protein Engineering 10(1): 1-6.
Nielsen, H. et al. 1998. Prediction of signal peptides and signal anchors by a hidden . . . Proc. 6th Intl. Conf. of Intelligent systems. pp. 122-130.
Mauer K-H. 2004. Detergent proteases. Current opinion in Biotechnology. 15: 330-334.
Maladier L. et al.1989 Cloning of the nitrate reductase gene (niaD) of *Aspergillus nidulans* . . . Gene 78: 147-157.
Laemmli, U.K. 1970 Cleavage of structural proteins during the assembly.. NAture 227915): 680-685.
Karhunen, T. et al. 1993. High frequency one-step gene replacement in *Trichoderma* . . . Mol Gen Genet 241:515-522.
Kalisz, H. M. 1988. Microbial proteases. Advances in Biochemical engineering / Biotechnology. vol. 36 pp. 1-65.
Joutsjoki, V. V. et al. 1993. Transformation of *Trichoderma reesei* with the Hormoconis . . . Curr Genet 24: 223-228.
Gurr, S. J. et al.1987 The structure and organization of nuclear genes . . . pp. 93-139. In (JR Kinghorn, ed.) Gene Structure in Eukaryotic Microbes.
Germia, R.A. et al 1993. Molecular characterization of the proteinase-encoding . . . Molec. Microbiol. 8(3):603-613.
Gasteiger, E. et al. 2003 ExPASy: the proteomics server for in-depth . . . Nucleic Acid Res. 31(13): 3784-3788.
Edman P. and Begg, G. 1967. Eur. J. Biochem. 1: 80-91.
Cherry, J.R. and Fidantsef, A. L. 2003. Directed evolution of industrial enzymes . . . Curr. Opinion in biotechnol. 14: 438-443.
Chen, Y-J and Inoye, M. 2008. The intramolecular chaperone mediated protein folding. Curr. Opinion in Structural Biology. 18:765-770.
Bolton, E.T. and McCarthy B.J. 1962. A general method for the isolation of RNA..Proc Nat. A. S. 48: 1390-1397.
Anwar, A. and Saleemuddin, M. 1998 Alkaline proteases: a review. Bioresource Technology 64: 175-183.
AMFEP list of commercial enzymes. www. amfep.org updated Nov. 30, 2007.
Altschul S.F. et al. 1990 Basic Local Alignment Search Tool J. Moi. Biol 215:403-410.
Gupta, R. et al. 2002. An overview on fermentation, downstream processing . . . Appl. Microbiol Biotechnol. 60:381-395.
Paloheimo, M. et al. 2003. High yield Production of a Bacterial Xylanase in the filamentous fungus . . . Appl. Env. Microbiol. p. 7073-7082.
NCBI REFSEQ Database, Apr. 9, 2008 "Hypothetical protein FG03315.1 (*Gibberella zease* PH-1)", version XP_383491.1., Database accession No. XP-383491.
Database EMBL (online), Jun. 15, 2004. Fg02_08b01_R Fg02_AAFC_ECORC_Fusarium_graminearum-mycelium *Gibberella zeae* cDNA clone Fg02_08b01, mRNA sequence.: Expressed sequence tags from *Fusarium gramineum* mycelium. Database accession No. BI750343.
Database UNIPROT (online), Feb. 10, 2009. "Full=Serin endopeptidase" *Trichoderma harzianum* (hypocrea lixii). ID A4V8W7_TRIHA. Database accession No. A4V8W7.
European Patent Office Database (online), Nov. 20, 2008. Sequence 313 from patent WO2008045148:, Hypoxrea lixii proteinn, ID GM007507, Database accession No. GM007507.
Database EMBL (online), Jul. 14 2005. "EST 10474749 FvN Gibbereall amoniliformis cDNA clone FVNC210, mRNA sequences:\". Dtabase accession No. DR657362.

* cited by examiner

Fig. 1A

```
1    atgactagca tccgccgcct cgctctctac cttggagctc tgctccctgc agtgcttgct gctcctgctg gcgtcctgcaa ggtcgctaag
1    m  t  s    i  r  r    l  a  l  y  l  g  a    l  l  p    a  v  l  a    a  p  a    g  v  s  k    v  a  k 91   ctcgactctg tgccgacaa gtacatcatc accctcaagc ctgattcctc tgacgccaag gtcgaggctc acttgagctg ggtcgaggc
31   l  d  s    v  p  d   k  y  i  i  t  l  k    p  d  s  s  d  a  k    v  e  a    h  l  s    w  v  e  g 181  gtccaccgcc gcagccttgc taagcgcgac accgtcggtg ttgagaagac tttcaacatc agcagctgga gcgcttactc tggcgagttc
61   v  h  r    r  s  l   a  k  r  d  t  v  g    v  e  k  t  f  n  i    s  s  w    s  a  y    s  g  e  f 271  gaccaggcta ccattgatga gatcaagaag agccctgagg taagccttcc ggtactggcc taagtaacac aaatcaccaa catgccatag
91   d  q  a    t  i  d   e  i  k  k  s  p  e ............................................................

361  gttgctttcg ttgagcctga ctacactgtc tacctggact atgaggagtc atctgagctg tctgaccgcG CTCTGACCAC CCAGTCTGGT
104  v  a  f    v  e  p   d  y  t  v  y  l  d    y  e  e  s  s  e  l    s  d  r    A  L  T  T  Q  S  G 451  GCTCCCTGGG GTCTCGGTGC CATCTCCCAC AAGTCCTCTC GCTCCACCAG CTACATCTAC GACACCACTG CCGGTAGCGG CTCTTACGGA
134  A  P  W    G  L  G   A  I  S  H  K  S  S    R  S  T  S  Y  I  Y    D  T  T  A  G  S  G    S  Y  G 541  TATGTCGTAG ATAGTGGTAT CAACATCGCC CATGACGAGT TGGTGGCCG CATACCGACT TTGGTGGCCG TGCTACTCTC GGCTACAACG
164  Y  V  V    D  S  G   I  N  I  A  H  D  E    L  D  G  G  R  A  T    L  G  Y  N  A  A  G    A  H  T 631  GATACCCTCG GCCACGGAAC CCACGTTGCT GGTACCATCG GTACCCATGT TATGGTGTC TCCAAGAAGG CCAACCTCAT CTCTGTCAAG
194  R  A  T    L  G  Y   N  A  A  G  A  H  T    I  G  T  H  V  A  G    T  I  G  T  H  V  M  V  S  K 721  GTCTTCGCCG GTAACCAGGC TGCTACATCT GTTATCCTTG ATGGCTTTAA CTGGGCCGTC AACGACATCA CCTCCAAGGG CCGTGCTGGC
224  V  F  A    G  N  Q   A  A  T  S  V  I  L    D  G  F  N  W  A  V    N  D  I  T  S  K  G    R  A  G 811  AAGTCGTTA TCAACATGTC TCTCGgtaag tagtttcgca ctcagaccta tacatgaaa tcactaacca agacaccagG CGGACCTTCT
254  K  S  V    I  N  M   S  L  ..............................................................  G  G  P  S 901  TCTGCTACTT GGACCACTGC CATCAACGCT GGATACAACG CTCCGTTGTC CTCCGTTGTC GCTGCCGGTA ACGGTGATGT CAATGGCAAC
266  S  A  T    W  T  T   A  I  N  A  G  Y  N    A  G  V  L  S  V  V    A  A  G    N  G  D  V    N  G  N
```

Fig. 1B

```
 991  CCTCTCCCCG TCTCTAGCCA GTCTCCTGCC AACGCCCCCA ACGCCCTGAC CGTCGCTGCC ATTGACTCCA ACTGGGCCAC TGCCTCTTTC
 296   P  L  P   V  S  S   Q  S  P  A   N  A  P    N  A  L  T   V  A  A    I  D  S   N  W  R  T   A  S  F

1081  ACCAACTACG GTGCCGGTGT TGATATCTTC GGCCCCGGTG TCAACATTCT GTCCGCCTGG ATCGGCTCCA GCACCGCTAC CAACACCATC
 326   T  N  Y   G  A  G   V  D  I  F   G  P  G    V  N  I  L   S  A  W    I  G  S   S  T  A  T   N  T  I

1171  AGCGGAACTT CCATGGCCCT CCCCCACCTT GCTGGTCTTG CTCTCTACCT CCAGGTCCTT GAGGGTCTTA GCACTCCCTGC TGCTGTCACC
 356   S  G  T   S  M  A   S  P  H  L   A  G  L    A  L  Y  L   Q  V  L    E  G  L   S  T  P   A  A  V  T

1261  AACCGCATCA AGGCTCTTGG TACCTCTGGC AAGGTCACTG GTAGCCTCAG CGGCAGCCCC AACCTCGTTG CCTACAACGG TAACGGTGCT
 386   N  R  I   K  A  L   G  T  S  G   K  V  T    G  S  L  S   G  S  P    N  L  V   A  Y  N  G   N  G  A

1351  TAG
 416   *
```

Temperature profile of recombinant protein Fa_RF7182
pH 9 using 15 min.

Effect of pH on the activity of recombinant Fa_RF7182 protein
40 mM Britton-Robinson buffer
pH 6 to pH 12 and reaction temperature was 50°C, 15 min.

Performance of recombinant protein Fa_RF7182
Blood-milk-ink stain
30°C, pH 9, 60 min.

Performance of Fa_RF7182
Blood-milk-ink stain
50°C, pH 9, 60 min.

Performance of recombinant protein Fa_RF7182
Blood-milk-ink stain
Detergent powder
40°C and pH 10

Performance of recombinant protein Fa_RF7182
Blood-milk-ink stain
Liquid detergent Ariel Sensitive
40°C, pH approx. 7.9, 60 min.

Performance of recombinant protein Fa_RF7182
Blood-milk-ink stain
Liquid base detergent for coloured fabrics
30 °C, Detergent concentration 5 g/l and pH 7.5.

Performance of recombinant protein Fa_RF7182
Blood-milk-ink stain
Liquid base detergent for coloured fabrics
30 °C, Detergent concentration 5 g/l (enzyme dosage calculated as protein).

Performance of recombinant protein Fa_RF7182
Blood-milk-ink stain
Liquid base detergent for coloured fabrics
30 °C, Detergent concentration 3.3 g /l and pH 7.4

Performance of recombinant protein Fa_RF7182
Blood-milk-ink stain
Liquid base detergent for coloured fabrics
30 °C, Detergent concentration 1 g/l and pH 7.3

Performance of recombinant protein Fa_RF7182
Blood-milk-ink stain
Ariel Sensitive
30 °C, Detergent concentration 5 g/l and pH 8

Performance of recombinant protein Fa_RF7182
Blood-milk-ink stain
Ariel Sensitive
30 °C, Detergent concentration 5 g/l (enzyme dosage calculated as protein)

Performance of recombinant protein Fa_RF7182
Blood-milk-ink stain
Ariel Sensitive
30 °C, Detergent concentration 3.3 g /l and pH 7.9

Performance of recombinant protein Fa_RF7182
Blood-milk-ink stain
Ariel Sensitive
30 °C, Detergent concentration 1 g/l and pH 7.6

Performance of recombinant protein Fa_RF7182
Launder Ometer tests
Liquid Base detergent for coloured fabrics, 30°C
Blood-milk-ink / PE-cotton Performance of recombinant protein Fa_RF7182
Launder Ometer tests
Liquid Base detergent for coloured fabrics, 30°C
Blood-milk-ink / Cotton Performance of recombinant protein Fa_RF7182
Launder Ometer tests
Liquid Base detergent for coloured fabrics, 30°C
Grass Performance of recombinant protein Fa_RF7182
Launder Ometer tests
Liquid Base detergent for coloured fabrics, 30°C
Cocoa

Fig. 12A
Total stain removal efficiency (delta %SR) of Fa_RF7182 enzyme preparation on eight different protease sensitive stains in full-scale washing trials.
Total stain removal efficiency when protease preparations were dosed according to the activity.

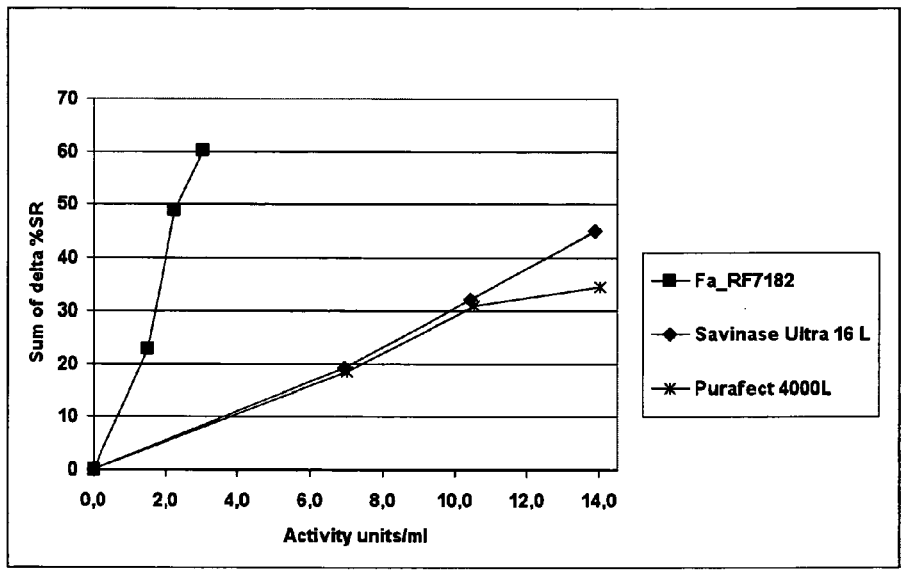

Fig. 12B
Total stain removal efficiency (delta %SR) of Fa_RF7182 enzyme preparation on eight different protease sensitive stains in full-scale washing trials.
Total stain removal efficiency when protease preparations were dosed according to the amount of protein.

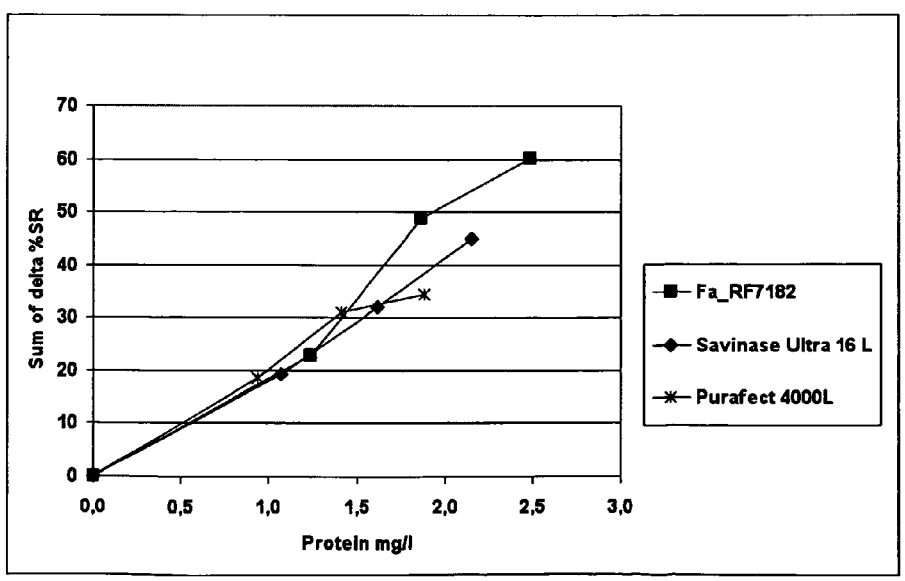

Stain removal effecting in liquid detergent base for coloured fabrics in full scale trial at 30°C.
Chocolate milk/pigment/Cotton (C-03-030/CFT)

Stain removal effecting in liquid detergent base for coloured fabrics in full scale trial at 30°C.
Blood-milk-ink//Cotton (C-05-059b/CFT)

Stain removal effecting in liquid detergent base for coloured fabrics in full scale trial at 30°C.
Blood/milk/ink/PE-Cotton (C-05-014/CFT)

Stain removal effecting in liquid detergent base for coloured fabrics in full scale trial at 30°C.
Groundnut oil/milk/Cotton (C-05-014/CFT)

Stain removal effecting in liquid detergent base for coloured fabrics in full scale trial at 30°C.
Egg Yolk/Pigment/Cotton (CS-38-010/CFT)

Performance of recombinant protein Fa_RF7182
Blood-milk-ink stain
10°C, pH 9, 60 min Performance of recombinant protein Fa_RF7182
Blood-milk-ink stain
20°C, pH 9, 60 min Performance of recombinant protein Fa_RF7182
Blood-milk-ink stain
30°C, pH 9, 60 min Performance of recombinant protein Fa_RF7182
Blood-milk-ink stain
40°C, pH 9, 60 min Performance of recombinant protein Fa_RF7182
Blood-milk-ink stain
50°C, pH 9, 60 min Performance of recombinant protein Fa_RF7182
Blood-milk-ink stain
60°C, pH 9, 60 min Performance of recombinant protein Fa_RF7182
Blood-milk-ink stain
Liguid base detergent
10°C, detergent concentration 3.3 g/l Performance of recombinant protein Fa_RF7182
Blood-milk-ink stain
Liguid base detergent
20°C, detergent concentration 3.3 g/l

SEQUENCE LISTING

```
<160> NUMBER OF SEQ ID NOS: 18

<210> SEQ ID NO 1
<211> LENGTH: 10
<212> TYPE: PRT
<213> ORGANISM: Fusarium acuminatum
<220> FEATURE:
<223> OTHER INFORMATION: Sequence of an aminoterminal peptide #3811 from
      Fusarium acuminatum RF7182 protease
<220> FEATURE:
<221> NAME/KEY: MOD_RES
<222> LOCATION: (2)..(2)
<223> OTHER INFORMATION: Leu or Ile
<220> FEATURE:
<221> NAME/KEY: MOD_RES
<222> LOCATION: (4)..(4)
<223> OTHER INFORMATION: Any amino acid
```

<400> SEQUENCE: 1

Ala Xaa Thr Xaa Gln Ser Asn Ala Pro Trp
1               5                   10

<210> SEQ ID NO 2
<211> LENGTH: 12
<212> TYPE: PRT
<213> ORGANISM: Fusarium acuminatum
<220> FEATURE:
<223> OTHER INFORMATION: Sequence of a tryptic peptide 1609,880 from
      Fusarium acuminatum RF7182 protease
<220> FEATURE:
<221> NAME/KEY: MOD_RES
<222> LOCATION: (7)..(7)
<223> OTHER INFORMATION: Leu or Ile
<220> FEATURE:
<221> NAME/KEY: MOD_RES
<222> LOCATION: (9)..(9)
<223> OTHER INFORMATION: Leu or Ile

<400> SEQUENCE: 2

Ser Gly Ala Pro Trp Gly Xaa Gln Xaa Ser His Lys
1               5                   10

<210> SEQ ID NO 3
<211> LENGTH: 18
<212> TYPE: PRT
<213> ORGANISM: Fusarium acuminatum
<220> FEATURE:
<223> OTHER INFORMATION: Sequence of a tryptic peptide 1793,957 from
      Fusarium acuminatum RF7182 protease
<220> FEATURE:
<221> NAME/KEY: MOD_RES
<222> LOCATION: (1)..(1)
<223> OTHER INFORMATION: Ala, Leu or Ile
<220> FEATURE:
<221> NAME/KEY: MOD_RES
<222> LOCATION: (2)..(2)
<223> OTHER INFORMATION: Ala, Leu or Ile
<220> FEATURE:
<221> NAME/KEY: MOD_RES
<222> LOCATION: (12)..(12)
<223> OTHER INFORMATION: Leu or Ile
<220> FEATURE:
<221> NAME/KEY: MOD_RES
<222> LOCATION: (15)..(15)
<223> OTHER INFORMATION: Leu or Ile

<400> SEQUENCE: 3

Xaa Xaa Thr Thr Gln Ser Gly Ala Pro Trp Gly Xaa Gly Ala Xaa Ser
1               5                   10                  15

His Lys

<210> SEQ ID NO 4
<211> LENGTH: 7
<212> TYPE: PRT
<213> ORGANISM: Fusarium acuminatum
<220> FEATURE:
<223> OTHER INFORMATION: Sequence of a tryptic peptide 743,494 from
      Fusarium acuminatum RF7182 protease
<220> FEATURE:
<221> NAME/KEY: MOD_RES
<222> LOCATION: (1)..(2)
<223> OTHER INFORMATION: Ala or Asn
<220> FEATURE:
<221> NAME/KEY: MOD_RES
<222> LOCATION: (3)..(4)
<223> OTHER INFORMATION: Leu or Ile

<400> SEQUENCE: 4

Xaa Xaa Xaa Xaa Ser Val Lys

<210> SEQ ID NO 5
<211> LENGTH: 6
<212> TYPE: PRT
<213> ORGANISM: Fusarium acuminatum
<220> FEATURE:
<223> OTHER INFORMATION: Sequence of a tryptic peptide 2103,832 (start
      2045,06) from Fusarium acuminatum RF7182 protease

<400> SEQUENCE: 5

Gly Gly Ala His Thr Asp
1               5

<210> SEQ ID NO 6
<211> LENGTH: 14
<212> TYPE: PRT
<213> ORGANISM: Fusarium acuminatum
<220> FEATURE:
<223> OTHER INFORMATION: Sequence of a tryptic peptide 2103,832 (start
      1406,57) from Fusarium acuminatum RF7182 protease
<220> FEATURE:
<221> NAME/KEY: MOD_RES
<222> LOCATION: (11)..(11)
<223> OTHER INFORMATION: Leu or Ile

<400> SEQUENCE: 6

Asn Gly His Gly Thr His Val Ala Gly Thr Xaa Asn Thr Lys
1               5                   10

<210> SEQ ID NO 7
<211> LENGTH: 31
<212> TYPE: PRT
<213> ORGANISM: Fusarium acuminatum
<220> FEATURE:
<223> OTHER INFORMATION: Sequence of a tryptic peptide 3662,692 from
      Fusarium acuminatum RF7182 protease
<220> FEATURE:
<221> NAME/KEY: MOD_RES
<222> LOCATION: (4)..(4)
<223> OTHER INFORMATION: Leu or Ile
<220> FEATURE:
<221> NAME/KEY: MOD_RES
<222> LOCATION: (22)..(22)
<223> OTHER INFORMATION: Leu or Ile
<220> FEATURE:
<221> NAME/KEY: MOD_RES
<222> LOCATION: (24)..(24)
<223> OTHER INFORMATION: Leu or Ile
<220> FEATURE:
<221> NAME/KEY: MOD_RES
<222> LOCATION: (29)..(29)
<223> OTHER INFORMATION: Leu or Ile

<400> SEQUENCE: 7

Thr Ser Tyr Xaa Tyr Asp Thr Thr Ala Gly Ser Gly Ser Tyr Gly Tyr
1               5                   10                  15

Val Val Asp Ser Gly Xaa Asn Xaa Ala His Tyr Ser Xaa Asn Arg
            20                  25                  30

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: The sequence of the oligonucleotide primer
      PRO123 derived from the peptide SEQ ID NO:3
<220> FEATURE:

```
<221> NAME/KEY: modified_base
<222> LOCATION: (6)..(6)
<223> OTHER INFORMATION: a, c, t or g
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (12)..(12)
<223> OTHER INFORMATION: a, c, t or g
<220> FEATURE:
<221> NAME/KEY: modified_base
<222> LOCATION: (15)..(15)
<223> OTHER INFORMATION: a, c, t or g

<400> SEQUENCE: 8
carwcnggng cnccntgggg                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: The sequence of the oligonucleotide primer
      PRO122 derived from the peptide SEQ ID NO:6
<220> FEATURE:
<221> NAME/KEY: modified_base
<222> LOCATION: (6)..(6)
<223> OTHER INFORMATION: a, c, t or g
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (15)..(15)
<223> OTHER INFORMATION: a, c, t or g
<220> FEATURE:
<221> NAME/KEY: modified_base
<222> LOCATION: (18)..(18)
<223> OTHER INFORMATION: a, c, t or g

<400> SEQUENCE: 9
cayggnacnc aygtngcngg                                                    20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: The sequence of the serine protease consensus
      oligonucleotide primer PRO60

<400> SEQUENCE: 10
gmrgccatrg aggtwccrgt sa                                                 22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: The sequence of the serine protease consensus
      oligonucleotide primer PRO61
```

-continued

<400> SEQUENCE: 11
ggmgmrgcca trgaggtwcc                                                  20

<210> SEQ ID NO 12
<211> LENGTH: 753
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: The sequence of the PCR fragment obtained using
      the primers PRO123 (SEQ ID NO:8) and PRO61 (SEQ ID NO:11)
      and Fusarium acuminatum RF7182 genomic DNA as a template

<400> SEQUENCE: 12
cagtctggtg cgccctgggg tctcggtgcc atctcccaca agtcgtctgg ctccaccagc      60
tacatctacg acaccactgc cggtagcggc tcttacggat atgtcgtaga tagtggtatc     120
aacatcgccc ataccgactt tggtggccgt gctactctcg ctacaacgc tgctggtggt      180 gctcacaccg ataccctcgg ccacggaacc cacgttgctg gtaccatcgg tggcaccaag    240
tatggtgtct ccaagaaggc caacctcatc tctgtcaagg tcttcgccgg taaccaggct    300
gctacatctg ttatccttga tggctttaac tgggccgtca acgacatca cctccaaggg     360 ccgtgctggc aagtccgtta tcaacatgtc tctcggtaag tagtttcgca ctcagaccta    420
tacatggaaa tcactaacca agacaccagg cggaccttct tctgctactt ggaccactgc    480
catcaacgct ggatacaacg ctggtgtcct ctccgttgtc gctgccggta acggtgatgt    540
caatggcaac cctctccccg tctctagcca gtctcctgcc aacgccccca acgccctgac    600
cgtcgctgcc attgactcca actggcgcac tgcctctttc accaactacg gtgccggtgt    660
tgatatcttc ggccccggtg tcaacattct gtccgcctgg atcggctcca gcaccgctac    720
caacaccatc agcggaacct ccatggcctc gcc                                  753

<210> SEQ ID NO 13
<211> LENGTH: 1353
<212> TYPE: DNA
<213> ORGANISM: Fusarium acuminatum
<220> FEATURE:
<223> OTHER INFORMATION: The nucleotide sequence of the full-length
      Fusarium acuminatum RF7182 protease gene (Fa prtS8A)
<220> FEATURE:
<221> NAME/KEY: CDS
<222> LOCATION: (1)..(309)
<220> FEATURE:
<221> NAME/KEY: CDS
<222> LOCATION: (361)..(834)
<220> FEATURE:
<221> NAME/KEY: CDS
<222> LOCATION: (889)..(1350)

<400> SEQUENCE: 13 atg act agc atc cgc cgc ctc gct ctc tac ctt gga gct ctg ctc cct      48
Met Thr Ser Ile Arg Arg Leu Ala Leu Tyr Leu Gly Ala Leu Leu Pro
1               5                   10                  15 gca gtg ctt gct gct cct gct ggc gtc tcc aag gtc gct aag ctc gac      96
Ala Val Leu Ala Ala Pro Ala Gly Val Ser Lys Val Ala Lys Leu Asp
            20                  25                  30 tct gtg ccc gac aag tac atc atc acc ctc aag cct gat tcc tct gac     144
Ser Val Pro Asp Lys Tyr Ile Ile Thr Leu Lys Pro Asp Ser Ser Asp
        35                  40                  45 gcc aag gtc gag gct cac ttg agc tgg gtc gag ggc gtc cac cgc cgc     192

```
              Ala Lys Val Glu Ala His Leu Ser Trp Val Glu Gly Val His Arg Arg
                   50                  55                  60 agc ctt gct aag cgc gac acc gtc ggt gtt gag aag act ttc aac atc        240
Ser Leu Ala Lys Arg Asp Thr Val Gly Val Glu Lys Thr Phe Asn Ile
 65                  70                  75                  80 agc agc tgg agc gct tac tct ggc gag ttc gac cag gct acc att gat        288
Ser Ser Trp Ser Ala Tyr Ser Gly Glu Phe Asp Gln Ala Thr Ile Asp
                 85                  90                  95 gag atc aag aag agc cct gag gtaagccttc cggtactggc ctaagtaaca           339
Glu Ile Lys Lys Ser Pro Glu
                100 caaatcacca acatgccata g gtt gct ttc gtt gag cct gac tac act gtc        390
                       Val Ala Phe Val Glu Pro Asp Tyr Thr Val
                                    105                 110 tac ctg gac tat gag gag tca tct gag ctg tct gac cgc gct ctg acc        438
Tyr Leu Asp Tyr Glu Glu Ser Ser Glu Leu Ser Asp Arg Ala Leu Thr
            115                 120                 125 acc cag tct ggt gct ccc tgg ggt ctc ggt gcc atc tcc cac aag tcg        486
Thr Gln Ser Gly Ala Pro Trp Gly Leu Gly Ala Ile Ser His Lys Ser
130                 135                 140                 145 tct ggc tcc acc agc tac atc tac gac acc act gcc ggt agc ggc tct        534
Ser Gly Ser Thr Ser Tyr Ile Tyr Asp Thr Thr Ala Gly Ser Gly Ser
                150                 155                 160 tac gga tat gtc gta gat agt ggt atc aac atc gcc cat acc gac ttt        582
Tyr Gly Tyr Val Val Asp Ser Gly Ile Asn Ile Ala His Thr Asp Phe
            165                 170                 175 ggt ggc cgt gct act ctc ggc tac aac gct gct ggt ggt gct cac acc        630
Gly Gly Arg Ala Thr Leu Gly Tyr Asn Ala Ala Gly Gly Ala His Thr
        180                 185                 190 gat acc ctc ggc cac gga acc cac gtt gct ggt acc atc ggt ggc acc        678
Asp Thr Leu Gly His Gly Thr His Val Ala Gly Thr Ile Gly Gly Thr
        195                 200                 205 aag tat ggt gtc tcc aag aag gcc aac ctc atc tct gtc aag gtc ttc        726
Lys Tyr Gly Val Ser Lys Lys Ala Asn Leu Ile Ser Val Lys Val Phe
210                 215                 220                 225 gcc ggt aac cag gct gct aca tct gtt atc ctt gat ggc ttt aac tgg        774
Ala Gly Asn Gln Ala Ala Thr Ser Val Ile Leu Asp Gly Phe Asn Trp
                230                 235                 240 gcc gtc aac gac atc acc tcc aag ggc cgt gct ggc aag tcc gtt atc        822
Ala Val Asn Asp Ile Thr Ser Lys Gly Arg Ala Gly Lys Ser Val Ile
            245                 250                 255 aac atg tct ctc ggtaagtagt ttcgcactca gacctataca tggaaatcac            874
Asn Met Ser Leu
            260 taaccaagac acca ggc gga cct tct tct gct act tgg acc act gcc atc        924
               Gly Gly Pro Ser Ser Ala Thr Trp Thr Thr Ala Ile
                              265                 270 aac gct gga tac aac gct ggt gtc ctc tcc gtt gtc gct gcc ggt aac        972
Asn Ala Gly Tyr Asn Ala Gly Val Leu Ser Val Val Ala Ala Gly Asn
275                 280                 285 ggt gat gtc aat ggc aac cct ctc ccc gtc tct agc cag tct cct gcc       1020
Gly Asp Val Asn Gly Asn Pro Leu Pro Val Ser Ser Gln Ser Pro Ala
290                 295                 300                 305 aac gcc ccc aac gcc ctg acc gtc gct gcc att gac tcc aac tgg cgc       1068
Asn Ala Pro Asn Ala Leu Thr Val Ala Ala Ile Asp Ser Asn Trp Arg
                310                 315                 320 act gcc tct ttc acc aac tac ggt gcc ggt gtt gat atc ttc ggc ccc       1116
Thr Ala Ser Phe Thr Asn Tyr Gly Ala Gly Val Asp Ile Phe Gly Pro
            325                 330                 335
```

```
ggt gtc aac att ctg tcc gcc tgg atc ggc tcc agc acc gct acc aac      1164
Gly Val Asn Ile Leu Ser Ala Trp Ile Gly Ser Ser Thr Ala Thr Asn
        340                 345                 350 acc atc agc gga act tcc atg gcc tcc ccc cac ctt gct ggt ctt gct      1212
Thr Ile Ser Gly Thr Ser Met Ala Ser Pro His Leu Ala Gly Leu Ala
    355                 360                 365 ctc tac ctc cag gtc ctt gag ggt ctt agc act cct gct gct gtc acc      1260
Leu Tyr Leu Gln Val Leu Glu Gly Leu Ser Thr Pro Ala Ala Val Thr
370                 375                 380                 385 aac cgc atc aag gct ctt ggt acc tct ggc aag gtc act ggt agc ctc      1308
Asn Arg Ile Lys Ala Leu Gly Thr Ser Gly Lys Val Thr Gly Ser Leu
                390                 395                 400 agc ggc agc ccc aac ctc gtt gcc tac aac ggt aac ggt gct tag          1353
Ser Gly Ser Pro Asn Leu Val Ala Tyr Asn Gly Asn Gly Ala
            405                 410                 415

<210> SEQ ID NO 14
<211> LENGTH: 415
<212> TYPE: PRT
<213> ORGANISM: Fusarium acuminatum
<220> FEATURE:
<223> OTHER INFORMATION: The deduced amino acid sequence of the
      full-length Fusarium acuminatum RF7182 protease (Fa_RF7182),
      including amino acids Met1 to Ala415

<400> SEQUENCE: 14

Met Thr Ser Ile Arg Arg Leu Ala Leu Tyr Leu Gly Ala Leu Leu Pro
1               5                   10                  15

Ala Val Leu Ala Ala Pro Ala Gly Val Ser Lys Val Ala Lys Leu Asp
            20                  25                  30

Ser Val Pro Asp Lys Tyr Ile Ile Thr Leu Lys Pro Asp Ser Ser Asp
        35                  40                  45

Ala Lys Val Glu Ala His Leu Ser Trp Val Glu Gly Val His Arg Arg
    50                  55                  60

Ser Leu Ala Lys Arg Asp Thr Val Gly Val Glu Lys Thr Phe Asn Ile
65                  70                  75                  80

Ser Ser Trp Ser Ala Tyr Ser Gly Glu Phe Asp Gln Ala Thr Ile Asp
                85                  90                  95

Glu Ile Lys Lys Ser Pro Glu Val Ala Phe Val Glu Pro Asp Tyr Thr
            100                 105                 110

Val Tyr Leu Asp Tyr Glu Glu Ser Ser Glu Leu Ser Asp Arg Ala Leu
        115                 120                 125

Thr Thr Gln Ser Gly Ala Pro Trp Gly Leu Gly Ala Ile Ser His Lys
    130                 135                 140

Ser Ser Gly Ser Thr Ser Tyr Ile Tyr Asp Thr Thr Ala Gly Ser Gly
145                 150                 155                 160

Ser Tyr Gly Tyr Val Val Asp Ser Gly Ile Asn Ile Ala His Thr Asp
                165                 170                 175

Phe Gly Gly Arg Ala Thr Leu Gly Tyr Asn Ala Ala Gly Gly Ala His
            180                 185                 190

Thr Asp Thr Leu Gly His Gly Thr His Val Ala Gly Thr Ile Gly Gly
        195                 200                 205

Thr Lys Tyr Gly Val Ser Lys Lys Ala Asn Leu Ile Ser Val Lys Val
    210                 215                 220

Phe Ala Gly Asn Gln Ala Ala Thr Ser Val Ile Leu Asp Gly Phe Asn
225                 230                 235                 240

Trp Ala Val Asn Asp Ile Thr Ser Lys Gly Arg Ala Gly Lys Ser Val
                245                 250                 255
```

```
Ile Asn Met Ser Leu Gly Gly Pro Ser Ser Ala Thr Trp Thr Thr Ala
            260                 265                 270

Ile Asn Ala Gly Tyr Asn Ala Gly Val Leu Ser Val Val Ala Ala Gly
        275                 280                 285

Asn Gly Asp Val Asn Gly Asn Pro Leu Pro Val Ser Ser Gln Ser Pro
    290                 295                 300

Ala Asn Ala Pro Asn Ala Leu Thr Val Ala Ala Ile Asp Ser Asn Trp
305                 310                 315                 320

Arg Thr Ala Ser Phe Thr Asn Tyr Gly Ala Gly Val Asp Ile Phe Gly
                325                 330                 335

Pro Gly Val Asn Ile Leu Ser Ala Trp Ile Gly Ser Ser Thr Ala Thr
            340                 345                 350

Asn Thr Ile Ser Gly Thr Ser Met Ala Ser Pro His Leu Ala Gly Leu
        355                 360                 365

Ala Leu Tyr Leu Gln Val Leu Glu Gly Leu Ser Thr Pro Ala Ala Val
    370                 375                 380

Thr Asn Arg Ile Lys Ala Leu Gly Thr Ser Gly Lys Val Thr Gly Ser
385                 390                 395                 400

Leu Ser Gly Ser Pro Asn Leu Val Ala Tyr Asn Gly Asn Gly Ala
                405                 410                 415

<210> SEQ ID NO 15
<211> LENGTH: 1293
<212> TYPE: DNA
<213> ORGANISM: Fusarium acuminatum
<220> FEATURE:
<223> OTHER INFORMATION: The nucleotide sequence encoding the amino acid
      sequence of the proenzyme form of Fusarium acuminatum RF7182
      protease
<400> SEQUENCE: 15
gctcctgctg gcgtctccaa ggtcgctaag ctcgactctg tgcccgacaa gtacatcatc     60
accctcaagc ctgattcctc tgacgccaag gtcgaggctc acttgagctg ggtcgagggc    120
gtccaccgcc gcagccttgc taagcgcgac accgtcggtg ttgagaagac tttcaacatc    180
agcagctgga gcgcttactc tggcgagttc gaccaggcta ccattgatga gatcaagaag    240
agccctgagg taagccttcc ggtactggcc taagtaacac aaatcaccaa catgccatag    300
gttgctttcg ttgagcctga ctacactgtc tacctggact atgaggagtc atctgagctg    360
tctgaccgcg ctctgaccac ccagtctggt gctccctggg gtctcggtgc catctcccac    420
aagtcgtctg gctccaccag ctacatctac gacaccactg ccggtagcgg ctcttacgga    480
tatgtcgtag atagtggtat caacatcgcc cataccgact ttggtggccg tgctactctc    540
ggctacaacg ctgctggtgg tgctcacacc gataccctcg gccacggaac ccacgttgct    600
ggtaccatcg gtggcaccaa gtatggtgtc tccaagaagg ccaacctcat ctctgtcaag    660
gtcttcgccg gtaaccaggc tgctacatct gttatccttg atggctttaa ctgggccgtc    720
aacgacatca cctccaaggg ccgtgctggc aagtccgtta tcaacatgtc tctcggtaag    780
tagtttcgca ctcagaccta tacatggaaa tcactaacca agacaccagg cggaccttct    840
tctgctactt ggaccactgc catcaacgct ggatacaacg ctggtgtcct ctccgttgtc    900
gctgccggta acggtgatgt caatggcaac cctctccccg tctctagcca gtctcctgcc    960
aacgccccca acgccctgac cgtcgctgcc attgactcca actggcgcac tgcctctttc   1020
accaactacg gtgccggtgt tgatatcttc ggccccggtg tcaacattct gtccgcctgg   1080
```

```
atcggctcca gcaccgctac caacaccatc agcggaactt ccatggcctc cccccacctt   1140
gctggtcttg ctctctacct ccaggtcctt gagggtctta gcactcctgc tgctgtcacc   1200
aaccgcatca aggctcttgg tacctctggc aaggtcactg gtagcctcag cggcagcccc   1260
aacctcgttg cctacaacgg taacggtgct tag                                1293


<210> SEQ ID NO 16
<211> LENGTH: 395
<212> TYPE: PRT
<213> ORGANISM: Fusarium acuminatum
<220> FEATURE:
<223> OTHER INFORMATION: The amino acid sequence of the  proenzyme form
      of Fusarium acuminatum RF7182 protease, including amino acids
      Ala21 to Ala415 of the full-length protease

<400> SEQUENCE: 16

Ala Pro Ala Gly Val Ser Lys Val Ala Lys Leu Asp Ser Val Pro Asp
1               5                   10                  15

Lys Tyr Ile Ile Thr Leu Lys Pro Asp Ser Ser Asp Ala Lys Val Glu
            20                  25                  30

Ala His Leu Ser Trp Val Glu Gly Val His Arg Arg Ser Leu Ala Lys
        35                  40                  45

Arg Asp Thr Val Gly Val Glu Lys Thr Phe Asn Ile Ser Ser Trp Ser
    50                  55                  60

Ala Tyr Ser Gly Glu Phe Asp Gln Ala Thr Ile Asp Glu Ile Lys Lys
65                  70                  75                  80

Ser Pro Glu Val Ala Phe Val Glu Pro Asp Tyr Thr Val Tyr Leu Asp
                85                  90                  95

Tyr Glu Glu Ser Ser Glu Leu Ser Asp Arg Ala Leu Thr Thr Gln Ser
            100                 105                 110

Gly Ala Pro Trp Gly Leu Gly Ala Ile Ser His Lys Ser Ser Gly Ser
        115                 120                 125

Thr Ser Tyr Ile Tyr Asp Thr Thr Ala Gly Ser Gly Ser Tyr Gly Tyr
    130                 135                 140

Val Val Asp Ser Gly Ile Asn Ile Ala His Thr Asp Phe Gly Gly Arg
145                 150                 155                 160

Ala Thr Leu Gly Tyr Asn Ala Ala Gly Gly Ala His Thr Asp Thr Leu
                165                 170                 175

Gly His Gly Thr His Val Ala Gly Thr Ile Gly Gly Thr Lys Tyr Gly
            180                 185                 190

Val Ser Lys Lys Ala Asn Leu Ile Ser Val Lys Val Phe Ala Gly Asn
        195                 200                 205

Gln Ala Ala Thr Ser Val Ile Leu Asp Gly Phe Asn Trp Ala Val Asn
    210                 215                 220

Asp Ile Thr Ser Lys Gly Arg Ala Gly Lys Ser Val Ile Asn Met Ser
225                 230                 235                 240

Leu Gly Gly Pro Ser Ser Ala Thr Trp Thr Thr Ala Ile Asn Ala Gly
                245                 250                 255

Tyr Asn Ala Gly Val Leu Ser Val Val Ala Ala Gly Asn Gly Asp Val
            260                 265                 270

Asn Gly Asn Pro Leu Pro Val Ser Ser Gln Ser Pro Ala Asn Ala Pro
        275                 280                 285

Asn Ala Leu Thr Val Ala Ala Ile Asp Ser Asn Trp Arg Thr Ala Ser
    290                 295                 300

Phe Thr Asn Tyr Gly Ala Gly Val Asp Ile Phe Gly Pro Gly Val Asn
305                 310                 315                 320
```

-continued

```
Ile Leu Ser Ala Trp Ile Gly Ser Ser Thr Ala Thr Asn Thr Ile Ser
                325                 330                 335

Gly Thr Ser Met Ala Ser Pro His Leu Ala Gly Leu Ala Leu Tyr Leu
            340                 345                 350

Gln Val Leu Glu Gly Leu Ser Thr Pro Ala Ala Val Thr Asn Arg Ile
        355                 360                 365

Lys Ala Leu Gly Thr Ser Gly Lys Val Thr Gly Ser Leu Ser Gly Ser
    370                 375                 380

Pro Asn Leu Val Ala Tyr Asn Gly Asn Gly Ala
385                 390                 395

<210> SEQ ID NO 17
<211> LENGTH: 924
<212> TYPE: DNA
<213> ORGANISM: Fusarium acuminatum
<220> FEATURE:
<223> OTHER INFORMATION: The nucleotide sequence encoding the amino acid
      sequence of the mature form of Fusarium acuminatum RF7182 protease

<400> SEQUENCE: 17
gctctgacca cccagtctgg tgctccctgg ggtctcggtg ccatctccca caagtcgtct      60
ggctccacca gctacatcta cgacaccact gccggtagcg gctcttacgg atatgtcgta     120
gatagtggta tcaacatcgc ccataccgac tttggtggcc gtgctactct cggctacaac     180
gctgctggtg gtgctcacac cgataccctc ggccacggaa cccacgttgc tggtaccatc     240
ggtggcacca agtatggtgt ctccaagaag gccaacctca tctctgtcaa ggtcttcgcc     300
ggtaaccagg ctgctacatc tgttatcctt gatggcttta actgggccgt caacgacatc     360
acctccaagg gccgtgctgg caagtccgtt atcaacatgt ctctcggtaa gtagtttcgc     420
actcagacct atacatggaa atcactaacc aagacaccag gcggaccttc ttctgctact     480
tggaccactg ccatcaacgc tggatacaac gctggtgtcc tctccgttgt cgctgccggt     540
aacggtgatg tcaatggcaa ccctctcccc gtctctagcc agtctcctgc caacgccccc     600
aacgccctga ccgtcgctgc cattgactcc aactggcgca ctgcctcttt caccaactac     660
ggtgccggtg ttgatatctt cggccccggt gtcaacattc tgtccgcctg gatcggctcc     720
agcaccgcta ccaacaccat cagcggaact tccatggcct ccccccacct tgctggtctt     780
gctctctacc tccaggtcct tgagggtctt agcactcctg ctgctgtcac caaccgcatc     840
aaggctcttg gtacctctgg caaggtcact ggtagcctca gcggcagccc caacctcgtt     900
gcctacaacg gtaacggtgc ttag                                            924

<210> SEQ ID NO 18
<211> LENGTH: 289
<212> TYPE: PRT
<213> ORGANISM: Fusarium acuminatum
<220> FEATURE:
<223> OTHER INFORMATION: The amino acid sequence of the mature form of
      Fusarium acuminatum RF7182 protease, including amino acids Ala127
      to Ala415 of the full-length protease

<400> SEQUENCE: 18

Ala Leu Thr Thr Gln Ser Gly Ala Pro Trp Gly Leu Gly Ala Ile Ser
1               5                   10                  15

His Lys Ser Ser Gly Ser Thr Ser Tyr Ile Tyr Asp Thr Thr Ala Gly
            20                  25                  30

Ser Gly Ser Tyr Gly Tyr Val Val Asp Ser Gly Ile Asn Ile Ala His
        35                  40                  45
```

```
Thr Asp Phe Gly Gly Arg Ala Thr Leu Gly Tyr Asn Ala Ala Gly Gly
    50                  55                  60

Ala His Thr Asp Thr Leu Gly His Gly Thr His Val Ala Gly Thr Ile
65              70                  75                      80

Gly Gly Thr Lys Tyr Gly Val Ser Lys Ala Asn Leu Ile Ser Val
                85                  90                  95

Lys Val Phe Ala Gly Asn Gln Ala Ala Thr Ser Val Ile Leu Asp Gly
                100             105                 110

Phe Asn Trp Ala Val Asn Asp Ile Thr Ser Lys Gly Arg Ala Gly Lys
        115                 120                 125

Ser Val Ile Asn Met Ser Leu Gly Gly Pro Ser Ser Ala Thr Trp Thr
    130                 135                 140

Thr Ala Ile Asn Ala Gly Tyr Asn Ala Gly Val Leu Ser Val Val Ala
145                 150                 155                 160

Ala Gly Asn Gly Asp Val Asn Gly Asn Pro Leu Pro Val Ser Ser Gln
            165                 170                 175

Ser Pro Ala Asn Ala Pro Asn Ala Leu Thr Val Ala Ala Ile Asp Ser
            180                 185                 190

Asn Trp Arg Thr Ala Ser Phe Thr Asn Tyr Gly Ala Gly Val Asp Ile
            195                 200                 205

Phe Gly Pro Gly Val Asn Ile Leu Ser Ala Trp Ile Gly Ser Ser Thr
    210                 215                 220

Ala Thr Asn Thr Ile Ser Gly Thr Ser Met Ala Ser Pro His Leu Ala
225                 230                 235                 240

Gly Leu Ala Leu Tyr Leu Gln Val Leu Glu Gly Leu Ser Thr Pro Ala
                245                 250                 255

Ala Val Thr Asn Arg Ile Lys Ala Leu Gly Thr Ser Gly Lys Val Thr
            260                 265                 270

Gly Ser Leu Ser Gly Ser Pro Asn Leu Val Ala Tyr Asn Gly Asn Gly
            275                 280                 285

Ala
```

NUCLEIC ACIDS ENCODING FUNGAL SERINE PROTEASE

PRIORITY

This application is a divisional of U.S. application Ser. No. 12/799,638, filed Apr. 28, 2010 (now U.S. Pat. No. 8,609,390), which claims priority from the Finnish national application number FI20095499 filed on Apr. 30, 2009 and of the U.S. Provisional patent application No. 61/214,974 filed on Apr. 30, 2009. The contents of all of the above applications are incorporated herein by reference in their entireties.

FIELD OF THE INVENTION

The present invention relates to a fungal serine protease enzyme useful in various applications, particularly in laundry and dish-washing detergents. The invention relates to a nucleic acid molecule encoding said enzyme, a recombinant vector, a host cell for producing said enzyme, an enzyme composition comprising said enzyme as well as a process for preparing such composition. This invention relates also to various uses of said enzyme or composition comprising said enzyme.

BACKGROUND

Microbial proteases are among the most important hydrolytic enzymes and find applications in various industrial sectors, such as detergent, food, leather, pharmaceutical, diagnostics, waste management and silver recovery. Microbial extracellular proteases account for a major part, more than one third, of the total worldwide industrial enzyme sales (Cherry and Fidantsef, 2003). Approximately 90% of the commercial proteases are detergent enzymes (Gupta et al., 2002). Most commercial proteases, mainly neutral and alkaline are produced by organisms belonging to the genus *Bacillus*.

Serine proteases of the subtilisin family or subtilisins produced by *Bacillus* species form the largest subgroup of industrial proteases. These enzymes are commercially important as protein degrading component or additive of washing detergents. The commercial detergent preparations currently in use comprise the naturally occurring alkaline serine proteases originating or are recombinant protease preparations from *Bacillus* species (Maurer, 2004). Variants of the natural enzymes with improved catalytic efficiency and/or better stability towards temperature, oxidizing agents and changing washing conditions have been developed through site-directed and/or random mutagenesis. Examples of commercial proteases are, such as subtilisin Carlsberg (Alcalase®, Novozymes, DK), subtilisin 309 (Savinase®, Novozymes, DK), Subtilisin 147 (Esperase®, Novozymes, DK), Purafect® (Genencor Inc., USA), Kannase® (Novozymes, DK), Purafect® Ox, Properase® (Genencor Inc., USA) and the BLAP S and X series (Henkel, DE).

Several alkaline serine proteases (EC 3.4.21) and genes encoding these enzymes have also been isolated from eukaryotic organisms, including yeast and filamentous fungi. U.S. Pat. No. 3,652,399 and EP 519229 (Takeda Chemical Industries, Ltd., JP) disclose an alkaline protease from the genus *Fusarium* (asexual state, teleomorph) or *Gibberella*, (sexual state, anamorph) particularly from *Fusarium* sp. S-19-5 (ATCC 20192, IFO 8884), *F. oxysporum* f. sp. *lini* (IFO 5880) or *G. saubinetti* (ATCC 20193, IFO6608), useful in the formulation of detergent and other cleanser compositions. U.S. Pat. No. 5,288,627 (NovoNordisk A/S, DK) discloses an endoprotease preparation comprising an isolated serine protease which shows immunochemical identity to a protease derived from *F. oxysporum* DSM 2672. WO 88/03946 and WO 89/04361 (Novo Industri A/S, DK) disclose an enzymatic detergent additive and a detergent composition comprising a protease and a lipase, wherein the fungal protease is derived from *Fusarium*, particularly *F. oxysporum* or *F. solani*. A detergent additive comprising protease with specificity for peptide bonds adjacent to only one or two specific amino acids is disclosed in WO89/06270. WO1994025583 (NovoNordisk A/S, DK) discloses an active trypsin-like protease enzyme derivable from a *Fusarium* species, in particular a strain of *F. oxysporum* (DSM 2672), and the DNA sequence encoding the same. The amino acid sequence of a novel protease deriving from *Fusarium* sp. BLB (FERM BP-10493) is disclosed in WO 2006101140 (SODX Co. Ltd, Nakamura). Also, alkaline proteases from fungal species such as *Tritirachium* and *Conidiobolus* have been reported (reviewed in Anwar and Saleemuddin, 1998).

Use of fungal serine proteases in different applications is also known from several patent applications. For example, combination of a cellulase and a protease, particularly a trypsin-like protease from *Fusarium* sp. DSM 2672 as a detergent additive or composition is disclosed in WO 1992018599 (NovoNordisk A/S). Such detergent compositions may further comprise reversible protease inhibitors for stabilizing the enzyme(s) as disclosed in WO 1992003529 and WO 1992005239 (NovoNordisk A/S). Process for removal or bleaching of soiling or stains from cellulosic fabrics with an enzyme hybrid comprising a catalytically active amino acid sequence such protease linked to an amino acid sequence comprising a cellulose binding domain is disclosed in WO 1997028243 (NovoNordisk A/S). WO 1997002753 (NovoNordisk A/S) discloses a method for gentle cleaning of soiled process equipment using a lipase and a protease being preferably a serine protease obtainable from *Fusarium*.

Due to a need to save energy the washing temperatures are decreasing. In addition, the current consumer demands and increased use of synthetic fibers which cannot tolerate high temperatures have changed washing habits towards the use of low washing temperatures. EP 0290567 and EP 0290569 (Novo Nordisk A/S, DK) disclose low-temperature alkaline proteases from actinomycete (*Nocardiopsis dassonvillei*) and fungal (*Paecilomyces marquandii*) micro-organisms.

The socioeconomic challenges and governmental regulations have forced detergent industry to take in consideration many environmental aspects including not only the use of more lenient chemicals, which can be used in minor amounts and therefore leave less environmental waste trails, but also the need of energy saving. Detergent enzymes, particularly proteases, are important ingredient in detergent compositions. The need to save energy by decreasing the washing temperatures and the increased use of synthetic fibers which cannot tolerate high temperatures and current lifestyle have changed customer habits towards low washing temperatures and has created a demand for new enzymes, which are effective in low temperatures.

Despite the fact that numerous patent publications, reviews and articles have been published, in which serine proteases from various microorganisms, for example, the low temperature alkaline proteases from actinomycete (*Nocardiopsis dassonvillei*) and fungal (*Paecilomyces marquandii*) microorganisms are disclosed, e.g. in EP 0290567 and EP 0290569 (Novo Nordisk A/S, DK), there is still a great need for alternative serine proteases, which are suitable for and effective in modifying, degrading and removing proteinaceous materials particularly in low or moderate temperature ranges and which are stable in the presence of detergents with highly varying properties.

Detergent industry is making great advances in adapting its new products to customers' habits and needs, the properties of new textile products and new washing machines. It is evident that when developing new detergents, particularly laundry and dish wash compositions, a wide range of varying and rapidly changing demands have to be satisfied. In order to fulfill all varying demands of detergent industry and governmental regulations, new serine protease ingredients for detergent compositions should not only be able to accomplish their tasks in wide pH and temperature ranges and remain stable in variety of conditions, including mechanical and chemical interventions in combination with a variety of different detergents, it is also desirable that the serine protease can be produced in high amounts, which can be cost-effectively down-stream processed, by easy separation from fermentation broth and mycelia

SUMMARY OF THE INVENTION

The aim of the present invention is to provide a serine protease of fungal origin which shows broad substrate specificity, is active at broad pH ranges and has a broad temperature optimum, i.e. functions both at low and moderate temperatures. The serine proteases for laundry and dish detergents have to be stable also in the presence of detergents or to be compatible with detergents. Particularly, the object of the invention is to provide a serine protease, which is capable of removing proteinaceous material, including stains in washing laundry and dishes, at lower temperatures than the present commercial enzyme preparations, thereby saving energy. The fungal serine protease can be produced in high-yielding fungal hosts and its down-stream processing, e.g. separation of fermentation broth and mycelia is easy to perform.

The present invention relates to a fungal serine protease enzyme, which has serine protease activity and comprises an amino acid sequence of the mature Fa_RF7182 enzyme as defined in SEQ ID NO:18 or an amino acid sequence having at least 81% identity to the amino acid sequence of the mature Fa_RF7182 enzyme defined in SEQ ID NO:18.

The enzyme of the invention is obtainable from *Fusarium acuminatum*, more preferably from the deposited strain CBS 124084.

The enzyme has a molecular mass between 25 and 35 kDa. The optimal temperature of the enzyme is at range from 30° C. to 70° C. at pH 9. Said enzyme has pH optimum at the pH range of at least pH 6 to pH 12 at 50° C. The optimal temperature and pH optimum were determined using 15 min reaction time and casein as a substrate. The serine protease of the invention is capable in degrading or removing proteinaceous stains in the presence of detergent between 10° C. and 60° C.

The fungal serine protease enzyme of the invention is encoded by an isolated polynucleotide sequence, which hybridizes under stringent conditions with a polynucleotide sequence included in plasmid pALK2530 comprising the nucleotide sequence SEQ ID No:12 deposited in *E. coli* RF7803 under accession number DSM 22208.

Said enzyme is encoded by an isolated polynucleotide sequence, which encodes a polypeptide comprising an amino acid sequence of the mature Fa_RF7182 enzyme as defined in SEQ ID NO:18 or an amino acid sequence having at least 81% identity to the amino acid sequence of the mature Fa_RF7182 defined in SEQ ID NO:18. Preferably, said enzyme is encoded by an isolated nucleic acid molecule comprising the nucleotide sequence SEQ ID NO:17.

The full-length fungal serine protease enzyme of the invention is encoded by the polynucleotide sequence included in pALK2531 deposited in *Escherichia coli* RF7879 under accession number DSM 22209.

The fungal serine protease enzyme is produced from a recombinant expression vector comprising the nucleic acid molecule encoding a fungal serine protease of the invention operably linked to regulatory sequences capable of directing the expression of the serine protease encoding gene in a suitable host. Suitable hosts include heterologous hosts, preferably microbial hosts of the genus *Trichoderma, Aspergillus, Fusarium, Humicola, Chrysosporium, Neurospora, Rhizopus, Penicillium* and *Mortiriella*

Preferably said enzyme is produced in *Trichoderma* or *Aspergillus*, most preferably in *T. reesei*.

The present invention relates also to an isolated nucleic acid molecule encoding a fungal serine protease enzyme selected from the group consisting of:
(a) a nucleic acid molecule encoding a polypeptide having serine protease activity and comprising the amino acid sequence as depicted in SEQ ID NO:18;
(b) a nucleic acid molecule encoding a polypeptide having serine protease activity and has at least 81% identity to the amino acid sequence of SEQ ID NO:18;
(c) a nucleic acid molecule comprising the coding sequence of the nucleotide sequence as depicted in SEQ ID NO: 13;
(d) a nucleic acid molecule comprising the coding sequence of the polynucleotide sequence contained in DSM 22208 or DSM 22209;
(e) a nucleic acid molecule the coding sequence of which differs from the coding sequence of a nucleic acid molecule of any one of (c) to (d) due to the degeneracy of the genetic code; and
(f) a nucleic acid molecule hybridizing under stringent conditions with a nucleic acid molecule contained in DSM 22208, and encoding a polypeptide having serine protease activity and an amino acid sequence which shows at least 81% identity to the amino acid sequence as depicted in SEQ ID NO:18.

The invention further relates to a recombinant expression vector comprising the nucleotide sequence of the invention operably linked to regulatory sequences capable of directing expression of said serine protease encoding gene in a suitable host. Suitable hosts include heterologous hosts, preferably microbial hosts of the genus *Trichoderma, Aspergillus, Fusarium, Humicola, Chrysosporium, Neurospora, Rhizopus, Penicillium* and *Mortiriella*. Preferably said enzyme is produced in *Trichoderma* or *Aspergillus*, most preferably in *T. reesei*.

The invention relates also to a host cell comprising the recombinant expression vector as described above. Preferably, the host cell is a microbial host, such as a filamentous fungus. Preferred hosts are of a genus *Trichoderma, Aspergillus, Fusarium, Humicola, Chrysosporium, Neurospora, Rhizopus, Penicillium* and *Mortiriella*. More preferably the host is *Trichoderma* or *Aspergillus*, most preferably a filamentous fungus *T. reesei*.

The present invention relates to a process of producing a polypeptide having serine protease activity, said process comprising the steps of culturing the host cell of the invention and recovering the polypeptide. Also within the invention is a polypeptide having serine protease activity encoded by the nucleic acid sequence of the invention and which is obtainable by the process described above.

The invention relates to a process for obtaining an enzyme preparation comprising the steps of culturing a host cell of the invention and either recovering the polypeptide from the cells or separating the cells from the culture medium and obtaining the supernatant. Within the invention is also an enzyme preparation obtainable by the process described above.

The invention relates to an enzyme preparation, which comprises the serine protease enzyme of the invention.

The enzyme preparation of the invention may further comprise other enzymes selected from the group of protease, amylase, cellulase, lipase, xylanase, mannanase, cutinase, pectinase or oxidase with or without a mediator as well as suitable additives selected from the group of stabilizers, buffers, surfactants, bleaching agents, mediators, anti-corrosion agents, builders, antiredeposition agents, optical brighteners, caustics, abrasives, dyes, pigments and preservatives, etc.

The spent culture medium of the production host can be used as such, or the host cells may be removed, and/or it may be concentrated, filtrated or fractionated. It may also be dried. The enzyme preparation of the invention may be in the form of liquid, powder or granulate.

Also within the invention is the use of the serine protease enzyme or the enzyme preparation of the invention for detergents, for treating fibers, for treating wool, for treating hair, for treating leather, for treating food or feed, or for any applications involving modification, degradation or removal of proteinaceous material. Particularly, the enzyme or enzyme preparation is useful as a detergent additive in detergent liquids and detergent powders.

BRIEF DESCRIPTION OF DRAWINGS

FIGS. 1A and 1B show the nucleotide sequence of the *Fusarium acuminatum* RF7182 Fa prtS8A gene (SEQ ID NO: 13) and the deduced amino acid sequence (SEQ ID NO: 14). The putative signal peptide (amino acid residues 1-20 of SEQ ID NO:14; nucleic acid residues 1-60 of SEQ ID NO:13), analyzed by SignalP V3.0 program is in lower case letters and underlined. The pro sequence (nucleic acid residues 61-309 and 361-429 of SEQ ID NO:13) and the deduced amino acids of the pro sequence (amino acid residues 21-126 of SEQ ID NO:14) are in lower case letters. The mature nucleotide (nucleic acid residues 430-1353 of SEQ ID NO:13) and peptide sequences (amino acid residues 127-415 of SEQ ID NO:14) are in capital letters (N-terminal sequence determined from the purified wild type Fa_RF7182 protein). The location of the putative intron sequence (nucleic acid residues 310-360 and 836-889 of SEQ ID NO:13) is in lower case, italic letters and marked by a dotted line below the nucleotide sequence. The stop codon is shown by an asterisk below the sequence. The N-terminal sequence and peptide sequences obtained from the wild type Fa_RF7182 protein are highlighted with gray background.

FIG. 1A shows the nucleotide sequence of the Fa prt8a gene (nucleotides 1 to 990), the sequence region encoding amino acids Met1 to Val278 of the Fa_RF7182 protein.

FIG. 1B shows the nucleotide sequence of the Fa prt8A gene (nucleotides 991 to 1353), the sequence region encoding amino acids Leu279 to Ala415 of the Fa_RF7182 protein.

FIG. 9A shows the performance with detergent concentration of 5 g/l and pH 7.5.

FIG. 9B shows the performance with detergent concentration of 5 g/l (enzyme dosage calculated as amount of protein).

FIG. 9C shows the performance with detergent concentration of 3.3 g/l and pH 7.4.

FIG. 9D shows the performance with detergent concentration of 1 g/l and pH 7.3.

FIG. 10A shows the performance with detergent concentration of 5 g/l and pH 8.

FIG. 10B shows the performance with detergent concentration of 5 g/l (enzyme dosage calculated as amount of protein).

FIG. 10C shows the performance with detergent concentration of 3.3 g/l and pH 7.9.

FIG. 10D shows the performance with detergent concentration of 1 g/l and pH 7.6.

FIG. 11A shows performance on blood/milk/ink/PE-cotton (Art. 117, EMPA).

FIG. 11B shows performance on blood/milk/ink/Cotton (Art. 116, EMPA).

FIG. 11C shows performance on grass (Art. 164, EMPA).

FIG. 11D shows performance on cocoa (Art. 112, EMPA).

FIGS. 12A and 12B describe total stain removal efficiency (delta % SR) of Fa_RF7182 enzyme preparation on eight different protease sensitive stains (Table 5) in full-scale washing trials. Commercial preparations Savinase® Ultra 16L and Purafect® 4000L were used for comparison.

FIG. 12A shows total stain removal efficiency when protease preparations were dosed according to the activity.

FIG. 12B shows total stain removal efficiency when protease preparations were dosed according to the amount of protein FIGS. 13A-E describe stain removal effect with liquid detergent base for colored fabrics in full scale trial at 30° C.

FIG. 14A shows the performance of recombinant protein Fa_RF7182 and commercial protease preparations at 10° C.

FIG. 14B shows the performance of recombinant protein Fa_RF7182 and commercial protease preparations at 20° C.

FIG. 14C shows the performance of recombinant protein Fa_RF7182 and commercial protease preparations at 30° C.

FIG. 14D shows the performance of recombinant protein Fa_RF7182 and commercial protease preparations at 40° C.

FIG. 14E shows the performance of recombinant protein Fa_RF7182 and commercial protease preparations at 50° C.

FIG. 14F shows the performance of recombinant protein Fa_RF7182 and commercial protease preparations at 60° C.

FIG. 15A Shows performance at 10° C.

FIG. 15B Shows performance at 20° C.

SEQUENCE LISTING

Figure 2:
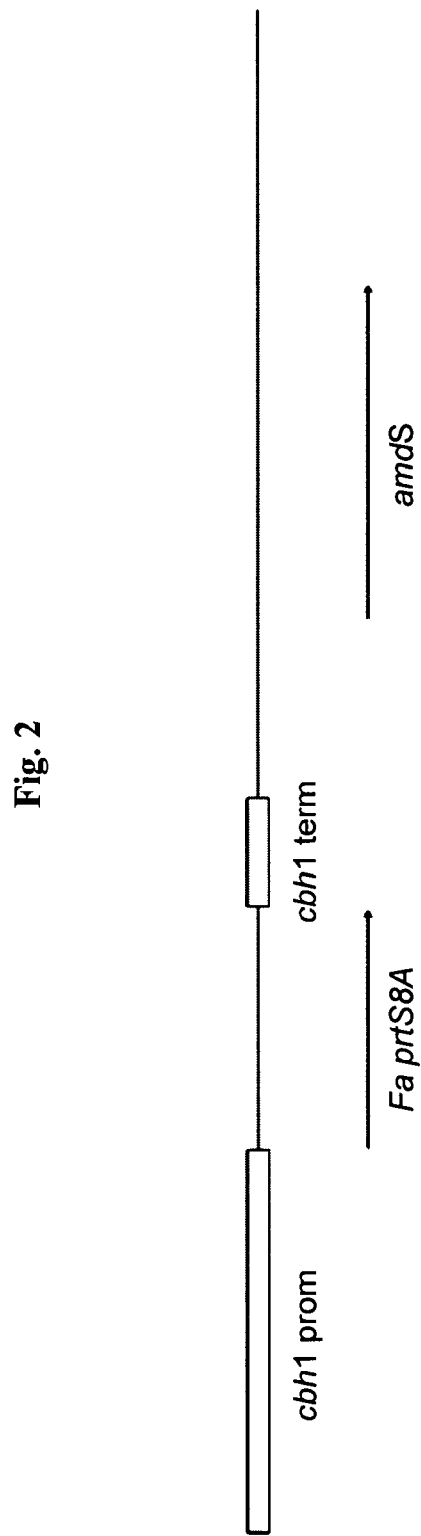
FIG. 2 schematically shows the cassette used for expressing the Fa prtS8A gene in *Trichoderma reesei*.

SEQ ID NO:1 Sequence of an amino terminal peptide #3811 from *Fusarium acuminatum* RF7182 protease.

SEQ ID NO:2 Sequence of a tryptic peptide 1609,880 from *Fusarium acuminatum* RF7182 protease.

SEQ ID NO:3 Sequence of a tryptic peptide 1793,957 from *Fusarium acuminatum* RF7182 protease.

SEQ ID NO:4 Sequence of a tryptic peptide 743,494 from *Fusarium acuminatum* RF7182 protease.

SEQ ID NO:5 Sequence of a tryptic peptide 2103,832 (start 2045,06) from *Fusarium acuminatum* RF7182 protease.

SEQ ID NO:6 Sequence of a tryptic peptide 2103,832 (start 1406,57) from *Fusarium acuminatum* RF7182 protease.

SEQ ID NO:7 Sequence of a tryptic peptide 3662,692 from *Fusarium acuminatum* RF7182 protease.

SEQ ID NO:8 The sequence of the oligonucleotide primer PRO123 derived from the peptide SEQ ID NO:3.

SEQ ID NO:9 The sequence of the oligonucleotide primer PRO122 derived from the peptide SEQ ID NO:6.

SEQ ID NO:10 The sequence of the serine protease consensus oligonucleotide primer PRO60.

SEQ ID NO:11 The sequence of the serine protease consensus oligonucleotide primer PRO61.

SEQ ID NO:12 The sequence of the PCR fragment obtained using the primers PRO123 (SEQ ID NO:8) and PRO61 (SEQ ID NO:11) and *Fusarium acuminatum* RF7182 genomic DNA as a template.

SEQ ID NO:13 The nucleotide sequence of the full-length *Fusarium acuminatum* RF7182 protease gene (Fa prtS8A).

SEQ ID NO:14 The deduced amino acid sequence of the full-length *Fusarium acuminatum* RF7182 protease (Fa_RF7182) including amino acids Met 1 to Ala415.

SEQ ID NO:15 The nucleotide sequence encoding the amino acid sequence of the proenzyme form of *Fusarium acuminatum* RF7182 protease.

SEQ ID NO:16 The amino acid sequence of the proenzyme form of *Fusarium acuminatum* RF7182 protease, including amino acids Ala21 to Ala415 of the full-length Fa_RF7182 defined in SEQ ID No:14.

SEQ ID NO:17 The nucleotide sequence encoding the amino acid sequence of the mature form of *Fusarium acuminatum* RF7182 protease.

SEQ ID NO:18 The amino acid sequence of the mature form of *Fusarium acuminatum* RF7182 protease, including amino acids Ala127 to Ala415 of the full-length Fa_RF7182 defined in SEQ ID No:14.

Depositions

*Fusarium acuminatum* RF7182 was deposited at the Centraalbureau Voor Schimmelcultures at Uppsalalaan 8, 3508 AD, Utrecht, the Netherlands on 28 Jan. 2009 and assigned accession number CBS 124084.

The *E. coli* strain RF7803 including the plasmid pALK2530 was deposited at the Deutsche Sammlung von Mikroorganismen und Zellkulturen GmbH (DSMZ), Inhoffenstrasse 7 b, D-38124 Braunschweig, Germany on 21 Jan. 2009 and assigned accession number DSM 22208.

The *E. coli* strain RF7879 including the plasmid pALK2531 was deposited at the Deutsche Sammlung von Mikroorganismen und Zellkulturen GmbH (DSMZ), Inhoffenstrasse 7 b, D-38124 Braunschweig, Germany on 21 Jan. 2009 and assigned accession number DSM 22209.

DETAILED DESCRIPTION

The present invention provides a serine protease of fungal origin, which protease shows broad substrate specificity, is stable at high pH ranges and has a broad temperature optimum, i.e. good performance both at low and moderate temperatures. The enzyme is ideal for detergent applications, withstanding oxidizing and chelating agents and being effective at low enzyme levels in detergent solutions. Particularly, the serine protease is active at temperatures as low as 10° C., the preferred range being from 10° C. to 70° C. Thus, the present invention provides an alternative serine protease for use in detergent and other applications. The fungal serine protease can be produced in high-yielding fungal hosts and its down-stream processing, e.g. separation of fermentation broth and mycelia is easy to perform.

By "serine protease" or "serine endopeptidase" or "serine endoproteinase" is in connection to this invention meant an enzyme classified as EC 3.4.21 by the Nomenclature of the International Union of Biochemistry and Molecular Biology. Serine proteases are found in both single-cell and complex organisms. Based on their structural similarities, serine proteases have been grouped into at least six clans (SA, SB, SC, SE, SF and SG; S denoting serine protease), which have been further subgrouped into families with similar amino acid sequences and three-dimensional structures (see, for example the Serine protease home page at biochem.wustl.edu/~protease/, Department of Biochemistry and Molecular Biophysics, Washington University of Medicine, St. Louis, Mo., USA). These protein hydrolyzing or degrading enzymes are characterized by the presence of a nucleophilic serine group in their active site, and the proteases of clan SA and clan SB are also distinguished by having essential aspartate and histidine residues, which along with the serine, form a catalytic triad.

The major clans include the "chymotrypsin-like", including chymotrypsin, trypsin and elastase (clan SA) and "subtilisins-like" (clan SB) serine proteases. The enzymes target different regions of the polypeptide chain, based upon the side chains of the amino acid residues surrounding the site of cleavage. The serine protease of the present invention belongs to clan SB.

The characterized "subtilisin-like serine proteases" or "subtilases" are generally bacterial in origin. This class of proteases, represented by various *Bacillus*, like *B. amyloliquifaciens*, *B. licheniformis* and *B. subtilis* (Rao et al., 1998), is specific for aromatic or hydrophobic residues, such as tyrosine, phenylalanine and leucine.

By the term "serine protease activity" as used in the invention is meant hydrolytic activity on protein containing substrates, e.g. such as casein, haemoglobin, keratin and BSA. The methods for analysing proteolytic activity are well-known in the literature and are referred e.g. in Gupta et al. (2002).

Proteases can be classified using group specific inhibitors. The diverse group of "serine protease inhibitors", includes synthetic chemical inhibitors and natural proteinaceous inhibitors. One group of natural inhibitors are serpins (abbreviated from serine protease inhibitors), such as antithrombin and alpha 1-antitrypsin. Artificial synthetic inhibitors include 3,4-dichloroisocoumarin (3,4-DCI), diisopropylfluorophosphate (DFP), phenylmethylsulfonyl fluoride (PMSF) and tosyl-L-lysine chloromethyl ketone (TLCK). Some of the serine proteases are inhibited by thiol reagents such as p-chloromercuribenzoate (PCMB) due to the presence of a cysteine residue near the active site. Thus, the serine protease activity can be determined in an assay based on cleavage of a specific substrate or in an assay using any protein containing substrate with or without a specific inhibitor of serine proteases under suitable conditions.

Serine proteases are generally active at neutral or alkaline pH, with an optimum between pH 7 and 11, and have broad substrate specificity. The "alkaline serine proteases" mean enzymes that are active and stable at pH 9 to pH 11 or even at pH 10 to 12.5 (Shimogaki et al., 1991) and have isoelectric point around pH 9. Those represent the largest subgroup of commercial serine proteases. The molecular masses of alkaline serine proteases range between 15 and 35 kDa. The temperature optima of the natural serine proteases are around 60° C. (Rao et al., 1998).

Microorganism strains capable of producing protease activity can be screened and the activity on different substrates can be determined. Chosen strains can be cultivated on a suitable medium. After a sufficient amount of an interesting serine protease has been produced, the enzyme can be isolated or purified and its properties can be more thoroughly characterized. Alternatively, genes encoding serine proteases in various organisms can be isolated and the amino acid sequence encoded by the genes can be compared with the amino acid sequences of the serine protease isolated and characterized in the Examples here.

The produced protease enzymes, particularly the serine proteases can be purified by using conventional methods of enzyme chemistry, such as salt preparation, ultrafiltration, ion exchange chromatography, affinity chromatography, gel filtration and hydrophobic interaction chromatography. Purification can be monitored by protein determination, enzyme activity assays and by SDS polyacrylamide gel electrophoresis. The enzyme activity and stability of the purified enzyme at various temperature and pH values as well as the molecular mass and the isoelectric point can be determined.

The purification of a preferred serine protease of the present invention has been demonstrated in Example 1b. The filtrated culture supernatant was applied to a Q Sepharose FF column. The flow through fraction was applied to phenyl Sepharose HP column and proteins were eluted with a linear decreasing salt gradient. Fractions showing protease activity were pooled, concentrated and applied to a Superdex 75 10/300 GL column. Purification was followed by activity assays on resorufin-labeled casein as described in Example 1b. Naturally, it is possible to separate the enzyme of the present invention by using other known purification methods instead, or in addition to the methods described herein. The recombinant serine protease was purified as described in Example 5 and used for characterization of pH and temperature profiles.

The molecular mass of the purified serine protease can be determined by mass spectrometry or on SDS-PAGE according to Laemmli (1970). The molecular mass can also be predicted from the amino acid sequence of the enzyme. The mature serine protease or mature serine protease enzyme typically has a molecular mass between 20 to 35 kDa, typically around 25 to 30 kDa (Rao et al., 1998).

The serine proteases are synthesized as inactive "zymogenic precursors" or "zymogens" in the form of a preproenzyme, which are activated by removal of the signal sequence (secretion signal peptide or prepeptide) and the prosequence (propeptide) to yield an active mature form of the enzyme (Chen and Inouye, 2008). This activation process involves action of proteases and may result from limited self-digestive or autocatalytic processing of the serine protease. The prosequence may be cleaved for example during posttranslational phases of the production or in the spent culture medium or during the storage of the culture medium or enzyme preparation. Activation of the proenzyme may also be achieved by adding a proteolytic enzyme capable of converting the inactive proenzyme into active mature enzyme into the culture medium where the host organism is cultivated or adding the proteolytic enzyme to the culture supernatant after cultivation process. The shortening of the enzyme can also be achieved e.g. by truncating the gene encoding the polypeptide prior to transforming it to the production host.

The term "mature" means the form of enzyme which after removal of the signal sequence and propeptide comprises the essential amino acids for enzymatic or catalytic activity. In filamentous fungi it is the native form secreted into the culture medium.

The temperature optimum of the serine protease can be determined in a suitable buffer at different temperatures by using casein as a substrate as described in Example 1c and 5 or by using other substrates and buffer systems described in the literature (Gupta et al., 2002). Determination of the pH optimum can be carried out in a suitable buffer at different pH values by following the activity on a protein substrate.

Protease activity is generally based on degradation of soluble substrates. In detergent application proteases have to work on substances which are at least partly insoluble. Thus an important parameter for a detergent protease is its the ability to adsorb to and hydrolyse these insoluble fragments.

Another important parameter for selection of detergent proteases is its isoelectric point or pI value. The detergent proteases perform best when the pH value of the detergent solution in which it works is approximately the same as the pI value for the enzyme. The pH in the detergent application is usually alkaline, pH 7-9 for liquid detergents and pH 9-10.5 when powder detergents are used. pI can be determined by isoelectric focusing on an immobilized pH gradient gel composed of polyacrylamide, starch or agarose or by estimating the pI from the amino acid sequence, for example by using the pI/MW tool at ExPASy server (expasy.org/tools/pi_tool.html; Gasteiger et al., 2003).

The N-terminus of the purified protease as well as internal peptides can be sequenced according to Edman degradation chemistry (Edman and Begg, 1967) as described in Example 2 or by other methods described in the literature.

The serine protease enzyme of the invention may derive from any organism including bacteria, archaea, fungi, yeasts and even higher eukaryote, such as plants. Preferably said enzyme originates from a fungus, including filamentous fungi and yeasts, for example from a genus selected from the group comprising *Fusarium*. Fungal alkaline proteases are advantageous to the bacterial proteases due to the ease of down-stream processing to produce a microbe-free enzyme or enzyme composition. Mycelium can be easily removed through filtration techniques prior to the purification of the enzyme.

The present invention relates to fungal serine protease, which has a good performance in the presence of detergents with highly varying properties, at broad, i.e. from low to moderate temperature ranges, such as 10° C. to 60° C.

In the present invention good performance in presence of detergent means that the enzyme, in this case the fungal serine protease of the invention, functions at lower temperature ranges than many commercial subtilisins presently for sale. In other words, good performance means that the enzyme is capable of degrading or removing proteinaceous stains or material at low to moderate temperature ranges, but especially at lower temperature ranges than the present commercial products, for example the commercial enzyme product Purafect® 4000L (Genencor Inc., USA).

The fungal serine protease of the invention functions at low temperature ranges. For example, by modifying pH, selecting detergents with suitable properties, including enzyme protecting agents and by controlling washing conditions the activity of the serine protease of the invention may be maintained at temperatures as low as 10° C. Therefore, the serine protease of the invention depending on the washing conditions and auxiliary ingredients and additives in detergents is useful particularly in temperatures at or below 50° C. The enzyme functions also at temperatures at or below 45° C., at or below 40° C., at or below 35° C., or at or below 30° C.

In the presence of a detergent, the fungal serine protease of the invention functions as defined above between 10° C. and 60° C. In Examples 6 to 13, comparative experiments are described, and from FIGS. 7 to 15 it is evident that the performance of the fungal serine protease Fa_RF7182 in varying conditions and exposed to varying treatments, on multitude of different stains on different textile material, measured as deltaL* or Sum of delta % SR, is by far better than the performance of the commercial products, Savinase® Ultra 16L (Novozymes A/S, DK), Purafect® 4000L (Genencor Inc, USA) and Properase® 4000E (Genencor Inc., USA). Particularly, the stain removal effect of said fungal serine protease Fa_RF7182 in low temperature ranges such as from 10° C. to 40° C. is remarkably higher than with Savinase® Ultra 16L, Properase® 4000E and Purafect® 4000L.

From said experimental results it can be concluded that the fungal serine protease of the invention is capable of satisfying the greatly varying demands of detergent customers and detergent industry and industry providing washing machinery and is well suited to the requirements of future regulations and customer habits.

According to a preferred embodiment of the invention the fungal serine protease enzyme is a polypeptide having serine protease activity and comprising the mature enzyme of Fa_RF7182 having the amino acid sequence of SEQ ID NO:18 or an amino acid sequence having at least 81% identity to the amino acid sequence SEQ ID NO:18 or at least 80% to the amino acid sequence SEQ ID NO:14. Preferred enzymes show at least 81%, preferably at least 83%, more preferably at least 85%, even more preferably at least 87% identity. Still more preferably the amino acid sequences show at least 89% or at least 91%, 92%, 93%, 95% or 97%, more preferably at least 98%, most preferably 99% identity to the amino acid sequence of SEQ ID NO:18. The identities of the two enzymes are compared within the corresponding sequence regions, e.g. within the full-length or mature region of the serine protease.

The serine protease of the present invention is marked Fa_RF7182, an isolated serine protease originating from *Fusarium acuminatum* and is a member of clan SB, family 8 of serine endoproteinases.

By the term "identity" is here meant the identity between two amino acid sequences compared to each other within the corresponding sequence region having approximately the same amount of amino acids. For example, the identity of a full-length or a mature sequence of the two amino acid sequences may be compared. The amino acid sequences of the two molecules to be compared may differ in one or more positions, which however does not alter the biological function or structure of the molecules. Such variation may occur naturally because of different host organisms or mutations in the amino acid sequence or they may be achieved by specific mutagenesis. The variation may result from deletion, substitution, insertion, addition or combination of one or more positions in the amino acid sequence. The identity of the sequences is measured by using ClustalW alignment (e.g. in ebi.ac.uk/Tools/Clustalw). The matrix used is as follows: BLOSUM, Gap open: 10, Gap extension: 0.5.

Preferably, the fungal serine protease is obtainable from *Fusarium*, more preferably from *Fusarium acuminatum*. According to the most preferred embodiment the serine protease of the invention is obtainable from the strain deposited at Centraalbureau voor Schimmelcultures under accession number CBS 124084.

One preferred embodiment of the invention is a fungal serine protease enzyme having serine protease activity and an amino acid sequence of the mature Fa_RF7182 enzyme as defined in SEQ ID NO:18. The mature enzyme lacks the signal sequence or prepeptide and the prosequence or propeptide. The mature serine protease of the invention includes amino acids Ala127 to Ala415 of the full length protease characterized in SEQ ID NO:13. Thus, within the scope of the invention is also the full-length Fa_RF7182 enzyme having SEQ ID NO:13 including the signal sequence (prepeptide) and propeptide and the mature enzyme as well as the proenzyme form lacking the signal sequence (prepeptide) thus having SEQ ID NO:15.

The present invention relates to a fungal serine protease enzyme, the mature form of which has a molecular mass or molecular weight between 20 and 35 kDa, preferably between 25 and 33 kDa, more preferably between 28 and 30 kDa. The most preferred MW is the predicted molecular mass of Fa_RF7182 being 29 kDa for the mature polypeptide obtained by using the Compute pI/MW tool at ExPASy server (Gasteiger et al., 2003).

The enzyme of the invention is effective in degrading proteinaceous material at a broad temperature range. The optimal temperature of the enzyme is from 30° C. to 70° C. (about 10% of the maximum activity), preferably from 30° C. to 60° C. (approximately 30% of the maximum activity), and more preferably between 40° C. and 50° C. (at least 60% of the maximum activity), most preferably at 50° C. (the maximum activity, Fa_RF7182) when measured at pH 9 using 15 min reaction time and casein as a substrate as described in Example 5.

According to one preferred embodiment of the invention the fungal serine protease enzyme has pH optimum at pH range from at least pH 6 to pH 12, showing at least 10% of the maximum activity at pH 7 at 50° C. using 15 min reaction time as described in Example 5. Preferably, the enzyme has pH optimum at pH range of pH 6 to pH 11 (at least 40% of the maximum activity). In particular, the pH optimum is between pH 6 and pH 10 (approximately 55% of the maximum activity), and more preferably between pH 6 and pH 9 (at least 80% of the maximum activity), and most preferably at pH 7 at 50° C. using 15 min reaction time as described in Example 5 when using casein as a substrate.

The fungal serine protease of the invention has "good performance in the presence of detergent", i.e. is capable of degrading or removing proteinaceous stains on colored materials in the presence of detergent at low temperature ranges, specifically at lower temperature ranges than the present commercial products, for example the commercial enzyme product Purafect® 4000L (Genencor Inc., USA). In the presence of a detergent the enzyme of the invention functions between 10° C. and 60° C., preferably between 20° C. and 50° C., more preferably at or below 50° C. The Fa_RF7182 enzyme functions also at temperatures at or below 45° C., at or below 40° C., at or below 35° C., or at or below 30° C.

The serine protease enzyme of the invention has pI, which as predicted from the deduced amino acid sequence is between pI 8.8 and pI 9.5, preferably between pI 8.9 and pI 9.3. The predicted pI of Fa_RF7182 enzyme of the invention is pI 9.1.

Oligonucleotides synthesized on the amino acid sequence of N-terminal or tryptic peptides of the purified enzyme or a PCR product obtained by using the above oligonucleotides can be used as probes in isolation of cDNA or a genomic gene encoding the serine protease of the invention. The probe may be designed also based on the known nucleotide or amino acid sequences of homologous serine proteases. The serine protease clones may also be screened based on activity on plates containing a specific substrate for the enzyme or by using antibodies specific for a serine protease.

According to a preferred embodiment of the invention the fungal serine protease enzyme is encoded by an isolated polynucleotide sequence which hybridizes under stringent conditions with a polynucleotide or probe sequence included in plasmid pALK2530 comprising the nucleotide sequence SEQ ID NO:12 in *E. coli* RF7803, deposited at the Deutsche Sammlung von Mikroorganismen and Zellkulturen (DSMZ) under accession number DSM 22208.

In the present invention the Fa prt8A gene was isolated with a probe prepared by PCR using stringent hybridization as described in Example 3d. Standard molecular biology methods can be used in isolation of cDNA or a genomic DNA of the host organism, e.g. the methods described in the molecular biology handbooks, such as Sambrook and Russell, 2001.

Hybridization with a DNA probe, such as for example SEQ ID NO:12 consisting of more than 100-200 nucleotides, is usually performed at "high stringency" conditions, i.e. hybridization at a temperature, which is 20-25° C. below the calculated melting temperature (Tm) of a perfect hybrid, the Tm calculated according to Bolton and McCarthy (1962). Usually prehybridization and hybridization are performed at least at 65° C. in 6×SSC (or 6×SSPE), 5×Denhardt's reagent, 0.5% (w/v) SDS, 100 μg/ml denatured, fragmented salmon sperm DNA. Addition of 50% formamide lowers the prehybridization and hybridization temperatures to 42° C. Washes are performed in low salt concentration, e.g. in 2×SSC-0.5% SDS (w/v) for 15 minutes at room temperature (RT), followed in 2×SSC-0.1% SDS (w/v) at RT, and finally in 0.1×SSC-0.1% SDS (w/v) at least at 65° C.

According to one preferred embodiment the fungal serine protease enzyme of the invention is encoded by an isolated nucleic acid molecule, which encodes a polypeptide comprising the amino acid sequence characterized in SEQ ID NO:18, or a polypeptide having at least 81% to the amino acid sequence SEQ ID NO:18 or at least 80% to the amino acid sequence SEQ ID NO:13. Preferred enzymes show at least 81%, preferably at least 83%, more preferably at least 85%, even more preferably at least 87% identity. Still more preferably the amino acid sequences show at least 89%, 91%, 93% or at least 97%, more preferably at least 98%, most preferably 99% identity to the amino acid sequence of SEQ ID NO:18. The identities of the two enzymes are compared within the corresponding sequence regions, e.g. within the mature or full-length region of the serine protease.

Thus, within the scope of the invention is a polypeptide sequence, which is encoded by a nucleic acid molecule encoding the amino acid sequence of the full-length serine protease of the invention including the prepeptide (signal sequence) and the propeptide in addition to the mature form of the enzyme, and which amino acid sequence is characterized in SEQ ID NO:14.

Also, within the scope of the invention is a polypeptide sequence, which is encoded by a nucleic acid molecule encoding the proenzyme form of serine protease enzyme of the invention including the propeptide in addition to the mature form of the enzyme, and which amino acid sequence is characterized in SEQ ID NO:16.

One preferred embodiment of the invention is the fungal serine protease enzyme encoded by an isolated nucleic acid molecule, which comprises the nucleotide sequence encoding the mature form of the Fa_RF7182 serine protease having SEQ ID NO:18.

According to one preferred embodiment the fungal serine protease enzyme of the invention is encoded by an isolated nucleic acid molecule comprising the nucleotide sequence SEQ ID NO:17 encoding the mature form of the Fa_RF7182 enzyme (SEQ ID NO:18).

Thus, within the scope of the invention is the polypeptide encoded by the nucleic acid molecule having the nucleotide sequence SEQ ID NO:13 comprising the "coding sequence" for the enzyme. The expression "coding sequence" means the nucleotide sequence which initiates from the translation start codon (ATG) and stops at the translation stop codon (TAA, TAG or TGA). The translated full-length polypeptide starts usually with methionine and comprises intron regions.

Also, within the scope of the invention is a fungal serine protease enzyme encoded by a nucleic acid molecule comprising the nucleotide sequence SEQ ID NO:15, which encodes the Fa_RF7182 proenzyme form.

According to another preferred embodiment of the invention the fungal serine protease is encoded by the polynucleotide sequence included in pALK2531 deposited in *E. coli* RF7879 under accession number DSM 22209.

One embodiment of the invention is the serine protease enzyme produced from a recombinant expression vector comprising the nucleic acid molecule, which encodes the fungal serine protease enzyme as characterized above operably linked to regulatory sequences capable of directing the expression of said serine protease encoding gene in a suitable host. Construction of said recombinant expression vector and use of said vector is described in more detail in Example 4.

Suitable hosts for production of the fungal serine protease enzyme are homologous or heterologous hosts, such as the microbial hosts including bacteria, yeasts and fungi. Filamentous fungi, such as *Trichoderma, Aspergillus, Fusarium, Humicola, Chrysosporium Neurospora, Rhizopus, Penicillium* and *Mortiriella* are preferred production hosts due to the ease of down-stream processing and recovery of the enzyme product. Suitable hosts include species such as *T. reesei, A. niger, A oryzae, A. sojae, A. awamori* or *A. japonicus* type of strains, *F. venenatum* or *F. oxysporum, H. insolens* or *H. lanuginosa, N. crassa* and *C. lucknowense*, some of which are listed as enzyme production host organisms in e.g. AMFEP 2007 list of commercial enzymes (http://www.amfep.org/list.html). More preferably, the enzyme is produced in a filamentous fungal host of the genus *Trichoderma* or *Aspergillus*, such as *T. reesei*, or *A. niger, A. oryzae* or *A. awamori* strains. According the most preferred embodiment of the invention the fungal serine protease enzyme is produced in *T. reesei*.

The present invention relates also to an isolated nucleic acid molecule encoding the fungal serine protease enzyme selected from the group consisting of:
 (a) a nucleic acid molecule encoding a polypeptide having serine protease activity and comprising the amino acid sequence as depicted in SEQ ID NO:18;
 (b) a nucleic acid molecule encoding a polypeptide having serine protease activity and at least 81% to SEQ ID NO:18;
 (c) a nucleic acid molecule comprising the coding sequence of the nucleotide sequence as depicted in SEQ ID NO: 13;
 (d) a nucleic acid molecule comprising the coding sequence of the polynucleotide sequence contained in DSM 22208 or DSM 22209;
 (e) a nucleic acid molecule the coding sequence of which differs from the coding sequence of a nucleic acid molecule of any one of (c) to (d) due to the degeneracy of the genetic code; and
  (f) a nucleic acid molecule hybridizing under stringent conditions with a nucleic acid molecule contained in DSM 22208, and encoding a polypeptide having serine protease activity and an amino acid sequence which shows at least 81% identity to the amino acid sequence as depicted in SEQ ID NO:18.

The nucleic acid molecule of the invention may be RNA or DNA, wherein the DNA may constitute of the genomic DNA or cDNA.

Standard molecular biology methods can be used in isolation and enzyme treatments of the polynucleotide sequence encoding the fungal serine protease of the invention, including isolation of genomic and plasmid DNA, digestion of DNA to produce DNA fragments, sequencing, *E. coli* transformations etc. The basic methods are described in the standard molecular biology handbooks, e.g. Sambrook and Russell, 2001.

Isolation of the Fa prtS8A gene encoding the Fa_RF7182 polypeptide is described in Example 3. Briefly, the 753 bp PCR fragment obtained by using the sequences of the degenerate oligonucleotide primers PRO123 (SEQ ID NO: 8) and PRO61 (SEQ ID NO:11) was used to isolate the Fa prt8A gene from *Fusarium acuminatum* RF7182 in pBluescript 11 KS+ vector. The full-length *Fusarium acuminatum* Fa prtS8A gene was included in the plasmid pALK2531 deposited in *E. coli* to the DSMZ culture collection under accession number DSM 22209. The deduced amino acid sequence of the serine protease was analysed from the DNA sequence.

The nucleotide sequence of *Fusarium acuminatum* serine protease Fa prtS8A nucleotide sequence (SEQ ID NO: 13) and the deduced sequence (SEQ ID NO: 14) are presented in FIGS. 1A and 1B. The length of the gene is 1353 bp (including the stop codon). Two putative introns were found having the length of 51 bps and 54 bps. The deduced protein sequence consists of 415 amino acids including a predicted signal sequence of 20 amino acids (SignalP V3.0; Nielsen et al., 1997 and Nielsen and Krogh, 1998) and a propeptide from Ala21 to Arg 126. The predicted molecular mass was 29 kDa for the mature polypeptide and the predicted pI was 9.1. These predictions were made using the Compute pI/MW tool at ExPASy server (Gasteiger et al., 2003). The deduced amino acid sequence contained two possible N-glycosylation sites (Asn79 and Asn258), but according to CBS Server NetNGlyc V1.0 only the site at position Asn79 (located in the propeptide) is probable. The homologies to the published protease sequences were searched using the BLASTX program, version 2.2.9 at NCBI (National Center for Biotechnology Information) (Altschul et al., 1990). The identity values of the mature Fa_RF7182 sequence to the corresponding mature regions of homologous sequences were obtained by using ClustalW alignment (Matrix: BLOSUM, Gap open: 10, Gap extension: 0.5 (e.g. in ebi.ac.uk/Tools/Clustalw) and are shown in Table 3.

The serine protease Fa-RF7182 of the present invention showed highest homology to *Gibberella zeae* (*Fusarium graminearum*) hypothetical protein PH-1, locus tag FG03315.1 (EMBL accession no. XP-383491, unpublished), to *Hypocrea lixii* (*Trichoderma harzianum*) CECT 2413 serine endopeptidase (EMBL accession no. CAL25580, Suarez et al., 2007) and to *T. atroviride* alkaline proteinase precursor S08.066, ALP (EMBL accession no. M87516, Geremia et al. 1993), the latter disclosed as an amino acid sequence SEQ ID NO:313 in U.S. 60/818,910 (Catalyst Bioscience Inc.). The identity to *G. zeae* hypothetical protein was within the full-length enzyme 79%. When the mature polypeptides lacking the signal sequence and propeptide were aligned, the identity was 80%. Identity to *H. lixii* CECT 2413 serine endopeptidase was 73% (full-length enzyme) and 79% (mature enzyme). The identity to *T. atroviride* ALP was 71% (full-length enzyme) and 76% (mature enzyme).

Thus, within the scope of the invention is an isolated polynucleotide sequence or isolated nucleic acid molecule, which encodes a fungal serine protease enzyme or polypeptide comprising the amino acid sequence of the mature form of the Fa_RF7182 enzyme characterized in SEQ ID NO: 18, i.e. amino acids Ala127 to Ala415 of the full length serine protease of SEQ ID NO:14.

Further, within the scope of the present invention are nucleic acid molecules which encode a fragment of a fungal serine protease polypeptide, wherein the fragment has serine protease activity and has at least 81% identity to the amino acid sequence SEQ ID NO:18 or at least 80% to the amino acid sequence SEQ ID NO:14. Preferred enzymes show at least 81%, preferably at least 83%, more preferably at least 85%, even more preferably at least 87% identity. Still more preferably the amino acid sequences show at least 89% or at least 91%, 92%, 93%, 95% or 97%, more preferably at least 98%, most preferably 99% identity to the amino acid sequence of SEQ ID NO:18. The identities of the two enzymes are compared within the corresponding sequence regions, e.g. within the mature or full-length region of the serine protease.

The nucleic acid molecule is preferably a molecule comprising the coding sequence as depicted in SEQ ID NO:13, which encodes the full length form of the fungal serine protease enzyme of this invention.

The isolated nucleic acid molecule of the invention may be a molecule comprising the coding sequence of the polynucleotide sequence contained in DSM 22208 or DSM 22209. DSM 22208 carries the nucleotide sequence of the PCR fragment (SEQ ID NO:12) used in cloning the full length Fa prtS8A gene. DSM 22209 carries the nucleotide sequence of the full length Fa prtS8A gene (SEQ ID NO:13).

The nucleic acid molecule of the invention may also be an analogue of the nucleotide sequence characterized in above. The "degeneracy" means analogues of the nucleotide sequence, which differ in one or more nucleotides or codons, but which encode the recombinant protease of the invention.

The nucleic acid molecule may also be a nucleic acid molecule hybridizing under stringent conditions to a PCR probe contained in plasmid pALK2530 deposited in *E. coli* under the accession number DSM 22208 and encoding a polypeptide having serine protease activity and an amino acid sequence which within the corresponding sequence region shows at least 81% identity to the amino acid sequence as depicted in SEQ ID NO:18. The hybridizing DNA may originate from a fungus belonging to species *Fusarium* or it may originate from other fungal species.

Thus, within the scope of the invention is an isolated nucleic acid molecule comprising a nucleotide sequence as depicted in SEQ ID NO:12, SEQ ID NO:13, SEQ ID NO:15 or SEQ ID NO:17 and analogues thereof.

The present invention relates also to a recombinant expression vector or recombinant expression construct, which can be used to propagate or express the nucleic acid sequence encoding the chosen serine protease in a suitable prokaryotic or eukaryotic host. The recombinant expression vector comprises DNA or nucleic acid sequences which facilitate or direct expression and secretion of the serine protease encoding sequence in a suitable host, such as promoters, enhancers, terminators (including transcription and translation termination signals) and signal sequences operably linked the polynucleotide sequence encoding said serine protease. The expression vector may further comprise marker genes for selection of the transformant strains or the selection marker may be introduced to the host in another vector construct by co-transformation. Said regulatory sequences may be homologous or heterologous to the production organism or they may originate from the organism, from which the gene encoding the serine protease is isolated.

Examples of promoters for expressing the serine protease of the invention in filamentous fungal hosts are the promoters of *A. oryzae* TAKA amylase, alkaline protease ALP and triose phosphate isomerase, *Rhizopus miehei* lipase, *Aspergillus niger* or *A. awamori* glucoamylase (glaA), *Fusarium oxysporum* trypsin-like protease, *Chrysosporium lucknowense* cellobiohydrolase I promoter, *Trichoderma reesei* cellobiohydrolase I (Cel7A) etc.

In yeast, for example promoters of *S. cerevisiae* enolase (ENO-1), galactokinase (GAL1), alcohol dehydrogenase (ADH2) and 3-phosphoglycerate kinase can be used to provide expression.

Examples of promoter sequences for directing the transcription of the serine protease of the invention in a bacterial host are the promoter of lac operon of *Escherichia coli*, the *Streptomyces coelicolor* agarase dagA promoter, the promoter of the *B. licheniformis* alpha-amylase gene (amyL), the promoter of the *B. stearothermophilus* maltogenic amylase gene (amyM), the promoters of the B. sublitis xylA and xylB genes, etc.

Suitable terminators include those of the above mentioned genes or any other characterized terminator sequences.

Suitable transformation or selection markers include those which complement a defect in the host, for example the dal genes from *B. subtilis* or *B. licheniformis* or *Aspergillus* amdS and niaD. The selection may be based also on a marker conferring antibiotic resistance, such as ampicillin, kanamycin, chloramphenicol, tetracycline, phleomycin or hygromycin resistance.

Extracellular secretion of the serine protease of the invention is preferable. Thus, the recombinant vector comprises sequences facilitating secretion in the selected host. The signal sequence of the serine protease of the invention or the presequence or prepeptide may be included in the recombinant expression vector or the natural signal sequence may be replaced with another signal sequence capable of facilitating secretion in the selected host. Thus, the chosen signal sequence may be homologous or heterologous to the expression host.

Examples of suitable signal sequences are those of the fungal or yeast organisms, e.g. signal sequences from well expressed genes, well known in art.

The recombinant vector may further comprise sequences facilitating integration of the vector into the host chromosomal DNA to obtain stable expression.

The Fa_RF7182 protease of the invention was expressed with its own signal sequence from the *T. reesei* cbh1 (cel7A) promoter as described in Example 4. The expression construct used to transform the *T. reesei* host included also cbh1 terminator and amdS marker for selecting the transformants from the untransformed cells.

The present invention relates also to host cells comprising the recombinant expression vector as described above. Suitable hosts for production of the fungal serine protease enzyme are homologous or heterologous hosts, such as the microbial hosts including bacteria, yeasts and fungi. Production systems in plant or mammalian cells are also possible.

Filamentous fungi, such *Trichoderma, Aspergillus, Fusarium, Humicola, Chrysosporium, Neurospora, Rhizopus, Penicillium* and *Mortiriella*, are preferred production hosts due to the ease of down-stream processing and recovery of the enzyme product. Suitable expression and production host systems are for example the production system developed for the filamentous fungus host *Trichoderma reesei* (EP 244234), or *Aspergillus* production systems, such as *A. oryzae* or *A. niger* (WO 9708325, U.S. Pat. No. 5,843,745, U.S. Pat. No. 5,770,418), *A. awamori, A. sojae* and *A. japonicus*-type strains, or the production system developed for *Fusarium*, such as *F. oxysporum* (Malardier et al., 1989) or *F. venenatum*, and for *Neurospora. crassa, Rhizopus miehei, Mortiriella alpinis, H. lanuginosa* or *H. insolens* or for *Chrysosporium lucknowensee* (U.S. Pat. No. 6,573,086). Suitable production systems developed for yeasts are systems developed for *Saccharomyces, Schizosaccharomyces* or *Pichia pastoris*. Suitable production systems developed for bacteria are a production system developed for *Bacillus*, for example for *B. subtilis, B. licheniformis, B. amyloliquelaciens*, for *E. coli*, or for the actinomycete *Streptomyces*. Preferably the serine protease of the invention is produced in a filamentous fungal host of the genus *Trichoderma* or *Aspergillus*, such as *T. reesei*, or *A. niger, A oryzae, A. sojae, A. awamori* or *A. japonicus*-type strains. According the most preferred embodiment of the invention the fungal serine protease enzyme is produced in *T. reesei*.

The production host cell may be homologous or heterologous to the serine protease of the invention. The host may be free of homogenous proteases due to removal of proteases either by inactivation or removal of one or more host proteases, e.g. by deletion of the gene(s) encoding such homogenous or homologous proteases.

The present invention relates also to a process for producing a polypeptide having serine protease activity, said process comprising the steps of culturing the natural or recombinant host cell carrying the recombinant expression vector for a serine protease of the invention under suitable conditions and optionally isolating said enzyme. The production medium may be a medium suitable for growing the host organism and containing inducers for efficient expression. Suitable media are well-known from the literature.

The invention relates to a polypeptide having serine protease activity, said polypeptide being encoded by the nucleic acid molecule of the invention and which is obtainable by the process described above. Preferably, the polypeptide is a recombinant protease enzyme obtained by culturing the host cell carrying the recombinant expression vector for a serine protease enzyme of the invention.

The invention further relates to a process for obtaining an enzyme preparation comprising a polypeptide, which has serine protease activity, said process comprising the steps of culturing a host cell carrying the expression vector of the invention and either recovering the polypeptide from the cells or separating the cells from the culture medium and obtaining the supernatant having serine protease activity.

The present invention relates also to an enzyme preparation, which comprises the serine protease enzyme characterized above. The enzyme preparation or composition has serine protease activity and is obtainable by the process according to the invention.

Within the invention is an enzyme preparation which comprises the fungal serine protease of the invention, preferably the recombinant serine protease obtained by culturing a host cell, which carries the recombinant expression vector of the invention.

Said enzyme preparation may further comprise different types of enzymes in addition to the serine protease of this invention, for example another protease, an amylase, a lipase, a cellulase, cutinase, a pectinase, a mannanase, a xylanase and/or an oxidase such as a laccase or peroxidase with or without a mediator. These enzymes are expected to enhance the performance of the serine proteases of the invention by removing the carbohydrates and oils or fats present in the material to be handled. Said enzymes may be natural or recombinant enzymes produced by the host strain or may be added to the culture supernatant after the production process.

Said enzyme preparation may further comprise a suitable additive selected from the group of surfactants or surface active agent, buffers, anti-corrosion agents, stabilizers, bleaching agents, mediators, builders, caustics, abrasives, optical brighteners, antiredeposition agents, dyes, pigments and preservatives, etc.

Surfactants are useful in emulsifying grease and wetting surfaces. The surfactant may be a non-ionic including semipolar and/or anionic and/or cationic and/or zwitterionic.

Buffers may be added to the enzyme preparation to modify pH or affect performance or stability of other ingredients.

Suitable stabilizers include polyol such as propylene glycol or glycerol, a sugar or sugar alcohol, lactic acid, boric acid, or boric acid derivatives, peptides, etc.

Bleaching agent is used to oxidize and degrade organic compounds. Examples of suitable chemical bleaching systems are $H_2O_2$ sources, such as perborate or percarbonate with or without peracid-forming bleach activators such as tetraacetylethylenediamine, or alternatively peroxyacids, e.g. amide, imide or sulfone type. Chemical oxidizers may be replaced partially or completely by using oxidizing enzymes, such as laccases or peroxidases. Many laccases do not function effectively in the absence of mediators.

Builders or complexing agents include substances, such as zeolite, diphosphate, triphosphate, carbonate, citrate, etc. The enzyme preparation may further comprise one or more polymers, such as carboxymethylcellulose, poly(ethylene glycol), poly(vinyl alcohol), poly(vinylpyrrolidone), etc. Also, softeners, caustics, preservatives for preventing spoilage of other ingredients, abrasives and substances modifying the foaming and viscosity properties can be added.

According to one preferred embodiment of the invention said enzyme preparation is in the form of liquid, powder or granulate.

The fungal serine protease of the present invention may like other proteases, particularly alkaline proteases be used in the detergent, protein, brewing, meat, photographic, leather, dairy and pharmaceutical industries (Kalisz, 1988, Rao et al., 1998). For example, it may be used as an alternative to chemicals to convert fibrous protein waste (e.g. horn, feather, nails and hair) to useful biomass, protein concentrate or amino acids (Anwar and Saleemuddin, 1998). The use of fungal serine protease of the present invention may like other enzymes prove successful in improving leather quality and in reducing environmental pollution and saving energy and it may like alkaline proteases be useful in resolution of the mixture of D,L-amino acids. Subtilisin in combination with broad-spectrum antibiotics in the treatment of burns and wounds is an example of the use of serine proteases in pharmaceutical industry, therefore the fungal serine protease of the present invention may also find such use and may also like alkaline proteases be applicable in removal of blood on surgical equipments and cleaning contact lenses or dentures. Like alkaline protease from *Conidiobolus coronatus*, the fungal serine protease of the present invention may be used for replacing trypsin in animal cell cultures. The proteases of the invention can also be used in cleaning of membranes and destruction of biofilms. In baking proteases are used e.g. in destruction of the gluten network to produce non-elastic doughs with very low water retention. In other food applications, the food proteins are hydrolysed using proteases with the aim of e.g. solubilising protein, rendering (extracting more protein from animal bones), creating new flavours, reducing bitterness, changing emulsifying properties, generating bioactive peptides and reducing allergenicity of proteins, treating yeast or milk. The substrates include animal, plant and microbial proteins.

Detergent industry, particularly the laundry detergent industry, has emerged as the single major consumer of proteases active at high pH range (Anwar and Saleemuddin, 1998). The ideal detergent protease should possess broad substrate specificity to facilitate the removal of large variety of stains due to food, grass, blood and other body secretions. It has to be active in the pH and ionic strength of the detergent solution, the washing temperature and pH, and tolerate mechanical handling as well as the chelating and oxidizing agents added to detergents. The pI of the protease must be near the pH of the detergent solution. Due to present energy crisis and the awareness for energy conservation, it is currently desirable to use the protease at lower temperatures.

The present invention relates also to the use of the serine protease enzyme or the enzyme preparation for detergents, treating textile fibers, for treating wool, for treating hair, for treating leather, for treating feed or food, or for any application involving modification, degradation or removal of proteinaceous material.

One preferred embodiment of the invention is therefore the use of the serine protease enzyme as characterized above as a detergent additive useful for laundry detergent and dish wash compositions, including automatic dish washing compositions.

The expression "detergent" is used to mean substance or material intended to assist cleaning or having cleaning properties. The term "detergency" indicates presence or degree of cleaning property. The degree of cleaning property can be tested on different proteinaceous or protein containing substrate materials or stains or stain mixtures bound to solid, water-insoluble carrier, such as textile fibers or glass. Typical proteinaceous material includes blood, milk, ink, egg, grass and sauces. For testing purposes mixtures of proteinaceous stains are commercially available. The function of the detergent enzyme is to degrade and remove the protein-containing stains. Test results depend on the type of stain, the composition of the detergent and the nature and status of textiles used in the washing test (Maurer, 2004).

Typically, protease or wash performance is measured as "stain removal efficiency" or "stain removal effect" or "degree of cleaning property", meaning a visible and measurable increase of lightness or change in colour of the stained material, e.g. in artificially soiled swatches or test cloths. Lightness or change in colour values can be measured, for example by measuring the colour as reflectance values with a spectrophotometer using L*a*b* colour space coordinates as described in Examples 6 to 10. Fading or removal of proteinaceous stain indicating of the protease performance (stain removal efficiency) is calculated for example as ΔL*, which means lightness value L* of enzyme treated fabric minus lightness value L* of fabric treated with buffer or washing liquor without enzyme (enzyme blank or control). The presence of detergent may improve the performance of the enzyme in removing the stains.

The serine protease of the present invention degrades various kinds of proteinaceous stains under conditions of neutral and alkaline pH and even in the presence detergents with different compositions (as shown in Examples 6 to 13).

Figure 5:
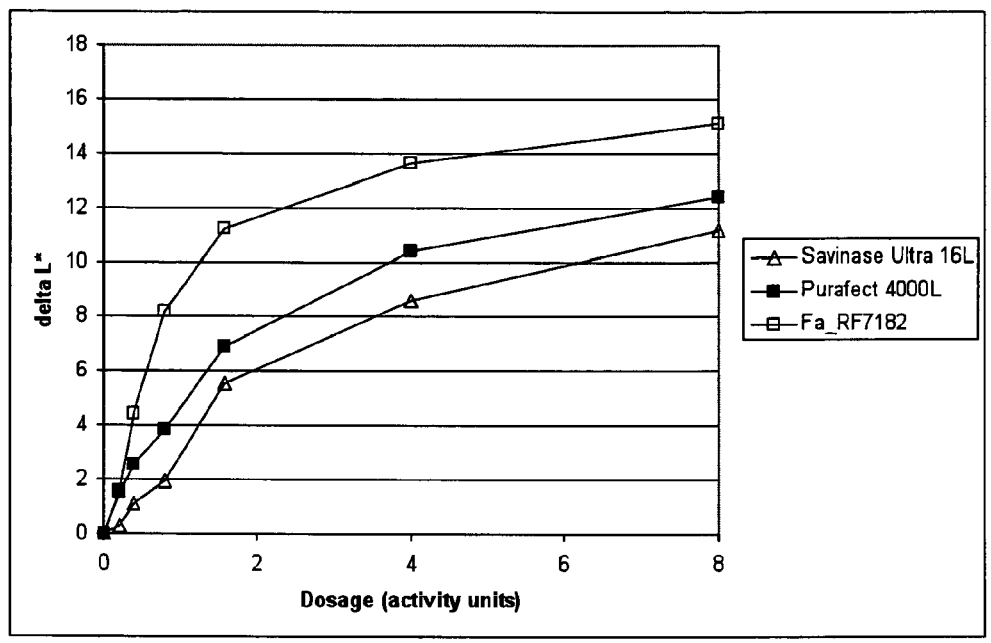
FIG. 5 describes the performance of recombinant Fa_RF7182 protein with blood/milk/ink stain (Art 116, EMPA) at 30° C., pH 9, 60 min. Commercial preparations Savinase® 16L (Novozymes A/S, DK) and Purafect® 4000L (Genencor Inc., USA) were used for comparison. $\Delta L^*$ (deltaL*)=lightness value L* of enzyme treated fabric–lightness value L* of fabric treated with buffer only (enzyme blank).
Figure 6:
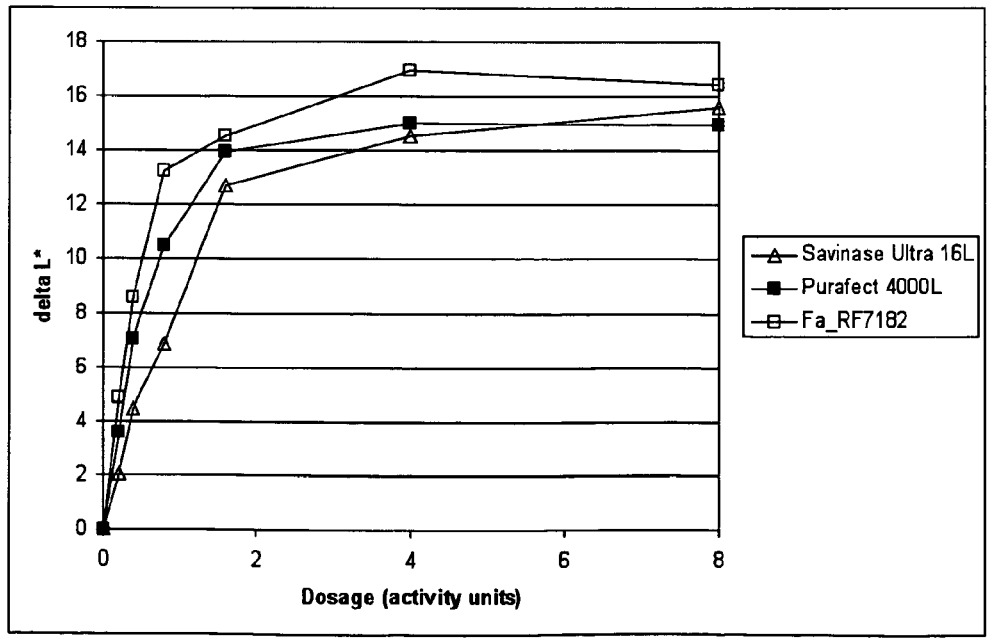
FIG. 6 describes the performance of Fa_RF7182 with blood/milk/ink stain (Art. 116, EMPA) at 50° C., pH 9, 60 min. Commercial preparations Savinase® Ultra 16L and Purafect® 4000L were used for comparison. $\Delta L^*$ (deltaL*)=lightness value L* of enzyme treated fabric–lightness value L* of fabric treated with buffer only (enzyme blank).

As shown in Example 6 the serine protease of the invention removed the blood/milk/ink standard stain at 50° C. and especially at 30° C. in pH 9 buffer and preservatives better than the commercial protease preparations Savinase® Ultra 16L and Purafect® 4000L (FIGS. 5 and 6). The enzyme preparations were dosed as activity units. The stain removal effect on blood/milk/ink stain was tested also at the whole temperature range from 10° C. to 60° C. as described in Example 12. Fa_RF7182 protease preparation showed higher stain removal capacity compared to the commercial protease preparation Savinase® Ultra 16L, Properase® 4000E and Purafect® 4000L especially at low washing temperatures, at a range from 10° C. to 40° C. (FIG. 14).

Figure 7:
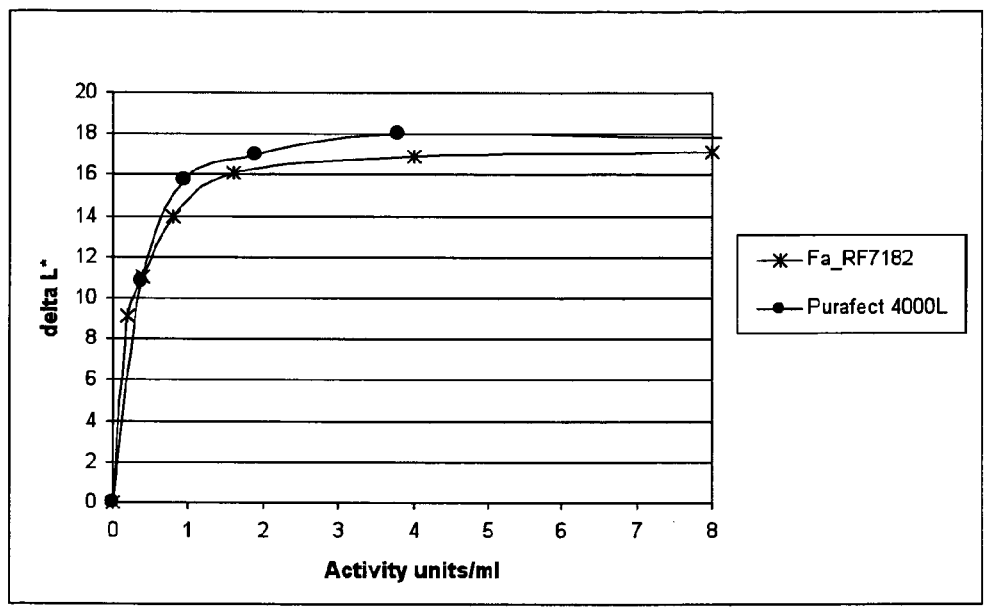
FIG. 7 describes the performance of recombinant Fa_RF7182 with blood/milk/ink stain (Art. 117, EMPA) in the presence of detergent powder (Art. 601, EMPA) at 40° C. and pH 10. Commercial preparation Purafect® 4000L was used for comparison. Shown at x-axis enzyme dosage (activity/ml), at y-axis $\Delta L^*$ (deltaL*)=lightness value L* of enzyme treated fabric–lightness value L* of fabric treated with buffer only (enzyme blank).

The performance of the Fa_RF7182 protease was tested also in detergent powder at 40° C. at pH 10 as described in Example 7. The ability of the enzyme in removing blood/milk/ink standard stain on polyester-cotton material (Art.117, EMPA) in presence of phosphate containing reference detergent was determined. Each enzyme preparation was dosed as activity units (µmol tyrosine/minute). As shown in FIG. 7 the protease of the invention is suitable also for powder detergents at very alkaline conditions. The performance of Fa_RF7182 enzyme was similar to commercial protease Purafect® 4000L at 40° C.

The Fa_RF7182 protease removed blood/milk/ink standard stain on polyester-cotton material (Art.117, EMPA) also in the presence of liquid detergent Ariel Sensitive without enzymes (Procter & Gamble, UK) as shown in Example 8. The enzyme was dosed as activity units (µmol tyrosine/minute/volume). The dosage of 4-8 units of commercial enzyme preparations per ml of liquor was equal to dosage of about 0.2-0.5% of enzyme preparation per weight of detergent, which is typical level for use of detergent enzymes. The Fa_RF7182 showed excellent performance with liquid detergent (FIG. 8) and the increase in lightness of the stained material was considerably higher than with the commercial preparations Savinase® Ultra 14L and Purafect® 4000L.

Similar results were observed when the performance of the Fa_RF7182 enzyme was tested using different liquid detergent concentrations (Example 9, FIGS. 9A-D and 10A-D) at 30° C. The efficiency of Fa_RF7182 on blood/milk/ink stain was considerably higher compared to commercial preparations Purafect® 4000L and Savinase® Ultra 14 L with both detergents and at all detergent concentrations, when same amount of activity was dosed. Also if dosing was calculated as amount of added protein (FIGS. 9B and 10B), the stain removal efficiency was the highest with Fa_RF7182. Washings were performed also at lower temperatures with a liquid detergent concentration of 3.3 g/l as described in Example 13. At 10° C. and 20° C. the Fa_RF7182 preparation showed superior performance over the commercial preparations Savinase® Ultra 14L, Purafect® 4000L and Properase® 4000E (FIG. 15).

In addition to the blood/milk/ink stains on cotton or polyester cotton fabrics, the Fa_RF7182 serine protease was effective in removing other stains, such as grass (Art.164, EMPA) and cocoa (Art.112, EMPA) when tested in liquid detergents at 30° C. Treatments were performed in ATLAS LP-2 Launder-Ometer. Results (FIG. 11) show that the Fa_RF7182 was effective in removal of different stains at low temperatures like 30° C.

The performance of recombinant Fa_RF7182 enzyme preparation produced in *T. reesei* was tested in the presence of liquid base detergent in full scale in a washing machine at 30° C. (Example 11) and compared to commercial preparations Savinase® Ultra 16L and Purafect® 4000L. Eight different protease sensitive tracers for testing side effects are presented in Table 5 and the process conditions in Table 6. Enzyme dosages used in the test trials were calculated both as enzyme activities and as amount of enzyme protein. Results with the different stains presented in FIGS. 12 and 13 show that Fa_RF7182 protease was more effective than the commercial enzyme preparations. The Fa_RF7182 was most efficient on blood/milk/ink, chocolate/milk, groundnut oil/milk and egg yolk (FIG. 13).

As observed from FIGS. 5 to 11 the lightness L* of the test material was remarkably increased in the presence of the fungal serine protease of the invention. Using Fa_RF7182 enzyme preparation, better lightness compared to competitor products was obtained with similar enzyme activity dosage or in other words, similar lightness compared to competitor products was obtained with lower enzyme activity dosage.

The Fa_RF7182 protease was also tested in full-scale trials at 30° C. using liquid detergent and a selection of protease sensitive tracers (Example 11), In these tests, the total stain removal effect, based on the sum of the results obtained with the eight different protease sensitive stains (Stains 1-8, Table 5) was considerably higher with Fa_RF7182 compared to commercial protease preparations Purafect® 4000L and Savinase® Ultra 16L, when proteases were dosed as amount of activity (FIG. 12A). Fa_RF7182 was efficient especially on blood/milk/ink, chocolate/milk, groundnut oil/milk and egg yolk (FIGS. 13A-E).

According to a preferred embodiment of the invention the fungal serine protease of the invention is useful in detergent liquids and detergent powders as shown in Examples 6 to 11. The enzyme or enzyme preparation of the invention may be formulated for use in a hand or machine laundry or may be formulated for use in household hard surface cleaning or preferably in hand or machine dish washing operations.

Example 1

Production and Purification of the *Fusarium acuminatum* RF7182 Protease (a) Cultivation of *Fusarium acuminatum* RF7182 Protease Fungal strain originally named as TUB F-2008 was isolated from a soil sample as a filamentous fungus growing on alkaline (pH 8.5) agarose plate. It produced protease activity, according to hydrolysis of casein and haemoglobin included in the agar plate. As the plate cultivations were performed at 8-10° C. this result suggested that TUB F-2008 produces a protease or proteases acting at cold temperatures. TUB F-2008 was identified as *Fusarium acuminatum* Ellis & Everh (identified by Arthur de Cock at Identification Services, Centralbureau Voor Schimmelcultures, P.O. Box 85167, 3508 AD Utrecht, The Netherlands) and was renamed as RF7182. The *F. acuminatum* RF7182 was grown, maintained and sporulated on Potato Dextrose (PD) agar (Difco) at +4° C. For enzyme production spores from RF7182 slant were inoculated into a culture medium which contained: 30 g/l Corn meal (finely ground), 5 g/l Corn steep powder, 4 g/l Soybean meal (defatted), 2 g/l $KH_2PO_4$, 1 g/l NaCl and 1 g/l Paraffin oil. The pH of the medium was adjusted before sterilization with NaOH to 8.5 and the medium was autoclaved for 30 minutes at 121° C. The microbe was cultivated in 50 ml volume on a shaker (200 rpm) at 28° C. for 7 days. The spent culture supernatant was shown to contain alkaline protease activity, when activity measurements were performed (according to Example 1c) at different pH values (pH 7-10). Because of this alkaline activity, the RF7182 strain was chosen as putative protease gene donor strain.

(b) Purification of Protease from the *F. acuminatum* RF7182 Culture Medium

Cells and solids were removed from the spent culture medium by centrifugation for 30 min, 50000 g at +4° C. (Sorvall RC6 plus). 50 ml of the supernatant was used for purification of the protease. After centrifugation, pH of supernatant was adjusted to 8.0 with addition of HCl. The supernatant was then filtered through 0.44 μm filter (MILLEX HV Millipore) and applied to a 5 mL Q Sepharose FF column (GE Healthcare) equilibrated in 20 mM Tris-HCl, pH 8. Flow through fraction was collected and its pH was lowered to 7.5 by adding HCl. Solid ammonium sulfate was added to the flow through fraction to obtain a final salt concentration of 1 M. The flow through fraction was then filtered through 0.44 μm filter before applying to phenyl Sepharose HP (5 mL) column (GE Healthcare) equilibrated in 20 mM Tris-HCl-1M ammonium sulfate pH 7.5. The proteins were eluted with a linear decreasing ammonium sulfate gradient (from 1 to 0 M). Fractions of 5 ml were collected and analyzed for protease activity on resorufin-labeled casein (Boehringer Mannheim Biochemica) at pH 8.0 as instructed by the manufacturer. Fractions with protease activity were pooled and ultra filtrated with 10 k membrane (Amicon). The concentrated filtrate was applied to a Superdex 75 10/300 GL column (GE Healthcare) equilibrated with 20 mM Tris-HCl-200 mM NaCl, pH 7.5. Proteins were eluted with the same buffer and 0.5 ml fractions were collected. The protease activity from these fractions was analysed. The fractions with protease activity were analyzed on sodium dodecyl sulfate polyacrylamide gel electrophoresis (SDS-PAGE). The fractions were shown to contain one major protein band having a molecular mass of about 29 kDa. The chosen fractions were pooled. The pooled fractions were used for preparation of peptides (Example 2). This purified *F. acuminatum* RF7182 protease was named as Fa_RF7182.

(c) Protease Activity Assay

Protease activity was assayed by the casein Folin-Ciocalteau method using casein as a substrate. Rate of casein degradation by a protease was measured by spectrophotometrical monitoring of the release of acid-soluble fragments as a function of time. Casein substrate used in the assay was prepared as follows: 6 g of Casein Hammerstein Grade MP Biomedicals, LLC (101289) was dissolved in 500 ml of 30 mM Tris, 2.0 mM $CaCl_2$, 0.7 mM $MgCl_2$, 2.5 mM $NaHCO_3$. The pH of the substrate solution was adjusted to 8.5. The enzyme reactions were stopped using 0.11 M TCA solution. The Folin reagent used in the assay was prepared by diluting 25 ml of 2 N Folin-Ciocalteu's phenol reagent (SIGMA, F 9252) to 100 ml by distilled water. The reaction was started by first incubating 2.5 ml of substrate solution for 5 min at 50° C. after which 0.5 ml of enzyme solution was added and reaction was conducted for 30 min. After 30 min reaction 2.5 ml of reaction stop solution was added, the contents were mixed and allowed to stand for 30 minutes at room temperature. Tubes were centrifuged 4000 rpm for 10 minutes (Hettich Rotanta 460). One ml of clear supernatant was mixed with 2.5 ml 0.5 M $Na_2CO_3$ and 0.5 ml diluted Folin reagent. After waiting for at least 5 min (color development) the absorbance of the mixture (colour) was measured at 660 nm against an enzyme blank.

interest were removed and subjected to N-terminal sequence analysis by Edman degradation on a Procise 494A protein sequencer (Perkin Elmer Applied Biosystems Division, Foster City, Calif.)

The N-terminal and internal peptide sequences determined from the purified Fa_RF7182 protease are shown in Table 1. The peptide sequences showed homology to a published hypothetical protease sequence from *Gibberella zeae* (*Fusarium graminearum*) with EMBL Accession number XP_383491. According to comparison of the sequences, all the peptide sequences obtained were located close to the N-terminus of the mature Fa_RF7182 protein.

TABLE 1

N-terminal and internal peptide sequences determined from *Fusarium acuminatum* RF7182 protease Fa_RF7182.

| Peptide | Sequence | SEQ ID NO | Comments |
|---|---|---|---|
| #3811 | A(L/I)TXQSNAPW | SEQ ID NO: 1 | N-terminal sequence |
| 1609, 880 | SGAPWG(L/I)Q(L/I)SHK | SEQ ID NO: 2 | |
| 1793, 957 | (A/L/I)(A/L/I)TTQSGAPWG(L/I)GA(L/I)SHK | SEQ ID NO: 3 | |
| 743, 494 | (A/N)(A/N)(L/I)(L/I)SVK | SEQ ID NO: 4 | |
| 2103, 832 (start 2045, 06) | GGAHTD | SEQ ID NO: 5 | |
| 2103, 832 (start 1406, 57) | NGHGTHVAGT(L/I)NTK | SEQ ID NO: 6 | |
| 3662, 692 | TSY(L/I)YDTTAGSGSYGYYVDSG(L/I)N(L/I)AHYS(L/I)NR | SEQ ID NO: 7 | |

The enzyme blank was prepared as follows: 0.5 ml enzyme solution was mixed with 2.5 ml stopping solution and 2.5 ml substrate, and the mixture was incubated for 30 min at 50° C. One unit of enzyme activity was defined as the enzyme quantity that liberates the acid soluble protein hydrolysis product corresponding to 1 μg of tyrosine per ml (or g) of the reaction mixture per min.

Example 2

N-Terminal and Internal Amino Acid Sequencing of the Purified *Fusarium acuminatum* RF7182 Protease For determination of internal sequences, the Coomassie Brilliant Blue stained band was cut out of the polyacrylamide gel and "in-gel" digested essentially as described by Shevchenko et al. (1996). Proteins were reduced with dithiothreitol and alkylated with iodoacetamide before digestion with trypsin (Sequencing Grade Modified Trypsin, V5111, Promega).

Electrospray ionization quadrupole time-of-flight tandem mass spectra for de novo sequencing were generated using a Q-TOF instrument (Micromass, Manchester, UK) connected to an Ultimate nano liquid chromatograph (LC-Packings, The Netherlands) essentially as described previously (Poutanen et al., 2001) but using a 150 μm×1.0 mm trapping column (3 μm, 120A, #222403, SGE Ltd UK) for peptide preconcentration.

For N-terminal sequence analysis SDS-PAGE/separated proteins were transferred by electroblotting into a polyvinylidine difluororide membrane (ProBlott; Perkin Elmer Applied Biosystems Division, Foster City, Calif.) After being stained with Coomassie brilliant blue, the protein bands of Example 3

Cloning of the *Fusarium acuminatum* RF7182 Gene Encoding Fa_RF7182 Protein (a) Isolation of DNA and Molecular Biology Methods Used Standard molecular biology methods were used in the isolation and enzyme treatments of DNA (e.g. isolation of plasmid DNA, digestion of DNA to produce DNA fragments), in *E. coli* transformations, sequencing etc. The basic methods used were either as described by the enzyme, reagent or kit manufacturer or as described in the standard molecular biology handbooks, e.g. Sambrook and Russell (2001). Isolation of genomic DNA from *F. acuminatum* RF7182 was done as described in detail by Raeder and Broda (1985).

(b) Primers for Probe Preparation

The probe for cloning the gene encoding the Fa_RF7182 protein was amplified by PCR. Degenerate sense oligonucleotides were planned basing on the amino acid sequences of the peptides obtained from the purified RF7182 (Table 1) and antisense oligonuclotides using a chosen consensus area from different published S8 type serine protease sequences. Conserved sequence areas were determined from alignment of sequences with accession numbers AAR11460 (*Trichophyton rubrum*), CAD24010 (*Microsporum canis*), AAT65816 (*Penicillium nordicum*), Q5NDC0 (*Penicillium chrysogenum*) and AAC27316 (*Fusarium oxysporum*). The combinations of the primers in the PCR reactions were chosen according to the location of the peptide homologues in the published protease sequences. The sequences of the primers are shown in Table 2 (SEQ ID NOs: 8-11).

TABLE 2

The oligonucleotides (SEQ ID NOs: 8-11) synthesized as PCR primers in probe amplification. Oligos, SEQ ID NOs, oligo lengths and degenaracies, oligonucleotides and the amino acids of the peptide used in planning of the oligonucleotide sequence.

| Oligo | SEQ ID NO: | Length (nts) | Degeneracy | Sequence[a] | Peptide[b] |
|---|---|---|---|---|---|
| PRO123 | 8 | 20 | 1024 | CARWCNGGNGCNCCNTGGGG (s) | 1793, 957 |
| PRO122 | 9 | 20 | 1024 | CAYGGNACNCAYGTNGCNGG (s) | 2103, 832 (start 1406, 57) |
| PRO60 | 10 | 22 | 64 | GMRGCCATRGAGGTWCCRGTSA (as) | |
| PRO61 | 11 | 20 | 32 | GGMGMRGCCATRGAGGTWCC (as) | |

[a]R = A or G, S = C or G, W = A or T, M = A or C, Y = T or C, N = A, C, T or G; "s" in the parenthesis = sense strand, "as" in the parenthesis = antisense strand.
[b]The peptides sequences are included in Table 1.

c) PCR Reactions and Selection of Probes for Cloning

*F. acuminatum* RF7182 genomic DNA was used as template for probe synthesis. The PCR reaction mixtures contained 1× Phusion™ GC Buffer, 0.25 mM dNTPs, 5% DMSO, 1 μM each primer and 2 units of Phusion™ DNA polymerase (Finnzymes, Finland) and approximately 3 μg of genomic DNA per 100 μl reaction volume. The conditions for the PCR reactions were the following: 1 min initial denaturation at 98° C., followed by 29 cycles of 10 sek at 98° C., 30 sek annealing at 48-58.5° C., 30 sek extension at 72° C. and a final extension at 72° C. for 5 min. Primer combination PRO123 (SEQ ID NO:8) and PRO61 (SEQ ID NO:11) produced a specific DNA product having the expected size (calculated from the published fungal protease sequences). The DNA product was isolated and purified from the PCR reaction mixture and cloned to pCR® 4-TOPO® vector according to the manufacturers instructions (Invitrogen, USA). The 753 bp PCR fragment was sequenced from this plasmid (SEQ ID NO: 12). The pCR® 4-TOPO® plasmid containing this PCR amplified DNA fragment was named pALK2530. The *E. coli* strain RF7803 including the plasmid pALK2530 was deposited to the DSM collection under the accession number DSM 22208.

The deduced amino acid sequence of the PCR fragment included the sequences of the internal RF7182 peptides SEQ ID NOs:1-7. Peptides with SEQ ID NOs: 6 and 7 and the C-terminal part of the peptide SEQ ID NO:2 matched partly to the deduced amino acid sequence. Peptides with SEQ ID NO:4 and SEQ ID NO:5 and the C-terminal part of the peptide SEQ ID NO: 3 matched completely (Table 1). This confirms that the DNA fragment obtained from the PCR reaction was part of the gene encoding the Fa_RF7182 protein and was thus used as a probe for screening the full length gene from *F. acuminatum* RF7182 genomic DNA.

(d) Cloning of the *F. acuminatum* RF7182 Gene Encoding Fa_RF7182 Protease

*F. acuminatum* genomic DNA was digested with several restriction enzymes for Southern blot analysis. The hybridization was performed with the 771 kb EcoRI fragment including SEQ ID NO:12 from the plasmid pALK2530 as a probe (Example 3c). The above probe was labeled by using digoxigenin according to supplier's instructions (Roche, Germany). Hybridization was performed over night at 65° C.

After hybridization the filters were washed 2×5 min at RT using 2×SSC-0.1% SDS followed by 2×15 min at 65° C. using 0.1×SSC-0.1% SDS.

Several hybridizing fragments in the *F. acuminatum* RF7182 genomic DNA digests could be detected. Genomic SalI digests contained a hybridizing fragment of about 5 kb in size. The single hybridizing fragment size was large enough to contain the full length gene encoding the RF7182 protein according to calculations basing on published fungal protease sequences. Genomic DNA fragments were isolated from the RF7182 genomic SalI digest from the size range of the hybridizing fragment. The genomic fragments isolated from agarose gel were cloned to pBluescript II KS+(Stratagene, USA) vectors cleaved with SalI. Ligation mixture was transformed to *Escherichia coli* XL10-Gold cells (Stratagene) and plated on LB (Luria-Bertani) plates containing 50-100 μg/ml ampicillin. The *E. coli* colonies were screened for positive clones using colonial hybridization with the pALK2530 insert as a probe. Hybridization was performed as described for the RF7182 genomic DNA digests. Several clearly positive clones were collected from the plates and one was confirmed with sequencing. The full-length gene encoding the Fa_RF7182 protease (SEQ ID NO:13) was sequenced from the 5 kb SalI insert and the plasmid containing this insert was named pALK2531. The *E. coli* strain RF7879 including the plasmid pALK2531 was deposited to the DSM collection under the accession number DSM 22209. The gene encoding the Fa_RF7182 protease was named as Fa prtS8A.

(e) Characterisation of the Gene Encoding Fa_RF7182 Protease and the Deduced Amino Acid Sequence The Fa prtS8A sequence (SEQ ID NO:13) and the deduced amino acid sequence (SEQ ID NO:14) are shown in FIGS. 1A and 1B. The length of the gene is 1353 bp (including the stop codon). Two putative introns were found having the lengths of 51 bps and 54 bps (5' and 3' border sequences according to those of fungal introns, according to Gun et al., 1987). The deduced protein sequence (SEQ ID NO:14) consists of 415 amino acids including a predicted signal sequence of 20 amino acids (SignalP V3.0; Nielsen et al., 1997 and Nielsen and Krogh, 1998). The N-terminal parts of peptides with SEQ ID NOs:1-3, not included in the probe sequence, were included in the deduced amino acid sequence. The peptide with SEQ ID NO:3 matched the deduced amino acid sequence completely. The predicted molecular mass was 28568.64 Da for the mature polypeptide and the predicted pI was 9.08. These predictions were made using the Compute pI/MW tool at ExPASy server (Gasteiger et al., 2003). The deduced amino acid sequence contained two possible N-glycosylation sites at amino acid positions Asn79 and Asn258 (FIG. 1), but according to CBS Server NetNGlyc V1.0 only the site at position Asn79 (located in the pro-peptide) is probable.

(f) Homology, Identity and Alignment Studies

The homologies to the published protease sequences were searched using the BLASTX program version 2.2.9 at NCBI (National Center for Biotechnology Information) with default settings (Altschul et al., 1990). The highest homologies were to a hypothetical protein from *Gibberella zeae* (*Fusarium graminearum*) (EMBL accession number XP 383491) and *Hypocrea lixii* (*Trichoderma harzianum*) serine endopeptidase (EMBL Accession number CAL25580). Also homology was found to a sequence included in the patent application U.S. 60/818,910 (Catalyst Biosciences Inc.), SEQ ID 313 in the application. The RF7182 mature amino acid sequence was aligned with the above homologous mature amino acid sequences. The identity values obtained by using ClustalW alignment (ebi.ac.uk/Tools/Clustalw; Matrix: BLOSUM, Gap open: 10, Gap extension: 0.5, EMBL-EBI) are shown in Table 3.

TABLE 3

The identity values (%) obtained from ClustalW alignment of the deduced Fa_RF7182 protease amino acid sequences. The mature amino acid sequences excluding the signal peptides and propeptides were aligned. Matrix: BLOSUM, Gap open: 10, Gap extension: 0.5, EMBL_EBI. *G. zeae*, XP_383491; *T. harzianum*, CAL25508; US 60/818,910, SEQ ID NO: 313 in the application.

|  | Fa_RF7182 | *G. zeae* | *T. harz.* | US 60/818,910 |
|---|---|---|---|---|
| Fa_RF7182 | 100 | 80 | 79 | 76 |
| *G. zeae* |  | 100 | 78 | 76 |
| *T. harz.* |  |  | 100 | 94 |
| US 60/818,910 |  |  |  | 100 |

Example 4

Production of the Recombinant Fa_RF7182 in *Trichoderma reesei*

(a) Preparing the Production (Host) Vector

The expression plasmid pALK2536 was constructed for production of recombinant RF7182 protease in *Trichoderma reesei*. The Fa prtS8A gene with its own signal sequence was exactly fused to the *T. reesei* cbh1 (cel7A) promoter by PCR. The Fa prtS8A gene fragment was excised from its 3'-end by BamHI (a site created after stop codon in PCR). This leaves no original Fa prtS8A terminator in the construct prior to the cbh1 terminator sequence. An amdS marker gene was added to the construction including the cbh1 promoter, the Fa prtS8A gene and cbh1 terminator. The construction is analogous to that described in Paloheimo et al. (2003) and the 8.7 kb linear expression cassette is presented in FIG. 2. The expression cassette was isolated from the vector backbone after EcoRI digestion and was used for transforming *T. reesei* protoplasts. The host strain used does not produce any of the four major *T. reesei* cellulases (CBHI, CBHII, EGI, EGII). The transformations were performed as in Penttilä et al. (1987) with the modifications described in Karhunen et al. (1993). The transformants were purified on selection plates through single conidia prior to sporulating them on PD.

(b) Protease Production in Shake Flasks and Laboratory Scale Bioreactor

The transformants were inoculated from the PD slants to shake flasks containing 50 ml of complex lactose-based cellulase inducing medium (Joutsjoki et al., 1993) buffered with 5% $KH_2PO_4$ at pH 6.0. The protease production of the transformants was analyzed from the culture supernatants after growing them for 7 days at 30° C., 250 rpm. In SDS-PAGE gels, a major protein band of about 29 kDa corresponding to recombinant Fa_RF7182 protease was detected from the spent culture supernatants. The protease activity was assayed using casein as a substrate as described in Example 1c. Clearly increased activities compared to host were measured from the culture supernatants. The integration of the expression cassette into the fungal genomes was confirmed from chosen transformants by using Southern blot analysis in which several genomic digests were included and the expression cassette was used as a probe.

The *T. reesei* transformants producing the best protease activities in the shake flask cultivations were chosen to be cultivation in laboratory scale bioreactors. Cellulase inducing complex medium was used in the cultivations. The spent culture medium obtained from the cultivations was used in application tests (Examples 6-11) and as starting material for purification and further characterization of the recombinant Fa_RF7182 protease.

Example 5

Purification and Characterization of the Recombinant Fa_RF7182 Protease

Figure 3:
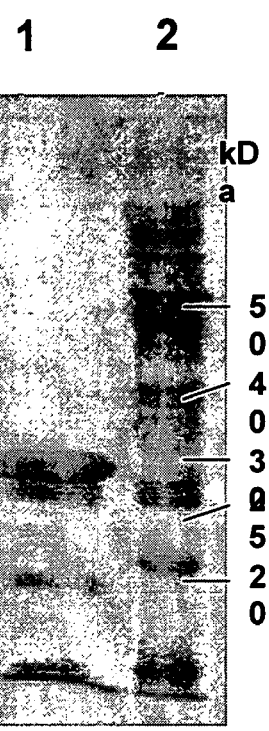
FIG. 3 shows the partially purified recombinant Fa_RF7182 protein analysed on 12% SDS PAGE gel. Lane 1. Sample of the partially purified Fa_RF7182, Lane 2. MW marker (Bench Mark Protein Ladder, Invitrogen).

Cells and solids were removed from the spent culture medium obtained from the fermentation (Example 4) by centrifugation for 30 min, 50000 g at +4° C. (Sorvall RC6 plus). 15 ml of the supernatant was used for purification of protease. All purification steps were performed at cold room. After centrifugation, sample was filtered through 0.44 µm filter (MILLEX HV Millipore) before applying to HiPrep 26/10 Desalting column (from GE Healthcare) equilibrated in 20 mM Tris pH 8.5. Gel filtered sample was applied to a 20 mL Q Sepharose FF column (from GE Healthcare) equilibrated in 20 mM Tris pH 8.5. The flow through fraction was collected and analysed on 12% SDS PAGE gel (FIG. 3). This enzyme sample was used for characterization of pH and temperature profiles.

Temperature Profile

Figure 4A:
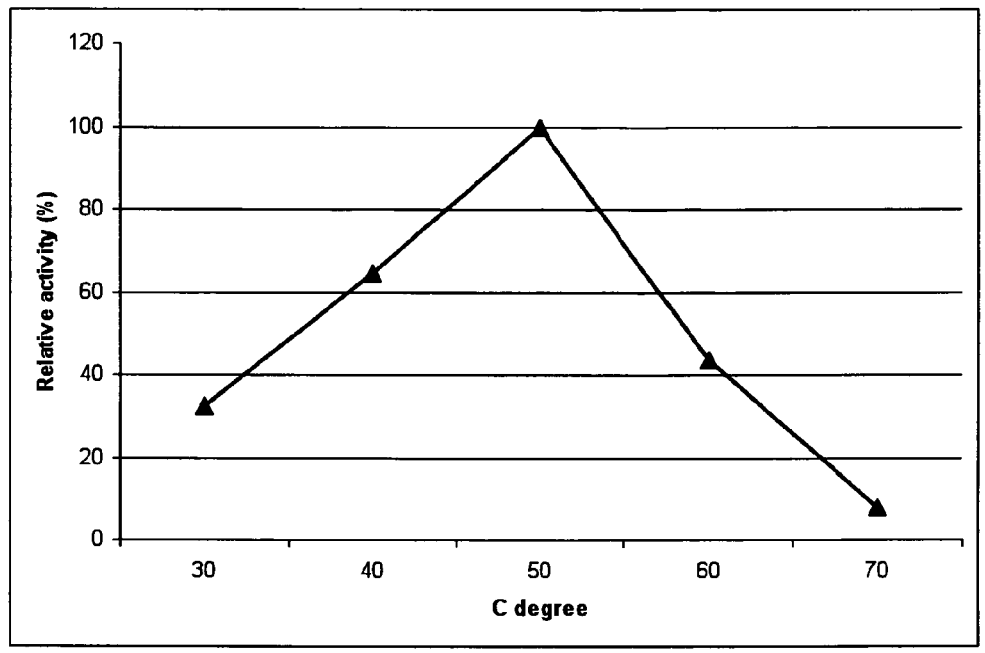
FIG. 4A describes the temperature profile of recombinant protein Fa_RF7182 assayed at pH 9 using 15 min reaction time and casein as a substrate. The data points are averages of three separate measurements.

Temperature profile was obtained for Fa_RF7182 protease by using the assay described in Example 1c, except using 15 min reaction time at pH 9. The result is shown in FIG. 4A. The protease has an optimal temperature around 50° C.

pH-Profile

Figure 4B:
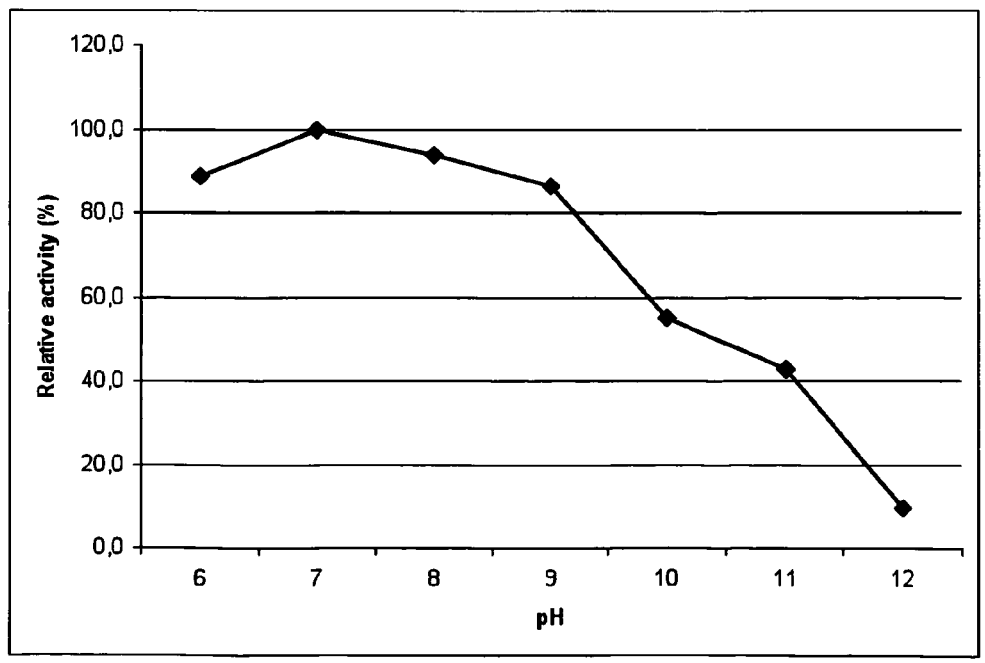
FIG. 4B describes the effect of pH on the activity of recombinant Fa_RF7182 protein. The buffer used was 40 mM Britton-Robinson buffer at pH 6 to pH 12 and reaction temperature was 50° C. The reaction time was 15 minutes, casein was used as a substrate. The data points are averages of three separate measurements.

The pH profile of the protease was determined at 50° C. using casein as a substrate as described in Example 1c, except that casein was dissolved in 40 mM Britton-Robinson buffer, the pH of the reaction was adjusted to pH 6-12, the reaction time was 15 min and the enzyme reactions were stopped using a 0.11 M TCA solution which contained 0.22 M sodium acetate and 0.33 M acetic acid. The results are shown in FIG. 4B. The recombinant Fa_RF7182 protease exhibits relative activity over 85% from pH 6 to pH 9. The pH profile of the purified recombinant Fa_RF7182 protease corresponded to the pH profile of the wild type Fa_RF7182 protease purified as described in Example 1a.

Example 6

Performance of Recombinant Protein Fa_RF7182 at pH 9 Buffer at Different Temperatures Recombinant protein Fa_RF7182 preparation produced in *Trichoderma* (as described in Example 4), was tested for its ability to remove blood/milk/ink standard stain (Art.116, 100% cotton, EMPA Testmaterialen AG, Swizerland) at temperatures 30° C. and 50° C. Commercial protease preparations Savinase® Ultra 16 L (Novozymes) and Purafect® 4000 L (Genencor International) and treatment without enzyme (control) were used for comparison. The stain fabric was first cut in to 1.5 cm×1.5 cm swatches and the pieces were made rounder by cutting the corners. Pieces were placed in wells of microtiter plates (Nunc 150200). Into each well having diameter of 2 cm, 1.5 ml enzyme dilution in Glysine-NaOH buffer pH 9 was added on top of the fabric. Each enzyme was dosed 0, 0.2, 0.4, 0.8, 1.6, 4, and 8 activity units (μmol tyrosine/min) per 1.5 ml buffer. Activity was measured using 30 min reaction time as described in Example 1(c) and using 10 min time for color development after addition of diluted Folin reagent. Microtiter plates with samples were incubated in a horizontal shaker at 30° C. and 50° C. for 60 min with 125 rpm. After that the swatches were carefully rinsed under running water (appr. 45° C.) and dried overnight at indoor air on a grid, protected against daylight.

The stain removal effect was evaluated by measuring the colour as reflectance values Minolta CM 2500 spectrophotometer using L*a*b* colour space coordinates (illuminant D65/2°.) The colour from both sides of the swatches was measured after the treatment. Each value was the average of at least 2 parallel fabric samples measured from both side of the fabric. Fading of blood/milk/ink stain indicating of the protease performance (stain removal efficiency) was calculated as $\Delta L^*$, which means lightness value L* of enzyme treated fabric minus lightness value L* of fabric treated with washing liquor (buffer) without enzyme (enzyme blank, control).

The results are shown in FIGS. 5 and 6. Fa_RF7182 protease preparation showed considerably higher stain removal capacity especially at 30° C. in pH 9 buffer compared to commercial protease preparations Savinase® Ultra 16L and Purafect® 4000L.

Example 7

Performance of Recombinant Protein Fa_RF7182 with Detergent Powder at 40° C. And pH 10

Recombinant protein Fa_RF7182 preparation produced *Trichoderma* (as described in Example 4) was tested for its ability to remove blood/milk/ink standard stain in the presence of phosphate containing reference detergent at 40° C. (pH ca. 10). Standard stain Art.117 (blood/milk/ink, polyester+cotton, EMPA) was used as test material. Commercial protease Purafect® 4000L and treatment without enzyme (control) were used for comparison. Each enzyme was dosed 0, 0.2, 0.4, 0.8, 1.6, 4, and 8 activity units (μmol tyrosine/min) per ml wash liquor. Activity was measured as described in Example 6.

An amount of 3.3 g of phosphate containing ECE reference detergent 77 without optical brightener (Art. 601, EMPA) was dissolved in 1 liter of tap water (dH≤4), mixed well with magnetic stirrer and tempered to 40° C. Stain fabric was cut into pieces like described in Example 6. Swatches were placed in well's of microtiter plates (Nunc 150200) and 1.5 ml wash liquor containing detergent and enzyme dilution in water (below 70 μl) was added on top of the fabric. The plates with samples were in incubated in horizontal shaker at 40° C. for 60 min with 125 rpm. After that the swatches were carefully rinsed under running water (appr. 45° C.) and dried overnight at indoor air, on a grid, protected against daylight.

The colour of the swatches after treatment was measured with Minolta CM 2500 spectrophotometer using L*a*b* colour space coordinates stain removal effect calculated as $\Delta L^*$ as described in example 6.

The results (FIG. 7) showed that protease Fa_RF7182 is also suitable with for powder detergents at very alkaline conditions. The performance was similar to commercial protease Purafect® 4000L at 40° C.

Example 8

Performance of Recombinant Protein Fa_RF7182 with Liquid Detergent at 40° C.

Recombinant protein Fa_RF7182 preparation produced in *Trichoderma* (as described in Example 4) was tested for its ability to remove blood/milk/ink standard stain in the presence of liquid detergent Ariel Sensitive (Procter & Gamble, England), not containing enzyme, at 40° C. and pH ca. 7.9. Standard stain, artificially soiled test cloth Art.117 (blood/milk/ink, polyester+cotton, EMPA) was used as test material. Commercial protease preparations Purafect® 4000L and Savinase Ultra® 16 L and treatment without enzyme (control) were used for comparison. Each enzyme was dosed 0, 0.2, 0.4, 0.8, 1.6, 4, and 8 activity units (μmol tyrosine/min) per ml wash liquor. Activity was measured as described in Example 6.

An amount of 3.3 g of Ariel Sensitive was dissolved in 1 liter of tap water (dH≤4), mixed well with magnetic stirrer and tempered to 40° C. Stain fabric was cut into pieces like described in Example 6. Swatches were placed in well's of microtiter plates (Nunc 150200) and 1.5 ml wash liquor containing detergent and enzyme dilution in water (<70 μl) was added on top of the fabric. The plates with samples were in incubated in a horizontal shaker at 40° C. for 60 min with 125 rpm. After that the swatches were carefully rinsed under running (appr. 45° C.) water and dried overnight at indoor air, on a grid, protected against daylight.

The colour of the swatches after treatment was measured with Minolta CM2500 spectrophotometer using L*a*b* color space coordinates and stain removal effect calculated as $\Delta L^*$ as described in example 6.

Figure 8:
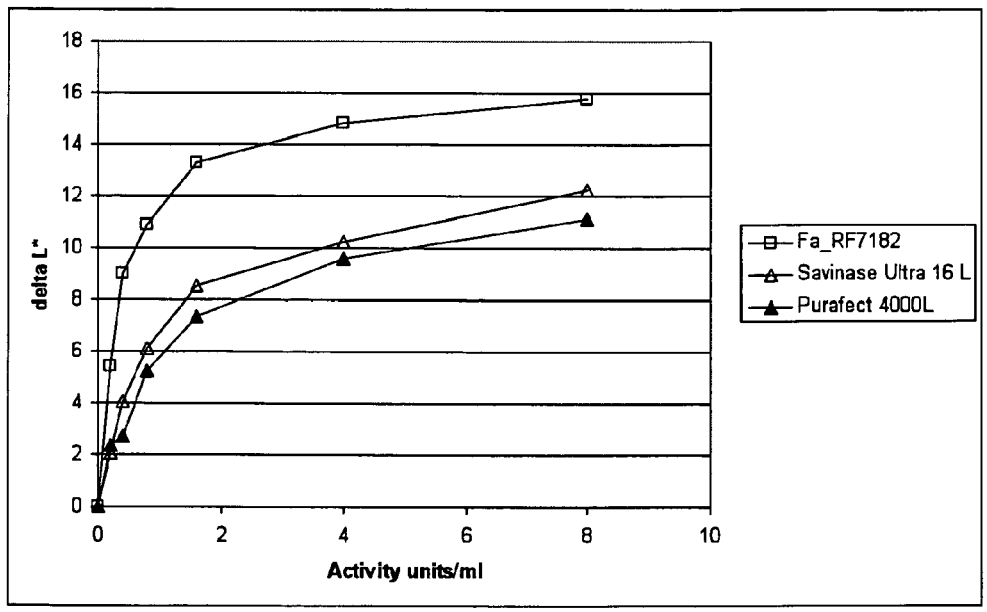
FIG. 8 shows the performance of recombinant protein Fa_RF7182 with blood/milk/ink stain (Art 117, EMPA) and liquid detergent Ariel Sensitive (without enzymes) at 40° C., at approximately pH 7.9, 60 min. Commercial preparation Purafect® 4000L was used for comparison. $\Delta L^*$ (deltaL*)=lightness value L* of enzyme treated fabric–lightness value L* of fabric treated with buffer only (enzyme blank).
Figure 9A:
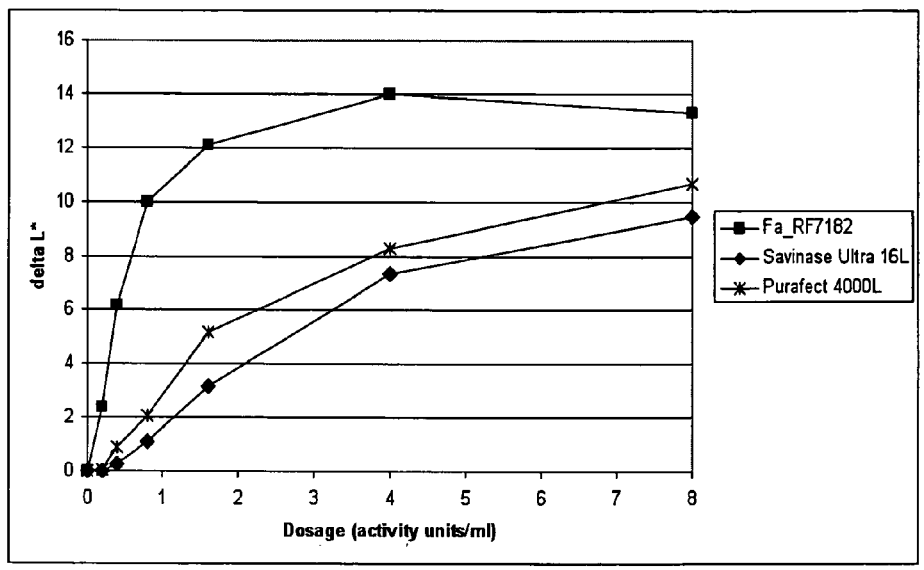
FIGS. 9A-D show the performance of recombinant protein Fa_RF7182 with blood/milk/ink stain (Art 117, EMPA) with different concentrations of liquid base detergent for coloured fabrics at 30° C. Commercial preparations Purafect® 4000L and Savinase® Ultra 16L were used for comparison. $\Delta L^*$ (deltaL*)=lightness value L* of enzyme treated fabric–lightness value L* of fabric treated with buffer only (enzyme blank).
Figure 9B:
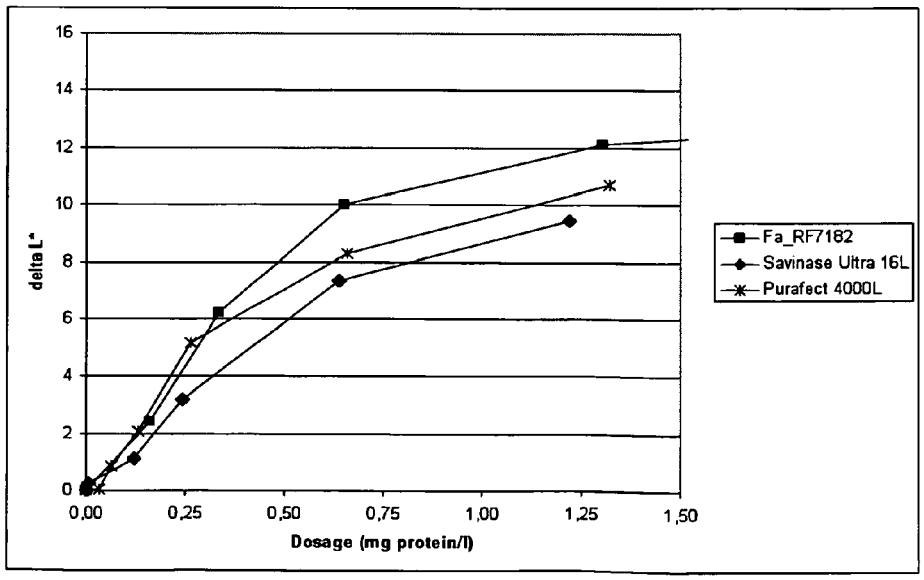
Figure 9C:
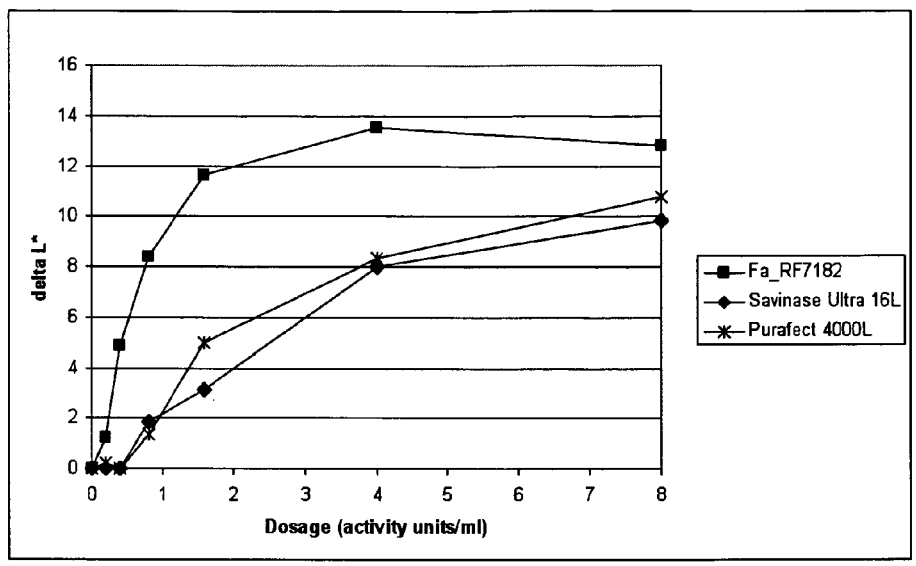
Figure 9D:
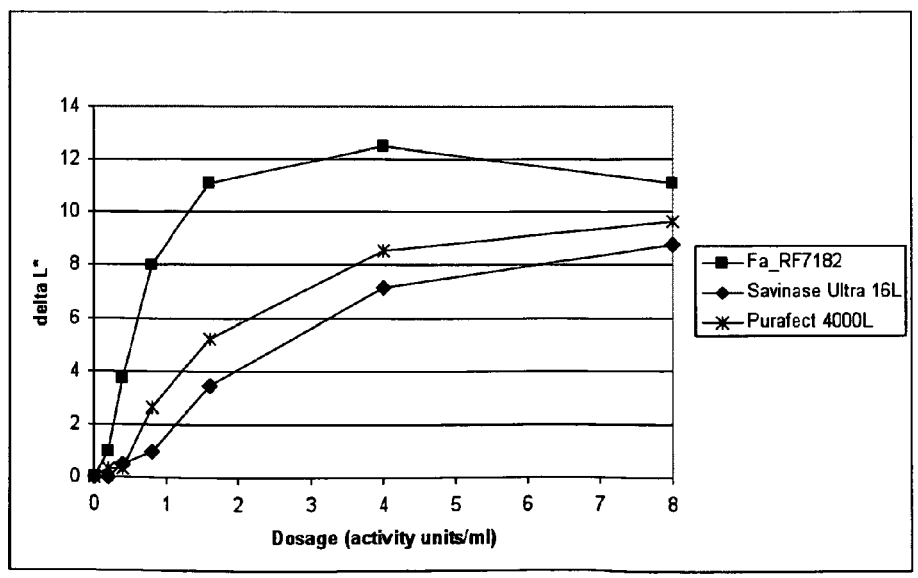
Figure 10A:
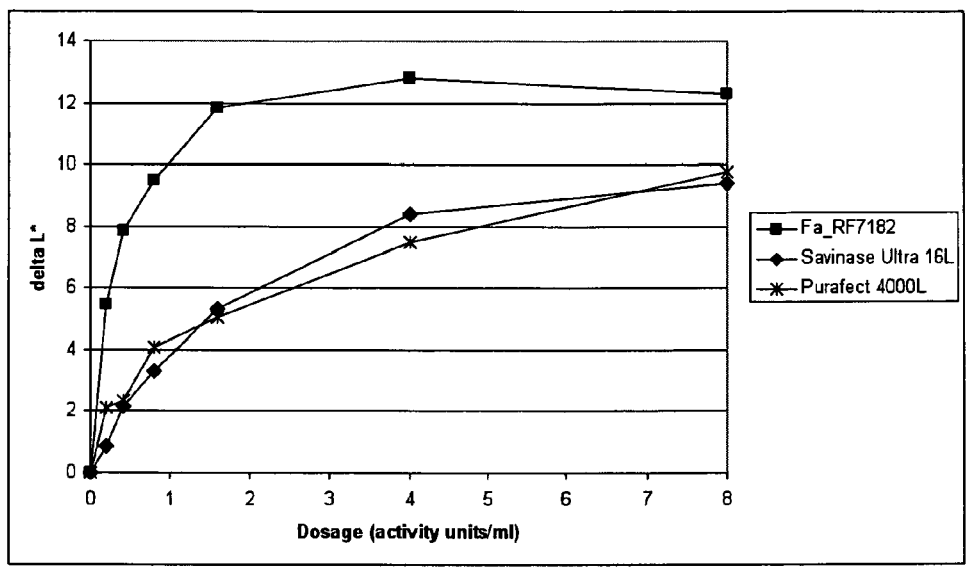
FIGS. 10A-D show the performance of recombinant protein Fa_RF7182 with blood/milk/ink stain (Art 117, EMPA) with different concentrations of Ariel sensitive (without enzymes) at 30° C. Commercial preparations Purafect® 4000L and Savinase® Ultra 16L were used for comparison. $\Delta L^*$ (deltaL*)=lightness value L* of enzyme treated fabric–lightness value L* of fabric treated with buffer only (enzyme blank).
Figure 10B:
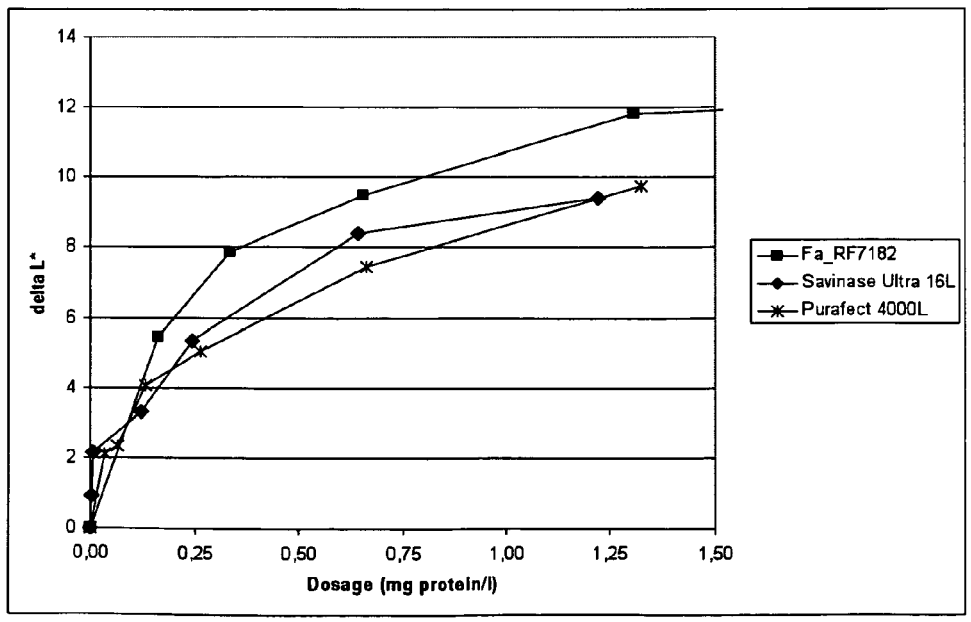
Figure 10C:
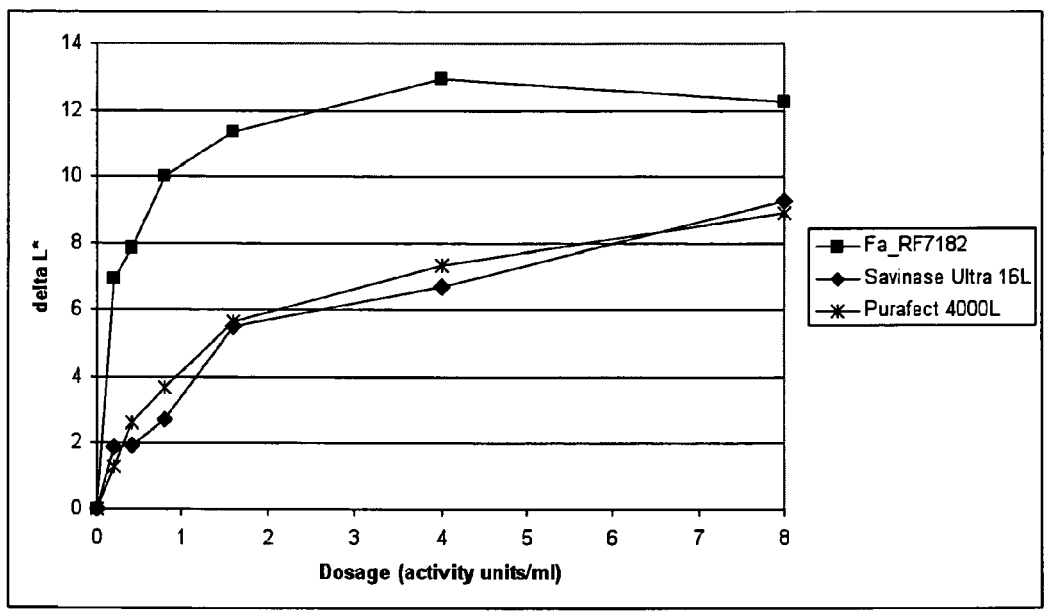
Figure 10D:
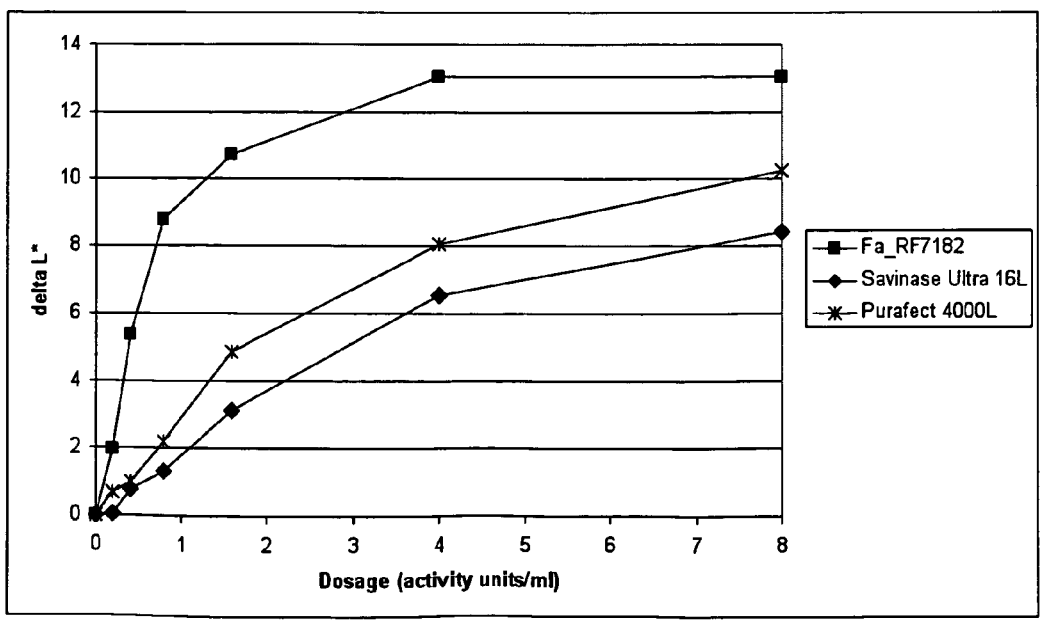
Figure 11A:
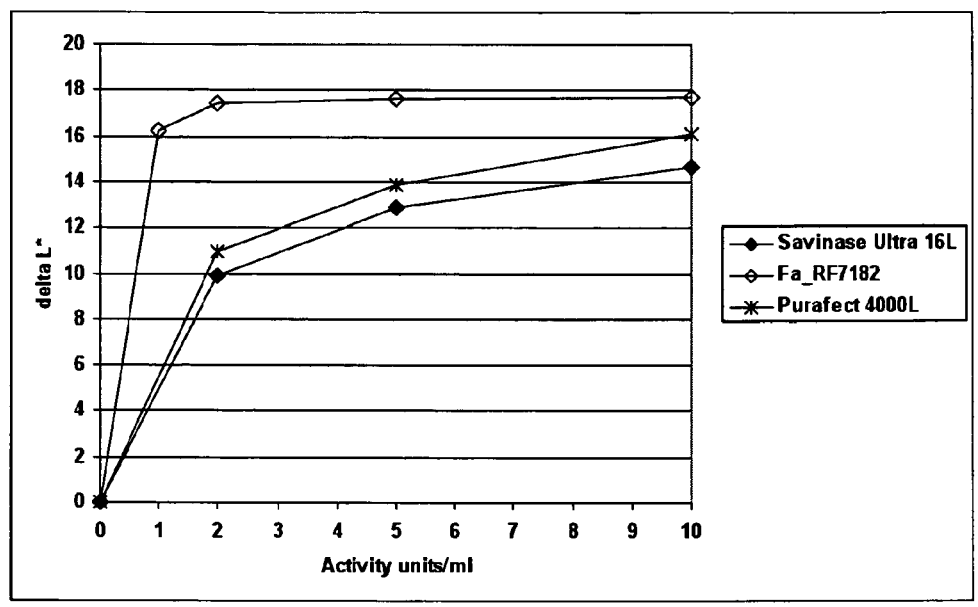
FIGS. 11A-D show the performance of recombinant protein Fa_RF7182 on different stains in Launder Ometer tests with liquid Base detergent for coloured fabrics at 30° C. Commercial preparations Savinase® Ultra 16L and Purafect® 4000L were used for comparison. ΔL* (deltaL*)=lightness value L* of enzyme treated fabric–lightness value L* of fabric treated with buffer only (enzyme blank).
Figure 11B:
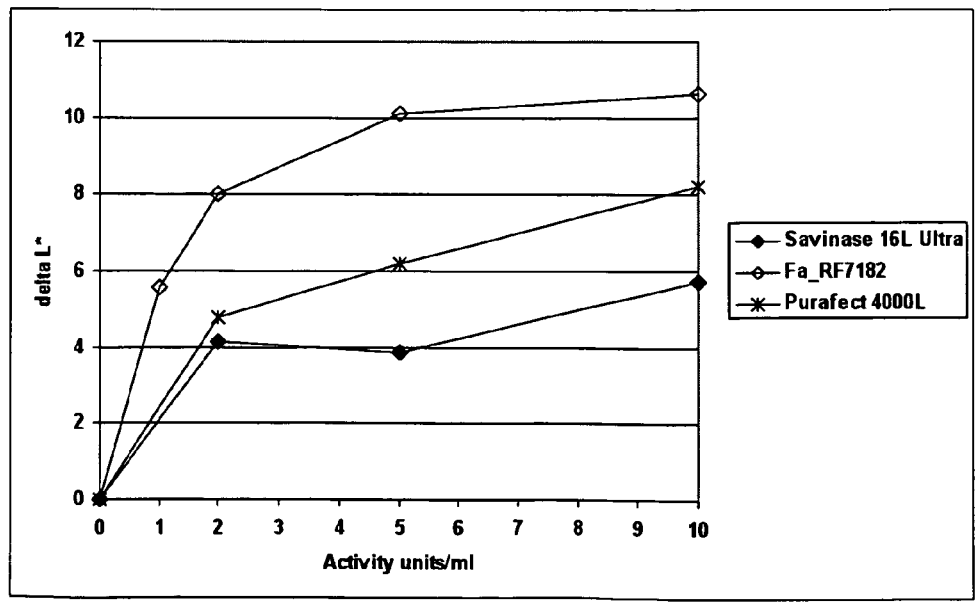
Figure 11C:
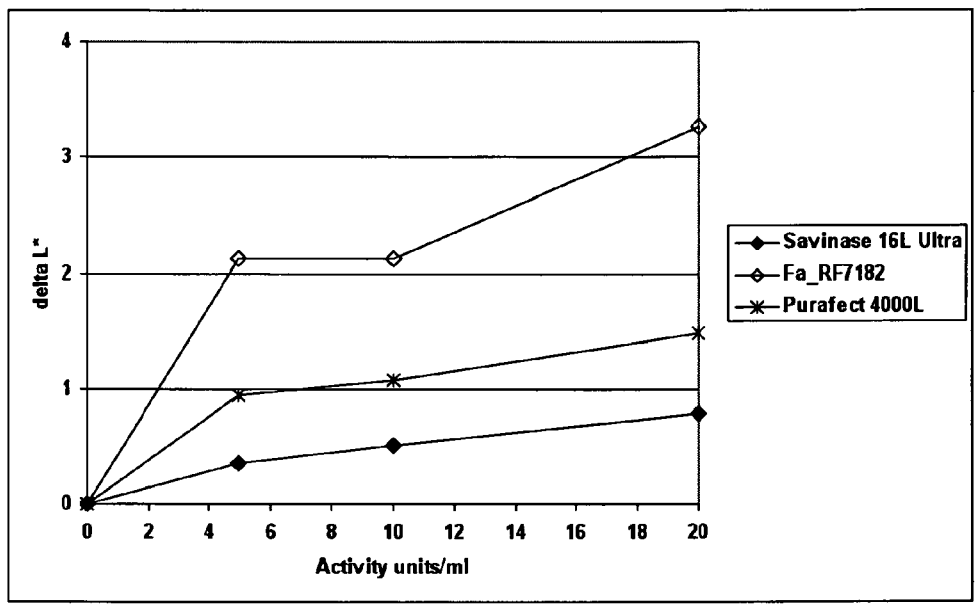
Figure 11D:
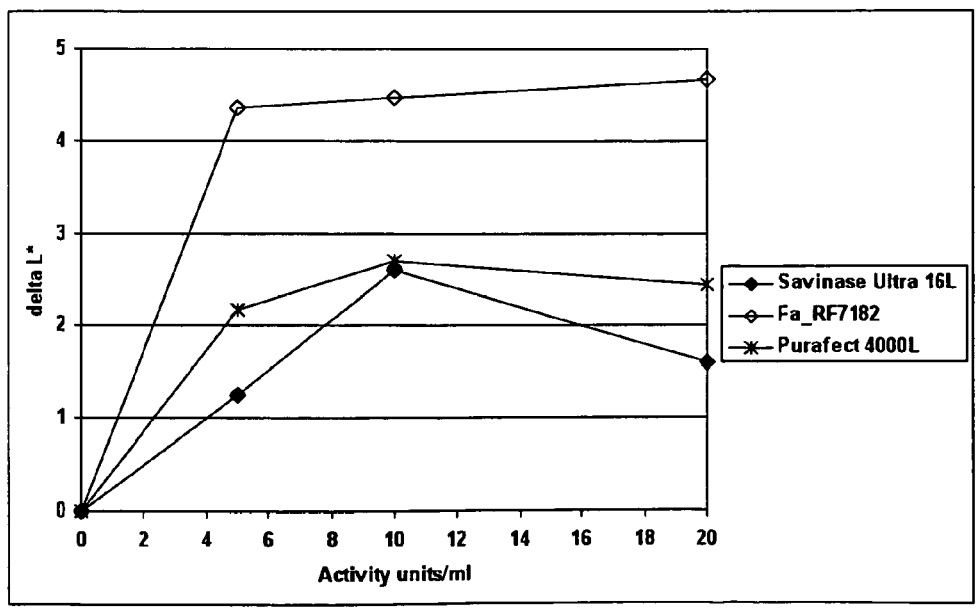
Figure 13A:
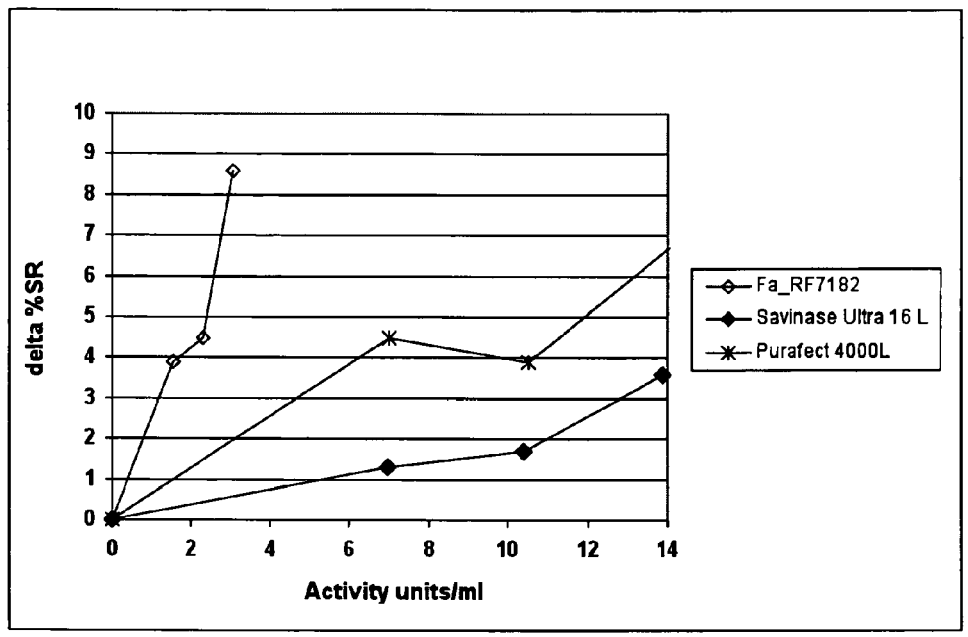
FIG. 13A shows the stain removal effect on chocolate milk/pigment/Cotton (C-03-030/CFT).
Figure 13B:
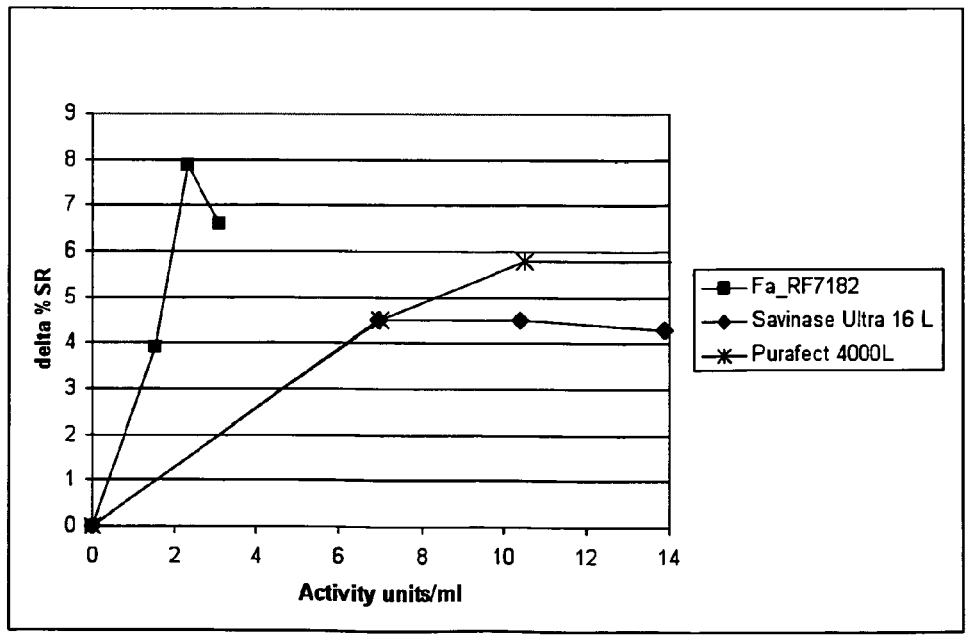
FIG. 13B shows the stain removal effect on blood/milk/ink/Cotton (C-05-059b/CFT).
Figure 13C:
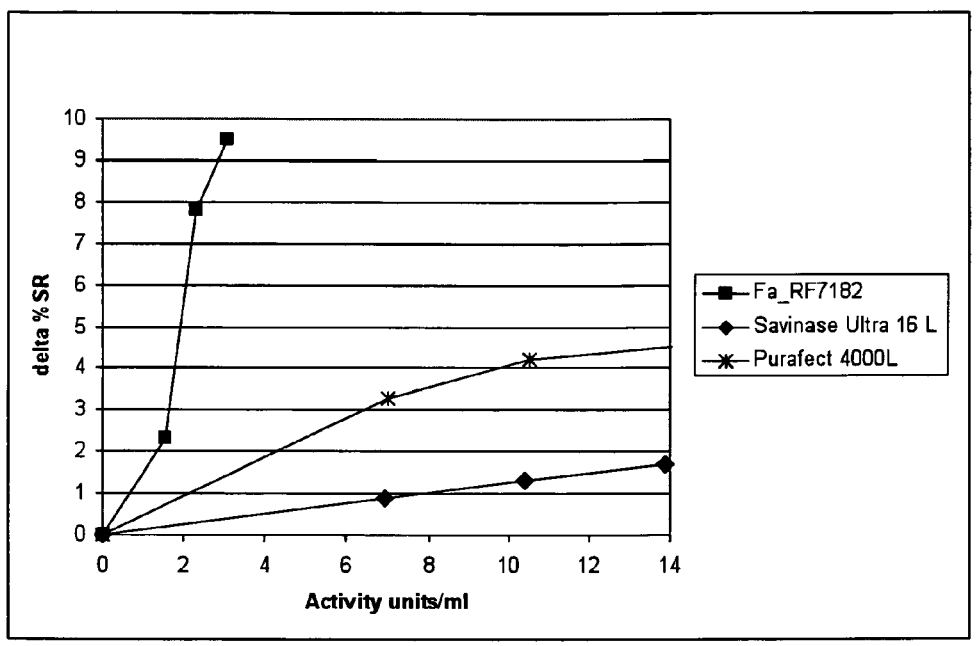
FIG. 13C shows the stain removal effect on blood/milk/ink/PE-Cotton (C-05-014/CFT).
Figure 13D:
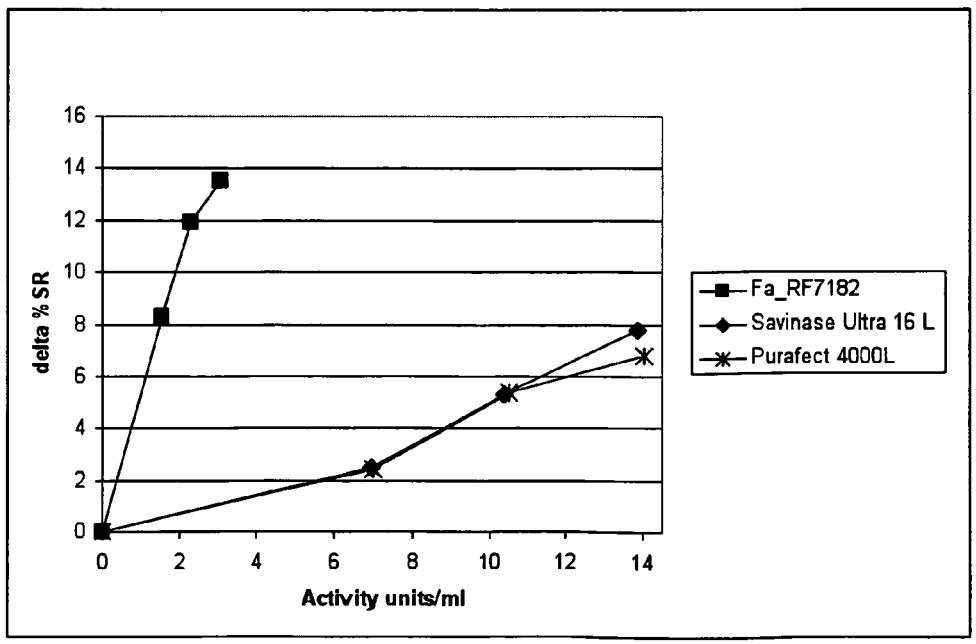
FIG. 13D shows the stain removal effect on groundnut oil/milk/Cotton (C-05-014/CFT).
Figure 13E:
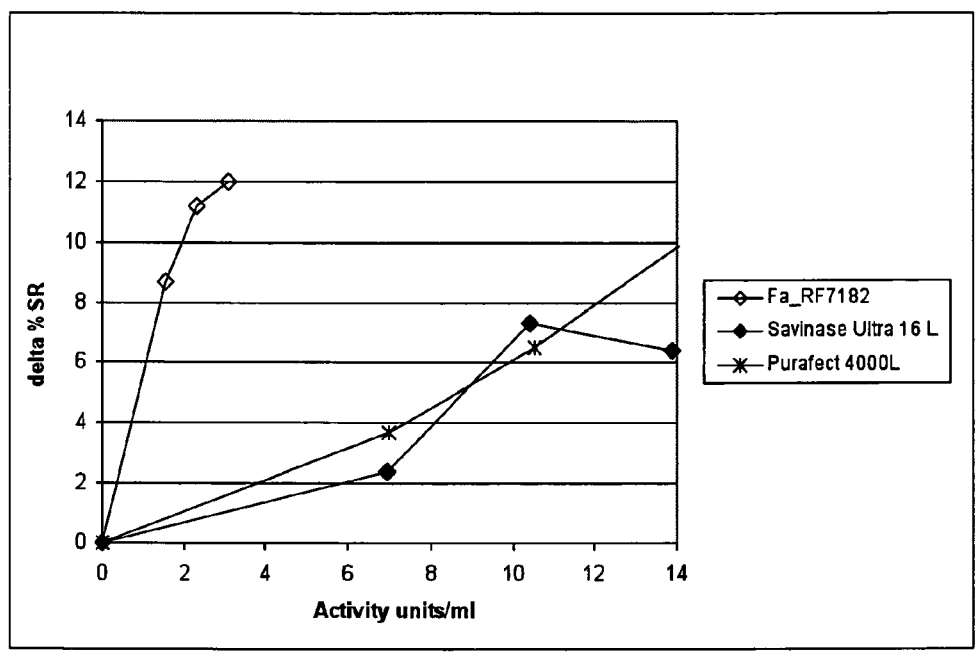
FIG. 13E shows the stain removal effect on egg Yolk/Pigment/Cotton (CS-38-010/CFT).
Figure 14A:
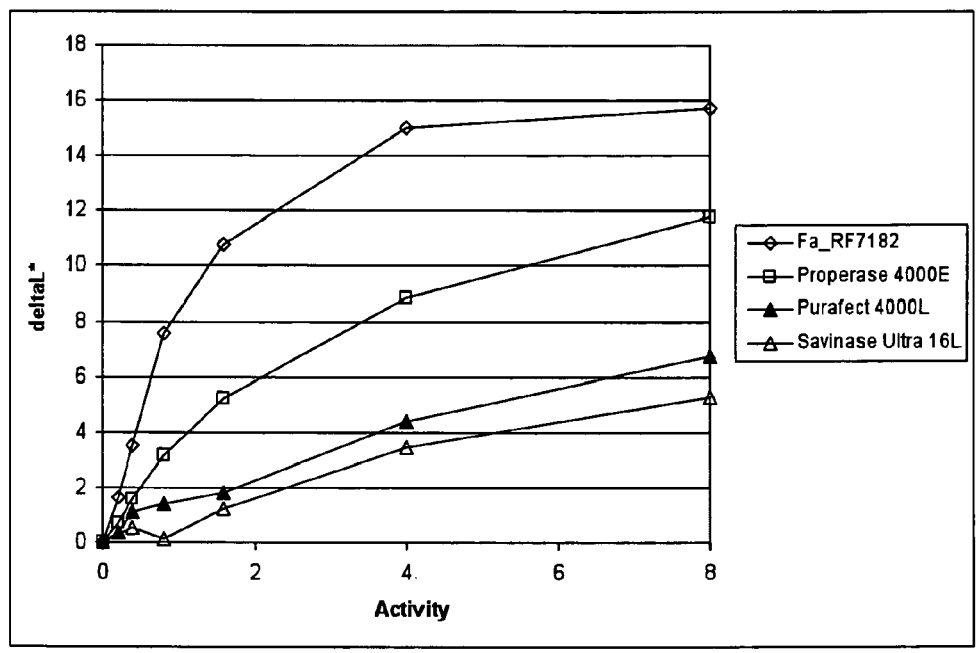
FIGS. 14A-F describe the performance of recombinant Fa_RF7182 protein with blood/milk/ink stain (Art 117, EMPA) at temperatures from 10° C. to 60° C., pH 9, 60 min. Commercial preparations Savinase Ultra® 16L (Novozymes A/S, DK), Purafect® 4000L (Genencor Inc, USA) and Properase® 4000E (Genencor Inc., USA) were used for comparison. ΔL* (deltaL*)=lightness value L* of enzyme treated fabric–lightness value L* of fabric treated with buffer only (enzyme blank).
Figure 14B:
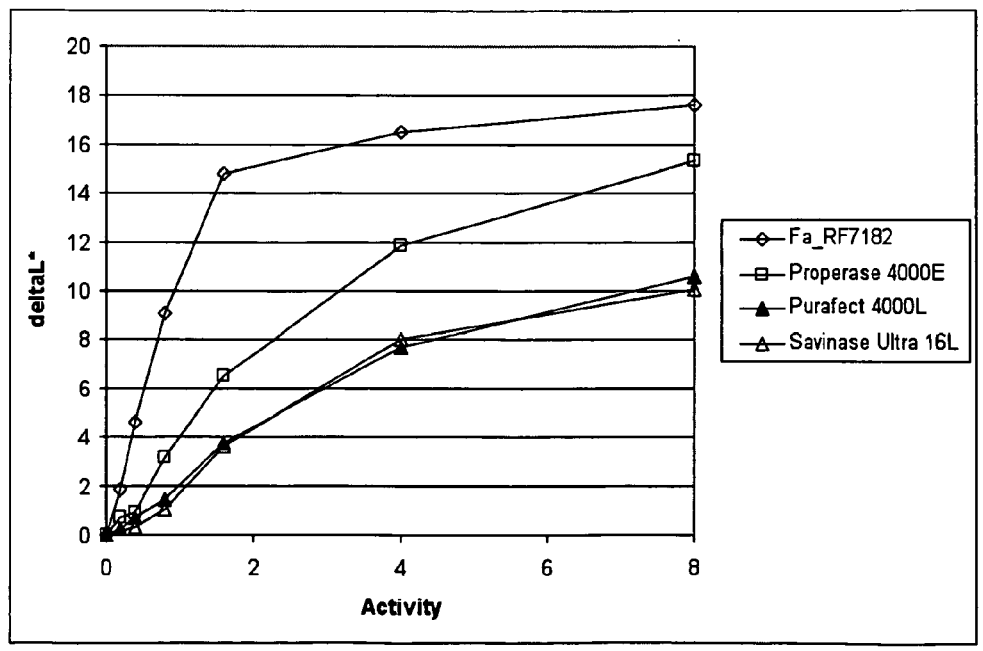
Figure 14C:
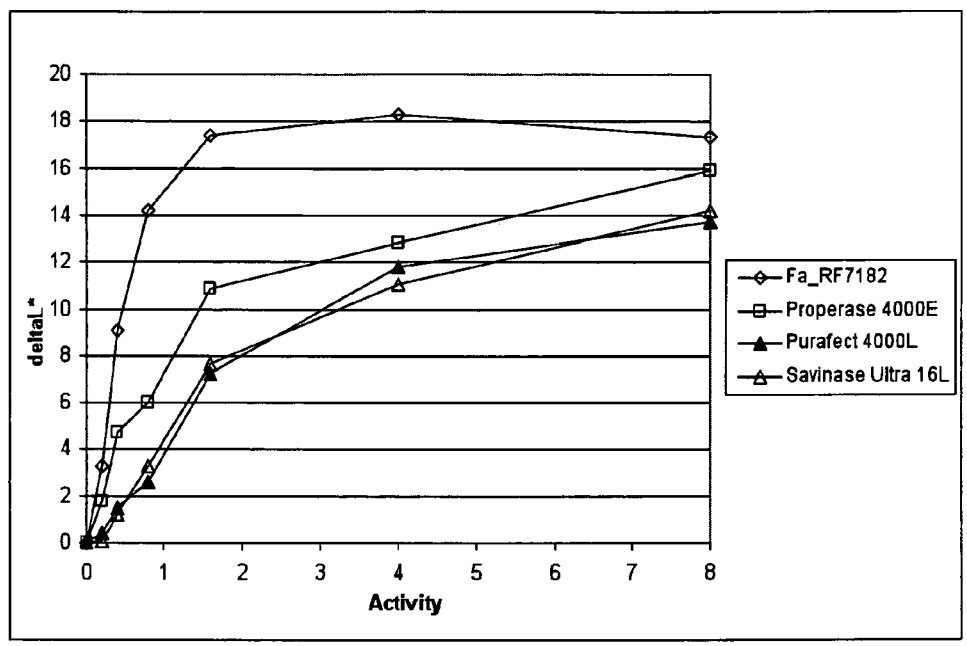
Figure 14D:
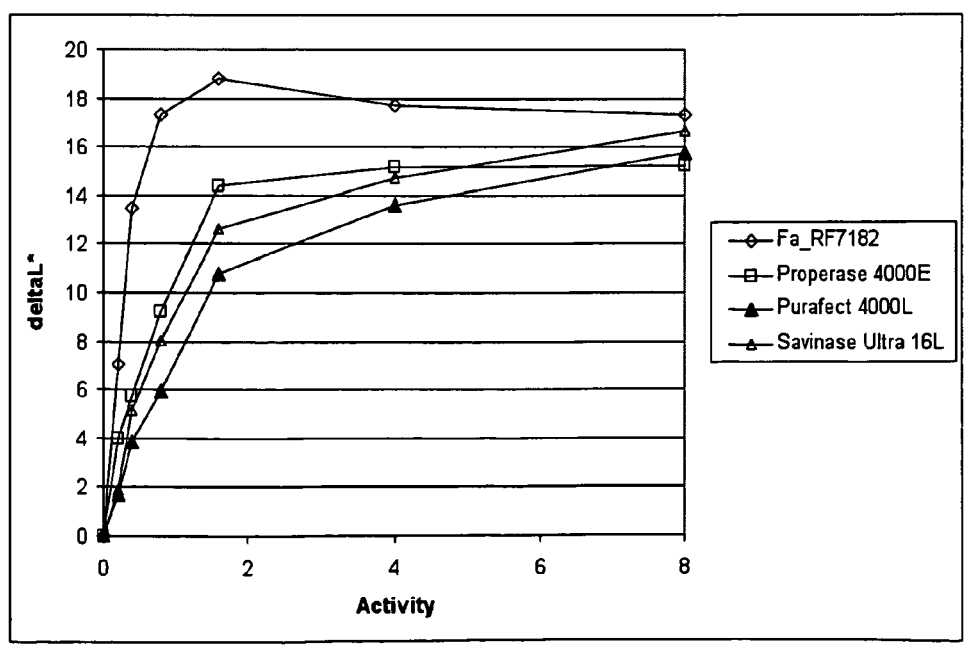
Figure 14E:
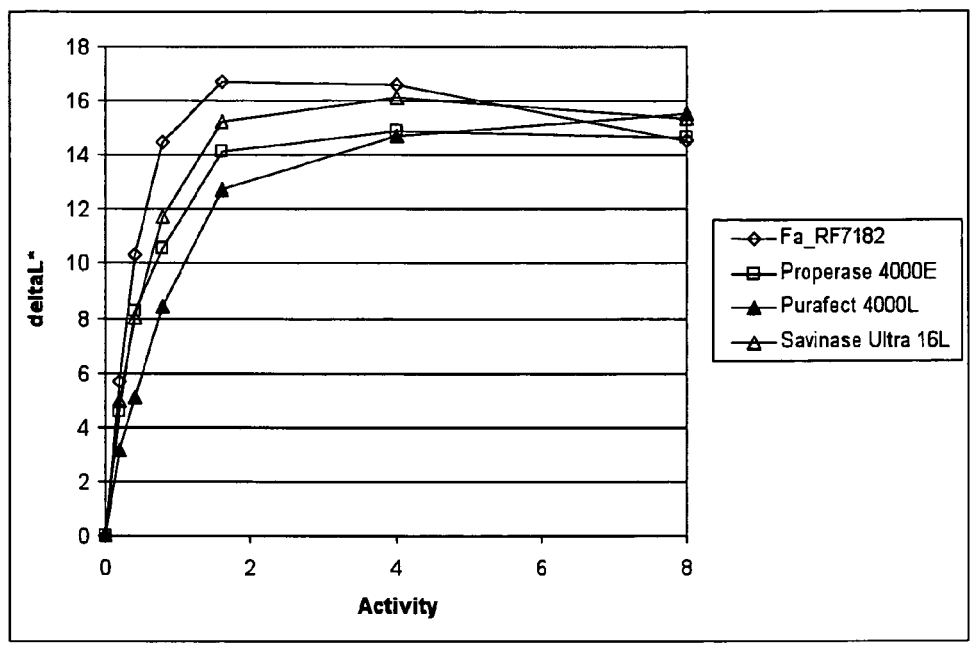
Figure 14F:
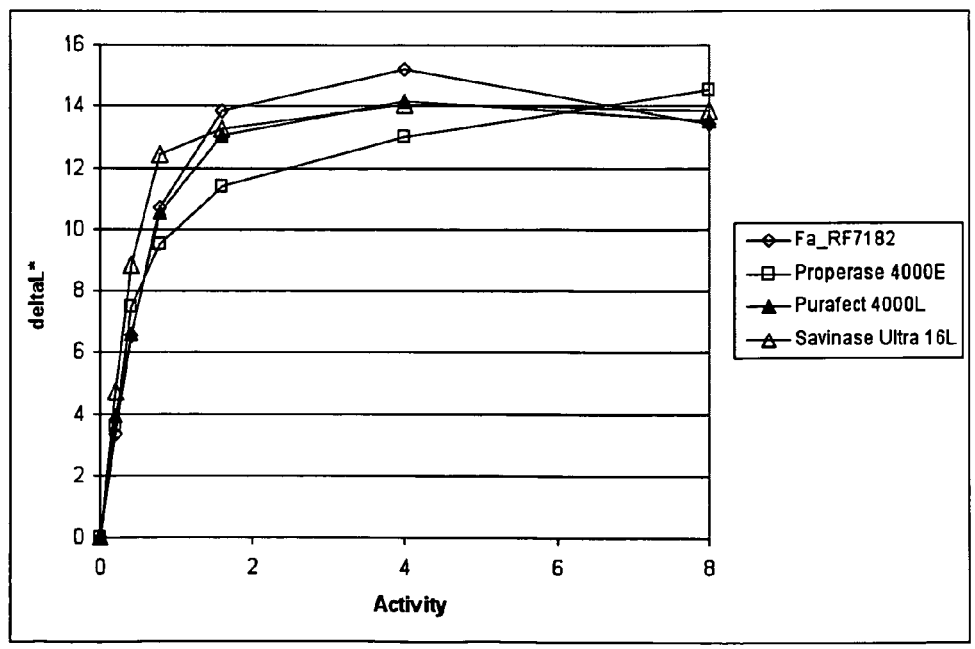

Based on the results shown in FIG. 8 Fa_RF7182 has excellent performance with liquid detergent at 40° C. The efficiency of Fa_RF7182 on blood/milk/ink/stain (polyester+cotton) was considerably higher compared to commercial preparations Purafect® 4000L and Savinase® Ultra 14 L, when same amount of protease activity was dosed. The dosage of 4-8 units of commercial enzymes per ml of liquor was equal to dosage about 0.2-0.5% of enzyme preparation per weight of detergent, which is in typical use level for detergent enzymes.

Example 9

Performance of Recombinant Protein Fa_RF7182 with Different Liquid Detergent Concentrations at 30° C.

Recombinant protein Fa_RF7182 preparation produced in *Trichoderma* (as described in Example 4) was tested for its ability to remove blood/milk/ink standard stain with liquid detergent at concentrations 1-5 g/l at 30° C. Ariel Sensitive (Procter & Gamble, England) containing no enzymes and liquid base detergent for coloured fabric containing 25% washing active substances, polyol and polymers (Table 4) were used as detergents and standard stain Art.117 (blood/milk/ink, cotton+polyester, EMPA) was used as test material. Commercial protease preparations Purafect® 4000L, Savinase® Ultra 16 L and treatment without enzyme (control) were used for comparison. Each enzyme was dosed 0, 0.2, 0.4, 0.8, 1.6, 4, and 8 activity units (µmol tyrosine/min) per ml wash liquor. Activity was measured as described in Example 6.

TABLE 4

Composition of Liquid Base detergent for colored fabric

| Ingredients | % |
|---|---|
| NaLES (sodium lauryl ether sulphate) | 4.9 |
| Nonionic C12-15 7EO (ethylene oxide) | 15 |
| Na-Soap (Palm Kernel FA) | 4.4 |
| Coco Glucoside | 1 |
| <Total Surfactant> | <25.30> |
| Polyol (Glycerin) | 5 |
| Phosphonate (32%) (ThermPhos) | 2 |
| PVP-Sokalan HP 53 (BASF) | 1 |
| Sokalan PA 15 (BASF) | 1.56 |
| Sorez-100 (ISP) | 0.4 |
| Water up to 100% | |

Amounts of 1, 3.3 and 5 g of liquid detergent was dissolved in 1 liter of tap water (dH≤4), mixed well with magnetic stirrer and tempered to 30° C. The pH in the wash liquors was ca. 7.3-7.5 with Base detergent or ca. 7.6-8.0 with Ariel, depending on detergent concentration. Stain fabric was cut into pieces like described in Example 6. Swatches were placed in wells of microtiter plates (Nunc 150200) and 1.5 ml wash liquor containing detergent and enzyme dilution in water (below 70 µl) was added on top of the fabric. The plates with samples were in incubated in a horizontal shaker at 30° C. for 60 min with 125 rpm. After that the swatches were carefully/thoroughly rinsed under warm running water and dried overnight at indoor air, on a grid, protected against daylight.

The colour of the swatches after treatment was measured with Minolta CM 2500 spectrophotometer using L*a*b* color space coordinates and stain removal effect calculated as ΔL* as described in example 6.

Results obtained with base detergent for coloured fabrics are shown in FIGS. 9 A-D and results obtained with Ariel Sensitive are shown in FIG. 10 A-D. The efficiency of Fa_RF7182 on blood/milk/ink stain was considerably higher compared to commercial preparations Purafect® 4000L and Savinase® Ultra 14 L with both detergents and at all detergent concentrations, when same amount of activity was dosed. Also if dosing is calculated as amount of added protein (FIGS. 9B and 10B), the stain removal efficiency is highest with Fa_RF7182. The amount of protein from the enzyme preparations was determined by Bio-Rad protein assay (Bio-Rad Laboratories, Hercules, Calif.) using bovine gamma-globulin (Bio-Rad) as standard. Results of these tests indicate that Fa_RF7182 protease has excellent performance with liquid detergents at low temperatures, like 30° C.

Example 10

Efficiency of Recombinant Protein Fa_RF7182 on Different Stains with Liquid Detergent at 30° C. (Launder Ometer)

Recombinant protein Fa_RF7182 preparation produced *Trichoderma* (as described in Example 4) was tested for its ability to remove different stains with liquid detergent at 30° C. and compared to commercial protease preparations Purafect® 4000L and/or Savinase® Ultra 16 L. The following artificially soiled test cloths from EMPA were used: blood/milk/ink Art.117 (polyester+cotton), blood/milk/ink Art.116 (cotton), grass Art. 164 and cocoa Art.112. The fabric was cut in 9 cm×12 cm swatches and the edges were neated by zig-zag stitches. Detergent was the same as described in example 9.

Stain removal treatments were performed in LP-2 Launder Ometer as follows. Launder Ometer was first preheated to 30° C. 450 ml of tempered wash liquor containing 5 g detergent per liter tap water (dH≤4) and enzyme dilution was added in containers containing stains Art. 116 and 117 or stains Art. 164 and Art. 112. Enzymes were dosed 0, 1 and/or 2, 5, 10 activity units (µmol tyrosine/min) per ml wash liquor with blood/milk/ink stains and 0, 5, 10 and 20 activity units (µmol tyrosine/min) per ml wash liquor with grass and cocoa. Activity was measured as described in Example 6. The Launder Ometer was run at 30° C. for 60 min ca. pH 7.5. After that the swatches were carefully rinsed under running water (ca. 20° C.) and dried overnight at indoor air, on a grid, protected against daylight.

The colour of the swatches after treatment was measured with Minolta CM 2500 spectrophotometer using L*a*b* color space coordinates and stain removal effect calculated as ΔL* as described in example 6. Each value was the average of at least 20 measurements per swatch. The measurements were avoided from areas with crease marks formed during the treatment because of the folding of the fabric (in cotton stains Art. 116 and Art. 112).

Results obtained with base detergent (5 g/l) for coloured fabrics (FIGS. 11 A-D) showed that efficiency on blood/milk/ink, grass and cocoa stains was considerably higher with Fa_RF7182 compared to commercial preparations Savinase® Ultra 16L and Purafect® 4000 L at 30° C. when same amount of protease activity was dosed. The dosage of 10 units of commercial enzymes per ml of was liquor was equal to dosage approximately 0.4% of enzyme preparation per weight of detergent, which is in typical use level for detergent enzymes. Results of these tests indicate that Fa_RF7182 protease is efficient on several stains at low temperatures like 30° C.

Example 11

Evaluation of the Performance of the Recombinant Protein Fa_RF7182 in Liquid Laundry Detergent 30° C. in Full Scale Trials The performance of recombinant protein Fa_RF7182 preparation produced *Trichoderma* (as described in Example 4) was tested in liquid detergent in full scale in a washing machine at 30° C. and compared to commercial protease preparations Purafect® 4000L and Savinase® Ultra 16L and treatment with detergent without enzyme. Liquid base detergent for coloured fabrics, as described in Example 9, and 8 different protease sensitive tracers (Table 5) were used. In addition two pieces of ballast soil (CFT-SBL) per wash were placed in wash net to avoid contamination by contact with the other swatches. Tracers were from CFT (Center For Testmaterials BV, The Netherlands). Stain swatches 10 cm×10 cm were stitched to kitchen towels. The process parameters and conditions are described in Table 6. Enzyme dosages used in the trials were calculated both as enzyme activities (ca. 0-14 activity units per ml wash liquor) and as amount of protein (ca. 0-2.5 mg per liter wash liquor). Protease activities and protein contents of the preparations were measured as described in Examples 6 and 9.

TABLE 5

Protease sensitive tracers used in test.

| Nr. | Monitor/Swatch | Substrate |
|---|---|---|
| 1 | CFT/CS-01-106 | Blood (aged)/Cotton |
| 2 | CFT/C-03-030 | Chocolate milk/pigment/Cotton |
| 3 | CFT/CS-05-059b | Bood/milk/ink/Cotton |
| 4 | CFT/PC-05-014 | Blood/Milk/Ink/PE-Cotton |
| 5 | CFT/CS-08-069 | Grass/Cotton |
| 6 | CFT/C-10-186b | Groundnut oil/milk/Cotton |
| 7 | CFT/CS-25-016 | Spinach/Cotton |
| 8 | CFT/CS-38-010 | Egg Yolk/Pigment/Cotton |

TABLE 6

Process parameters and conditions

| Machine | Miele N-Tronic Frontstar |
|---|---|
| Program | 30° C., short program |
| Hardness of water | about 11.2° dH with 13 liter intake |
| Ballast Load | 2.5 kg bed sheets/bath towels, and kitchen towels |
| Detergent dosage | 80 g/machine load |
| Amount of each tracers | 2 stain trips 10 cm × 10 cm per machine |
| Number of washes | 2 |

Evaluation of stain removal effect was based on measurement of reflectance (remission), R 457 nm, with Datacolor-spectrophotometer with an UV-filter and calculated as percentage stain removal effect (% SR):

$$\%SR = \frac{\text{Reflectance after washing} - \text{Reflectance before washing} \times 100\%}{\text{Reflectance of unsoiled fabric} - \text{Reflectance before washing}}$$

Results were calculated as Δ% SR (delta % SR), which means % SR of enzyme treated fabric minus % SR of treatment without enzyme (detergent only).

Two washes containing two swatches of each stain were performed with each dosage of enzyme and three measurements were measured of each stain swatch, so the values are based upon the 12 measurements per stain per product.

The results of total soil removal efficiencies (delta % SR) are shown in FIGS. 12A-B and FIGS. 13 A-E. The total stain removal effect based on the sum of the results obtained with the eight different protease sensitive stains (Stains 1-8, Table 5) was considerably higher with Fa_RF7182 compared to commercial protease preparations Purafect® 4000L and Savinase® Ultra 16L, when proteases were dosed as amount of activity (FIG. 12A). Fa_RF7182 was efficient especially on blood/milk/ink, chocolate/milk, groundnut oil/milk and egg yolk (FIGS. 13A-E).

A general detergency tracer (pigment/oil) was used as a control in repeats in different machines. No differences between the various tests were observed.

Example 12

Performance of Recombinant Protein Fa_RF7182 in pH 9 Buffer at Temperatures from 10° C. to 60° C.

Recombinant protein Fa_RF7182 produced in Trichoderma (as described in Example 4) was tested for its ability to remove blood/milk/ink standard stain (Art.117, polyester+cotton, EMPA Testmaterialen AG, Swizerland) at temperatures from 10° C. to 60° C. Commercial protease preparations Savinase® Ultra 16 L, Purafect® 4000 L and Properase® 4000 E and treatment without enzyme (control) were used for comparison. The tests were performed at pH 9 buffer as described in Example 6, except the incubation temperature range was broader, stain material was different and the temperature of the rinsing water of the swatches was similar to washing temperature. The colour of the swatches after treatment was measured with Minolta CM 2500 spectrophotometer using L*a*b* color space coordinates and stain removal effect calculated as ΔL* as described in Example 6.

The results are shown in FIGS. 14A-F. Fa_RF7182 protease preparation showed considerably higher stain removal capacity especially at the lowest temperatures from 10° C. to 40° C. in pH 9 buffer, compared to commercial protease preparations Savinase® Ultra 16L and Purafect® 4000L and Properase® 4000 E.

Example 13

Performance of Recombinant Protein Fa_RF7182 with Liquid Detergent at Cold Washing Temperatures (10° C. And 20° C.)

Recombinant protein Fa_RF7182 produced in Trichoderma (as described in Example 2) was tested for its ability to remove blood/milk/ink standard stain (Art.117, cotton+polyester, EMPA) with Liquid Base detergent at low temperatures. The testing method was similar to Example 9, except only detergent concentration of 3.3 g/l and lower incubation temperatures, 10° C. and 20° C., were used. The temperature of the rinsing water of the swatches was similar to washing temperature.

The colour of the swatches after treatment was measured with Minolta CM 2500 spectrophotometer using L*a*b* color space coordinates and stain removal effect calculated as ΔL* as described in Example 6. For treatment without enzyme (enzyme blank), detergent solution was used as washing liquor.

Figure 15A:
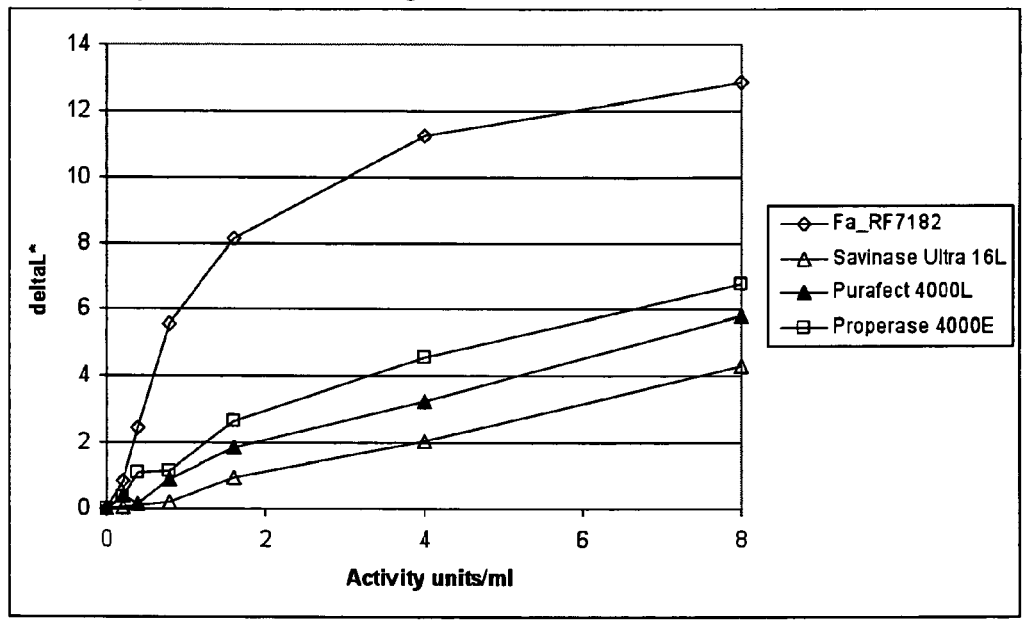
FIGS. 15A and 15B show the performance of recombinant Fa_RF7182 protein with blood/milk/ink stain (Art 117, EMPA) and Liquid Base concentration of 3.3 g/l at 10° C. and 20° C. Commercial preparations Savinase® Ultra 16L, Purafect® 4000L and Properase® 4000 E were used for comparison. ΔL* (deltaL*)=lightness value L* of enzyme treated fabric–lightness value L* of fabric treated with buffer only (enzyme blank).
Figure 15B:
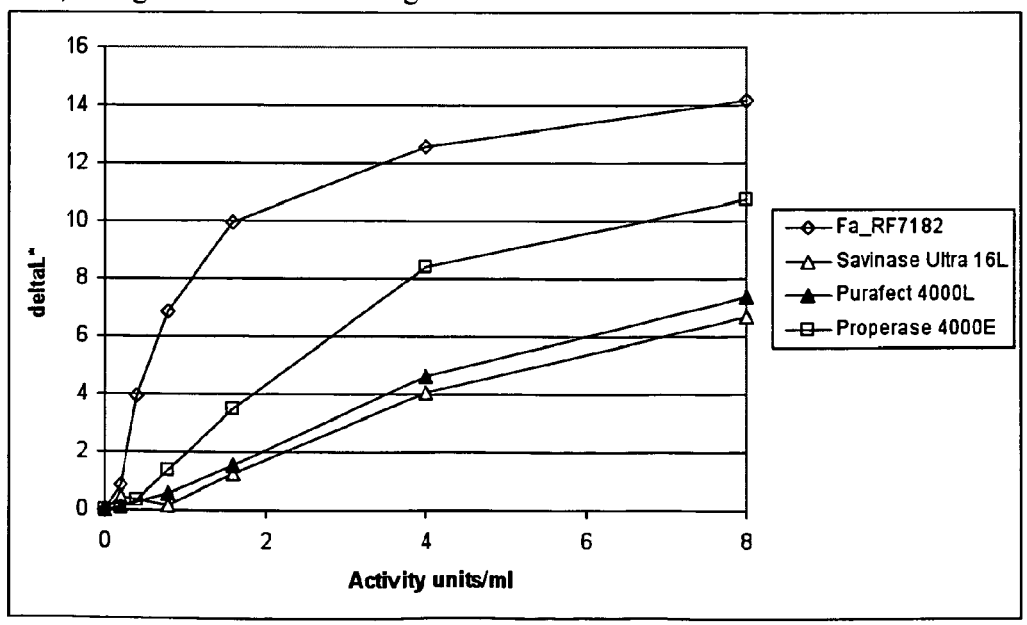

Results obtained with Liquid Base detergent concentration of 3.3 g/l at 10° C. and 20° C. are shown in FIGS. 15A and B. The efficiency of Fa_RF7182 on blood/milk/ink stain was considerably higher both at 10° C. and 20° C. compared to commercial preparations Savinase® Ultra 16L, Purafect® 4000L and Properase® 4000E, when same amount of activity was dosed. Results of these tests indicate that Fa_RF7182 protease has excellent performance with liquid detergents at very low washing temperatures.

REFERENCES

Altschul S F, W Gish, W Miller, E W Myers and D J Lipman. 1990. Basic local alignment search tool. J. Mol. Biol. 215: 403-410.

AMFEP, 2007. Association of Manufacturers and Formulators of Enzyme products, List of commercial enzymes at amfep.org/list.html (updated 30 Nov. 2007).

Anwar A and M Saleemuddin. 1998. Alkaline proteases: A review. Bioresource Technol. 64:175-183.

Chen, Y-J, and M Inouye, 2008. The intramolecular chaperone-mediated protein folding. Curr. Opin. Struct. Biol. 18: 765-770.

Cherry, J. R., and Fidantsef, A. L. 2003. Directed evolution of industrial enzymes: an update. Curr. Opin. Biotechnol. 14: 438-443.

Edman P and G Begg. 1967. A protein sequenator. Eur. J. Biochem. 1:80-91.

Gasteiger, E, A Gattiker, C Hoogland, I Ivanyi, R D Appel and A Bairoch. 2003. ExPASy: the proteiomics server for in-depth protein knowledge and analysis. Nucleic Acids Res. 31:3784-3788.

Geremia R A, Goldman G H, Ardiles W, Vila S B, Van Montagu M, Herrera-Estrella A. 1993) Molecular characterization of the proteinase-encoding gene, prb1, related to mycoparasitism by *Trichoderma harzianum*. Mol. Microbiol. 8(3):603-613.

Gupta, R, Q K Beg, S Khan and B Chauhan. 2002. An overview on fermentation, downstream processing and properties of microbial alkaline protease. Appl. Microbiol. Biotechnol. 60: 381-395.

Gurr, S J, Uncles, S E, and Kinghorn J R. 1987. The structure and organization of nuclear genes in filamentous fungi. pp 93-139. In (J R Kinghorn, ed.) Gene Structure in Eukaryotic Microbes. IRL Press, Oxford.

Joutsjoki, V V, T K Torkkeli, and K M H Nevalainen. 1993. Transformation of *Trichoderma reesei* with the *Hormoconis resinae* glucoamylase P (gamP) gene: production of a heterologous glucoamylase by *Trichoderma reesei*. Curr. Genet. 24:223-228.

Kalisz H M. 1988. Microbial proteinases. Adv. Biochem. Eng. Biotechnol. 36:1-65.

Karhunen T, A Mantyla, K M H Nevalainen, and P L Suominen. 1993. High frequency one-step gene replacement in *Trichoderma reesei*. I. Endoglucanase I overproduction. Mol. Gen. Genet. 241:515-522.

Laemmli U K. 1970. Cleavage of structural proteins during assembly of the head of bacteriophage T4. Nature 227:680-685.

Malardier L, M J Daboussi, J. Julien, F Roussel, C. Scazzocchio and Y Brygoo. 1989. Cloning of the nitrate reductase gene (niaD) of *Aspergillus nidulans* and its use for transformation of *Fusarium oxysporum*. Gene 78:147-156.

Maurer, K-H. 2004. Detergent proteases. Curr. Opin. Biotechnol. 15: 330-334.

Nielsen H, J Engelbrecht, S Brunak and G von Heijne. 1997. Identification of prokaryotic and eukaryotic signal peptides and prediction of their cleavage sites. Protein Engineering 10:1-6.

Nielsen H and A Krogh. 1998. Prediction of signal peptides and signal anchors by a hidden Markov model. In: Proceedings of the Sixth International Conference on Intelligent Systems for Molecular Biology (ISMB 6), AAAI Press, Menlo Park, Calif., pp. 122-130.

Paloheimo M, A Mäntylä, J Kallio, and P Suominen. 2003. High-yield production of a bacterial xylanase in the filamentous fungus *Trichoderma reesei* requires a carrier polypeptide with an intact domain structure. Appl. Env. Microbiol. 69:7073-7082.

Penttilä M, H Nevalainen, M Rättö, E Salminen, and J Knowles. 1987. A versatile transformation system for the cellulolytic filamentous fungus *Trichoderma reesei*. Gene 61:155-164.

Poutanen, M, L Salusjarvi, L Ruohonen, M Penttilä and N Kalkkinen. 2001. Use of matrix-assisted laser desorption/ionization time-of-flight mass mapping and nanospray liquid chromatography/electrospray ionization tandem mass spectrometry sequence tag analysis for high sensitivity identification of yeast proteins separated by two-dimensional gel electrophoresis. Rapid Commun. Mass Spectrom. 15: 1685-1692

Raeder U and P Broda. 1985. Rapid preparation of DNA from filamentous fungi. Lett. Appl. Microbiol. 1:17-20.

Rao M B, A M Tanksale, M S Ghatge and V V Deshpande. 1998. Molecular and biotechnological aspects of microbial proteases. Microbiol. Mol. Biol. Rev. 62:597-635.

Sambrook J and D W Russell. 2001. Molecular cloning, a laboratory manual. Cold Spring Harbor Laboratory, New York, U S.

Shevchenko, A, M. Wilm, O. Vorm, M Mann. 1996. Mass spectrometric sequencing of proteins from silver-stained polyacrylamide gels. Anal Chem. 68: 850-858.).

Shimogaki H, K Takenchi, T Nishino, M Ohdera, T Kudo, K Ohba, M V Iwama and M Irie. 1991. Purification and properties of a novel surface protease from *Bacillus* sp. Y. Agric. Biol. Chem. 55:2251-2258.

Suarez M B, Vizcaino J A, Lobell A, and Monte E. 2007. Characterization of genes encoding novel peptidases in the biocontrol *Trichoderma harzianum* CECT 2413 using the TrichoEST functional genomics approach. Curr. Genet. 51(5):331-342.

The invention claimed is:

1. An expression vector, comprising a nucleic acid sequence selected from the group consisting of:
   (a) a nucleic acid sequence encoding a polypeptide exhibiting the serine protease specificity of SEQ ID NO:18 and comprising the amino acid sequence set forth in SEQ ID NO:18;
   (b) a nucleic acid sequence encoding a polypeptide that comprises an amino acid sequence that exhibits serine protease activity and is at least 92% identical to the amino acid sequence set forth in SEQ ID NO:18, wherein sequence identity is determined using ClustalW alignment using matrix: BLOSUM, Gap Open: 10, and Gap Extension: 0.5, and wherein the amino acid sequence that exhibits serine protease activity has the serine protease specificity of SEQ ID NO:18;
   (c) a cDNA sequence comprising the coding sequence of the nucleotide sequence set forth in SEQ ID NO:13, wherein the polypeptide encoded by the coding sequence, in its mature form, exhibits the serine protease specificity of SEQ ID NO:18;
   (d) a cDNA sequence comprising the coding sequence of the nucleotide sequence set forth in SEQ ID NO:15, wherein the polypeptide encoded by the coding sequence, in its mature form, exhibits the serine protease specificity of SEQ ID NO:18;
   (e) a cDNA sequence comprising the coding sequence of the nucleotide sequence set forth in SEQ ID NO:17, wherein the polypeptide encoded by the coding sequence exhibits the serine protease specificity of SEQ ID NO:18;
   (f) a cDNA sequence comprising the coding sequence of the nucleotide sequence in plasmid pALK2531 contained in the E. coli strain DSM 22209, wherein the coding sequence encodes a polypeptide, which in its mature form, exhibits the serine protease specificity of SEQ ID NO:18;
   (g) a nucleic acid sequence the coding sequence of which differs from the coding sequence of the nucleotide sequence of any one of (c) to (f) due to the degeneracy of the genetic code;
   (h) a nucleic acid sequence comprising the nucleotide sequence set forth in SEQ ID NO:15 fused at its 5' end to the nucleotide sequence of a heterologous signal sequence, SEQ ID NO:15 encoding a polypeptide, which in its mature form, exhibits serine protease activity; and
   (i) a nucleic acid sequence that hybridizes under stringent conditions with the complement of the nucleic acid

59 sequence set forth in SEQ ID NO:12 contained in DSM 22208 and encodes a polypeptide comprising an amino acid sequence that exhibits the serine protease specificity of SEQ ID NO:18 and is at least 92% identical to the full-length amino acid sequence set forth in SEQ ID NO:18, wherein sequence identity is determined using ClustalW alignment using matrix: BLOSUM, Gap Open: 10, and Gap Extension: 0.5, and wherein stringent conditions comprise hybridization in a solution comprising 6×SSC, 5×Denhardt's reagent, and 0.5% SDS at 65° C., and washing twice for 15 minutes at 65° C. in a solution comprising 0.1×SSC and 0.1% SDS.

2. A nucleic acid molecule, comprising a nucleic acid sequence selected from the group consisting of:
 (a) a cDNA sequence comprising the coding sequence of the nucleotide sequence set forth in SEQ ID NO:13, wherein the polypeptide encoded by the coding sequence, in its mature form, exhibits serine protease activity;
 (b) a cDNA sequence comprising the coding sequence of the nucleotide sequence set forth in SEQ ID NO:15, wherein the polypeptide encoded by the coding sequence, in its mature form, exhibits the serine protease specificity of SEQ ID NO:18;
 (c) a cDNA sequence comprising the coding sequence of the nucleotide sequence set forth in SEQ ID NO:17, wherein the polypeptide encoded by the coding sequence exhibits the serine protease specificity of SEQ ID NO:18;
 (d) a cDNA sequence comprising the coding sequence of the nucleotide sequence set forth in SEQ ID NO:13 in plasmid pALK2531 contained in the *E. coli* strain DSM 22209, wherein the coding sequence encodes a polypeptide, which in its mature form, exhibits the serine protease specificity of SEQ ID NO:18;
 (e) a cDNA sequence the coding sequence of which differs from the coding sequence of the nucleotide sequence of any one of (a) to (d) due to the degeneracy of the genetic code; and
 (f) a cDNA sequence comprising the coding sequence of the nucleotide sequence set forth in SEQ ID NO:15 fused at its 5' end to the nucleotide sequence of a heterologous signal sequence, the coding sequence encoding a polypeptide, which in its mature form, exhibits the serine protease specificity of SEQ ID NO:18.

3. The nucleic acid molecule of claim 2, wherein the nucleic acid sequence is a cDNA sequence comprising the coding sequence of the nucleotide sequence set forth in SEQ ID NO:13, wherein the polypeptide encoded by the coding sequence, in its mature form, exhibits the serine protease specificity of SEQ ID NO:18.

4. The nucleic acid molecule of claim 2, wherein the nucleic acid sequence is a cDNA sequence comprising the coding sequence of the nucleotide sequence set forth in SEQ ID NO:15, wherein the polypeptide encoded by the coding sequence, in its mature form, exhibits the serine protease specificity of SEQ ID NO:18.

5. The nucleic acid molecule of claim 2, wherein the nucleic acid sequence is a cDNA sequence comprising the coding sequence of the nucleotide sequence set forth in SEQ ID NO:17, wherein the polypeptide encoded by the coding sequence exhibits the serine protease specificity of SEQ ID NO:18.

6. The nucleic acid molecule of claim 2, wherein the nucleic acid sequence is a cDNA sequence comprising the coding sequence of the nucleotide sequence set forth in SEQ ID NO:13 in plasmid pALK2531 contained in *E. coli* strain DSM 22209, wherein the coding sequence encodes a polypeptide, which in its mature form, exhibits the serine protease specificity of SEQ ID NO:18.

7. The nucleic acid molecule of claim 2, wherein the nucleic acid sequence is a cDNA sequence comprising the coding sequence of the nucleotide sequence set forth in SEQ ID NO:15 fused at its 5' end to the nucleotide sequence of a heterologous signal sequence, the coding sequence encoding a polypeptide, which in its mature form, exhibits the serine protease specificity of SEQ ID NO:18.

8. The expression vector of claim 1, wherein the vector comprises a nucleic acid sequence encoding a polypeptide exhibiting the serine protease specificity of SEQ ID NO:18 and comprising the amino acid sequence set forth in SEQ ID NO:18, the nucleic acid sequence operably linked to regulatory sequences capable of directing expression of the polypeptide encoded by the nucleic acid in a host cell.

9. An expression vector comprising the nucleic acid molecule of claim 3 operably linked to regulatory sequences capable of directing expression of the polypeptide encoded by the coding sequence in a host cell.

10. An expression vector comprising the nucleic acid molecule of claim 4 operably linked to regulatory sequences capable of directing expression of the polypeptide encoded by the coding sequence in a host cell.

11. An expression vector comprising the nucleic acid molecule of claim 5 operably linked to regulatory sequences capable of directing expression of the polypeptide encoded by the coding sequence in a host cell.

12. An expression vector comprising the nucleic acid molecule of claim 6 operably linked to regulatory sequences capable of directing expression of the polypeptide encoded by the coding sequence in a host cell.

13. An expression vector comprising the nucleic acid molecule of claim 7 operably linked to regulatory sequences capable of directing expression of the polypeptide encoded by the coding sequence in a host cell.

14. A host cell comprising the expression vector of claim 8.

15. A host cell comprising the expression vector of claim 9.

16. A host cell comprising the expression vector of claim 10.

17. A host cell comprising the expression vector of claim 11.

18. A host cell comprising the expression vector of claim 12.

19. A host cell comprising the expression vector of claim 13.

20. The host cell of claim 17, wherein the host cell is a microbial host cell.

21. The host cell of claim 17, wherein the host cell is a cell from a filamentous fungus.

22. The host cell of claim 21, wherein the filamentous fungus is of the genus *Trichoderma, Aspergillus, Fusarium, Humicola, Chrysosporium, Neurospora, Rhizopus, Penicillium*, or *Mortierella*.

23. The host cell of claim 21, wherein the filamentous fungus is of the genus *Trichoderma*.

24. The host cell of claim 21, wherein the filamentous fungus is of the genus *Aspergillus*.

25. The host cell of claim 23, wherein the host cell is from *Trichoderma reesei*.

26. The host cell of claim 17, wherein the host cell is a heterologous host cell.

27. The expression vector of claim 1, wherein the expression vector comprises the nucleic acid sequence encoding a polypeptide that comprises an amino acid sequence that exhibits serine protease activity and is at least 92% identical to the amino acid sequence set forth in SEQ ID NO:18, wherein sequence identity is determined using ClustalW alignment using matrix: BLOSUM, Gap Open: 10, and Gap Extension: 0.5, and wherein the amino acid sequence that exhibits serine protease activity has the serine protease specificity of SEQ ID NO:18, the nucleic acid sequence operably linked to regulatory sequences capable of directing expression of the polypeptide encoded by the nucleic acid in a host cell.

28. The expression vector of claim 1, wherein the expression vector comprises the nucleic acid sequence that hybridizes under stringent conditions with the complement of the nucleic acid sequence set forth in SEQ ID NO:12 contained in DSM 22208 and encodes a polypeptide comprising an amino acid sequence that exhibits the serine protease specificity of SEQ ID NO:18 and is at least 92% identical to the full-length amino acid sequence set forth in SEQ ID NO:18, wherein sequence identity is determined using ClustalW alignment using matrix: BLOSUM, Gap Open: 10, and Gap Extension: 0.5, and wherein stringent conditions comprise hybridization in a solution comprising 6×SSC, 5×Denhardt's reagent, and 0.5% SDS at 65° C., and washing twice for 15 minutes at 65° C. in a solution comprising 0.1×SSC and 0.1% SDS, the nucleic acid sequence operably linked to regulatory sequences capable of directing expression of the polypeptide encoded by the nucleic acid in a host cell.

29. A host cell comprising the expression vector of claim 28.

30. The host cell of claim 29, wherein the host cell is a microbial host cell.

31. The host cell of claim 29, wherein the host cell is a cell from a filamentous fungus.

32. The host cell of claim 31, wherein the filamentous fungus is of the genus *Trichoderma, Aspergillus, Fusarium, Humicola, Chrysosporium, Neurospora, Rhizopus, Penicillium*, or *Mortierella*.

33. The host cell of claim 32, wherein the filamentous fungus is of the genus *Trichoderma*.

34. The host cell of claim 32, wherein the filamentous fungus is of the genus *Aspergillus*.

35. A host cell comprising the expression vector of claim 27.

36. The expression vector of claim 27, wherein the nucleic acid sequence encodes a polypeptide that comprises an amino acid sequence that exhibits serine protease activity and is at least 94% identical to the amino acid sequence set forth in SEQ ID NO:18.

37. The expression vector of claim 27, wherein the nucleic acid sequence encodes a polypeptide that comprises an amino acid sequence that exhibits serine protease activity and is at least 96% identical to the amino acid sequence set forth in SEQ ID NO:18.

38. The expression vector of claim 27, wherein the nucleic acid sequence encodes a polypeptide that comprises an amino acid sequence that exhibits serine protease activity and is at least 98% identical to the amino acid sequence set forth in SEQ ID NO:18.

39. The expression vector of claim 27, wherein the nucleic acid sequence encodes a polypeptide that comprises an amino acid sequence that exhibits serine protease activity and is at least 99% identical to the amino acid sequence set forth in SEQ ID NO:18.

40. The host cell of claim 35, wherein the host cell is a cell from a filamentous fungus of the genus *Trichoderma, Aspergillus, Fusarium, Humicola, Chrysosporium, Neurospora, Rhizopus, Penicillium*, or *Mortierella*.

41. The host cell of claim 15, wherein the host cell is a microbial cell.

42. The host cell of claim 14, wherein the host cell is a microbial host cell.

43. The host cell of claim 14, wherein the host cell is a cell from a filamentous fungus.

44. The host cell of claim 43, wherein the filamentous fungus is of the genus *Trichoderma, Aspergillus, Fusarium, Humicola, Chrysosporium, Neurospora, Rhizopus, Penicillium*, or *Mortierella*.

45. The host cell of claim 44, wherein the filamentous fungus is of the genus *Trichoderma*.

46. The host cell of claim 44, wherein the filamentous fungus is of the genus *Aspergillus*.

* * * * *

UNITED STATES PATENT AND TRADEMARK OFFICE
CERTIFICATE OF CORRECTION

| | | |
|---|---|---|
| PATENT NO. | : 8,877,912 B2 | Page 1 of 3 |
| APPLICATION NO. | : 14/067040 | |
| DATED | : November 4, 2014 | |
| INVENTOR(S) | : Kari Juntunen et al. | |

It is certified that error appears in the above-identified patent and that said Letters Patent is hereby corrected as shown below:

On the title page,

On page 3, column 1 (Other Publications), line 48, delete "preoteinase-encoding" and insert -- proteinase-encoding --;

On page 3, column 2 (Other Publications), line 5, delete "procaryotic and eucaryotic" and insert -- prokaryotic and eukaryotic --;

On page 3, column 2 (Other Publications), line 60, delete "Hypoxrea lixii proteinn," and insert -- *Hypocrea lixii* protein, --;

On page 3, column 2 (Other Publications), lines 62-63, delete "Gibbereall amoniliformis" and insert -- *Gibberella moniliformis* --;

On page 3, column 2 (Other Publications), line 64, delete "Dtabase" and insert -- Database --;

In the drawings,

On sheet 21 of 21 (FIG. 15A), line 4 (Approx.), delete "Liguid" and insert -- Liquid --;

On sheet 21 of 21 (FIG. 15B), line 4 (Approx.), delete "Liguid" and insert -- Liquid --;

In the specification,

In column 3, line 20, after "mycelia" insert -- . --;

In column 4, line 15, delete "*Mortiriella*" and insert -- *Mortierella*. --;

In column 4, line 50, delete "*Mortiriella*." and insert -- *Mortierella*. --;

Signed and Sealed this
First Day of March, 2016

Michelle K. Lee
*Director of the United States Patent and Trademark Office*

CERTIFICATE OF CORRECTION (continued)

In column 4, line 58, delete "*Mortiriella.*" and insert -- *Mortierella.* --;

In column 7, line 30, after "protein" insert -- . --;

In column 9, lines 48-49, delete "*amyloliquifaciens,*" and insert -- *amyloliquefaciens,* --;

In column 11, line 27, delete "its the" and insert -- its --;

In column 15, line 46, delete "*Mortiriella*" and insert -- *Mortierella* --;

In column 16, line 33, delete "pBluescript 11" and insert -- pBluescript II --;

In column 16, line 48, delete "Arg 126." and insert -- Arg126. --;

In column 18, line 35, delete "sublitis" and insert -- *subtilis* --;

In column 19, line 9, delete "*Mortiriella,*" and insert -- *Mortierella,* --;

In column 19, line 19, delete "*Neurospora.*" and insert -- *Neurospora* --;

In column 19, line 20, delete "*Mortiriella alpinis,*" and insert -- *Mortierella alpine,* --;

In column 19, line 21, delete "*lucknowensee*" and insert -- *lucknowense* --;

In column 19, line 26, delete "*amyloliquelaciens,*" and insert -- *amyloliquefaciens,* --;

In column 23, line 65 (Approx.), delete "Centralbureau" and insert -- Centraalbureau --;

In column 24, lines 56-57 (Approx.), delete "Folin-Ciocalteau" and insert -- Folin-Ciocalteu --;

In column 25, line 62, delete "120A," and insert -- 120Å, --;

In column 25, lines 64-65, delete "polyvinylidine difluororide" and insert -- polyvinylidene difluoride --;

In columns 25-26 (Table 1), line 17 (Approx.), delete "TSY(L/I)YDTTAGSGSYGYYVDSG" and insert -- TSY(L/I)YDTTAGSGSYGYVVDSG --;

In column 26, line 57, delete "oligonuclotides" and insert -- oligonucleotides --;

In columns 27-28 (Table 2), line 4 (Approx.), delete "degenaracies," and insert -- degeneracies, --;

In column 28, line 59, delete "Gun et al.," and insert -- Gurr et al., --;

CERTIFICATE OF CORRECTION (continued)
U.S. Pat. No. 8,877,912 B2

In column 29, lines 15-16 (Approx.), delete "XP 383491)" and insert -- XP_383491) --;

In column 31, line 9, delete "Testmaterialen AG, Swizerland)" and insert -- Testmaterialien AG, Switzerland) --;

In column 31, line 17, delete "Glysine-" and insert -- Glycine- --;

In column 35 (Table 5), line 6 (Approx.), delete "Bood" and insert -- Blood --;

In column 36, line 9 (Approx.), delete "Testmaterialen AG, Swizerland)" and insert -- Testmaterialien AG, Switzerland) --;

In column 37, line 12, delete "proteiomics" and insert -- proteomics --;

In column 38, line 27, after "1692" insert -- . --.